United States Patent
Lim

(10) Patent No.: US 10,344,213 B2
(45) Date of Patent: Jul. 9, 2019

(54) REACTIVE MESOGEN AND LIQUID CRYSTAL COMPOSITION INCLUDING THE SAME

(71) Applicant: Samsung Display Co., Ltd., Yongin-si, Gyeonggi-do (KR)

(72) Inventor: Ho Lim, Suwon-si (KR)

(73) Assignee: Samsung Display Co., Ltd. (KR)

( * ) Notice: Subject to any disclaimer, the term of this patent is extended or adjusted under 35 U.S.C. 154(b) by 35 days.

(21) Appl. No.: 15/628,314

(22) Filed: Jun. 20, 2017

(65) Prior Publication Data

US 2018/0023000 A1    Jan. 25, 2018

(30) Foreign Application Priority Data

Jul. 22, 2016 (KR) .................. 10-2016-0093605
Aug. 24, 2016 (KR) .................. 10-2016-0107957

(51) Int. Cl.
*G02F 1/1333* (2006.01)
*C09K 19/38* (2006.01)
(Continued)

(52) U.S. Cl.
CPC .............. *C09K 19/38* (2013.01); *C09K 19/28* (2013.01); *C09K 19/3066* (2013.01);
(Continued)

(58) Field of Classification Search
CPC .... C09K 19/38; C09K 19/28; C09K 19/3006; C09K 19/34; C09K 19/3405;
(Continued)

(56) References Cited

U.S. PATENT DOCUMENTS 5,241,036 A    8/1993  Hsiue et al.
9,475,991 B2  10/2016  Kubota et al.
(Continued)

FOREIGN PATENT DOCUMENTS

WO    20090158483 A1    12/2009
WO     2012132936 A1    10/2012

OTHER PUBLICATIONS

Virgil Percec, "Liquid Crystal Polymers Containing Macroheterocyclic Ligands. 2. Side Chain Liquid Crystal Polysiloxanes and Polymethacrylates Containing 4-(w-Alkan-1-yloxy)-4'-(4'-carboxybenzo-15-crown-5) biphenyl Side Groups", Macromolecules, American Chemical Society, Dec. 1, 1989, pp. 4408-4412, US. vol. 22, No. 2.

(Continued)

*Primary Examiner* — Geraldina Visconti
(74) *Attorney, Agent, or Firm* — Innovation Counsel LLP

(57) ABSTRACT

Provided are a reactive mesogen that may improve display quality of a liquid crystal display, and a liquid crystal composition including the same. The reactive mesogen is represented by the following Formula:

$$B \!-\!\!\left[\!Z_1\!\right]_{\overline{b1}}\!\!-\!\!\left[\!A_1\!-\!L_1\!\right]_{\overline{a1}}\!\!-\!\!\left[\!A_2\!\right]_{\overline{a2}}\!\!-\!\!\left[\!L_2\!\right]_{\overline{a3}}\!\!-\!\!A_3\!\!-\!\!\left[\!Z_2\!\right]_{\overline{b2}}\!\!-\!\!Pa$$

where $A_1$, $A_2$, and $A_3$ are each independently a substituted or unsubstituted divalent hydrocarbon ring, or a substituted or unsubstituted divalent heterocycle, $L_1$ and $L_2$ are each independently a direct linkage, —O—, —S—, —CO—, —COO—, —OCOO—, —O$(CH_2)_{k1}$—, —S$(CH_2)_{k1}$—, —O$(CF_2)_{k1}$—, —S$(CF_2)_{k1}$—, —$(CH_2)_{k1}$—, —$CF_2CH_2$—, —$(CF_2)_{k1}$—, —CH=CH—, —CF=CF—, —C≡C—, —CH=CH—COO—, or —$(CH_2)_{k1}$—COO—$(CH_2)_{k2}$—O—, $Z_1$ and $Z_2$ are each independently a direct linkage, —O—, —S—, —CO—, —COO—, —OCOO—, —O$(CH_2)_{m1}$—, —S$(CH_2)_{m1}$—, —O$(CF_2)_{m1}$—, —S$(CF_2)_{m1}$—, —$(CH_2)_{m1}$—, —$CF_2CH_2$—, —$(CF_2)_{m1}$—, —CH=CH—, —CF=CF—, —C≡C—, —CH=CH—COO—, —$(CH_2)_{m1}$—COO—, —$(CH_2)_{m1}$—COO—$(CH_2)_{m2}$—O—, —CH—$(S_p$—Pa)—, —$CH_2CH$—$(S_p$—Pa)—, or —$(CH$—$(S_p$—Pa)—CH—$(S_p$—Pa))—, Pa is a polymerizable group, B is an unsubstituted heterocycle, a substituted or unsubstituted crown ether group, or $$*\!-\!N\!\!\begin{matrix}\left[CH_2\right]_{n1}\!\!-\!\!T_1\\ \left[CH_2\right]_{n2}\!\!-\!\!T_2,\end{matrix}$$

wherein $T_1$ and $T_2$ are each independently —OH, —$CH_3$, —$CF_3$, —$CHF_2$, —$CH_2F$, —$CH_2Br$, —$CHBr_2$, —$CHCl_2$, or —$CH_2Cl$.

12 Claims, 17 Drawing Sheets

(51) Int. Cl.
*C09K 19/28* (2006.01)
*C09K 19/30* (2006.01)
*C09K 19/34* (2006.01)
*C07D 273/00* (2006.01)
*C09K 19/04* (2006.01)
*C09K 19/12* (2006.01)

(52) U.S. Cl.
CPC .......... *C09K 19/34* (2013.01); *C09K 19/3405* (2013.01); *C09K 19/3441* (2013.01); *C09K 19/3455* (2013.01); *C09K 19/3486* (2013.01); *C09K 19/3488* (2013.01); *C07D 273/00* (2013.01); *C09K 2019/0407* (2013.01); *C09K 2019/0414* (2013.01); *C09K 2019/0448* (2013.01); *C09K 2019/122* (2013.01); *C09K 2019/3422* (2013.01); *C09K 2019/3438* (2013.01)

(58) Field of Classification Search
CPC ............ C09K 19/3441; C09K 19/3455; C09K 19/3486; C09K 19/3488; C09K 2019/0414; C09K 2019/0448; C09K 2019/122; C09K 2019/3422; C09K 2019/3438; G02F 1/1333; C07D 273/00
USPC .................................................... 252/299.01
See application file for complete search history.

(56) References Cited

U.S. PATENT DOCUMENTS

| | | |
|---|---|---|
| 2009/0163683 A1 | 6/2009 | Kim et al. |
| 2015/0252265 A1 | 9/2015 | Archetti et al. |
| 2015/0301368 A1 | 10/2015 | Archetti et al. |
| 2015/0322342 A1 | 11/2015 | Archetti et al. |
| 2018/0362850 A1* | 12/2018 | Lim ...................... C09K 19/56 |

OTHER PUBLICATIONS

KH. M. Alimardanov, "Synthesis and Examination of Antimicrobial Properties of Aminomethylated Derivatives C6-C7 of Alicyclic Diols", Russian Journal of Applied Chemistry, Jul. 1, 2009, pp. 1255-1262, vol. 82, No. 7.

* cited by examiner

Compound - I

Compound - II

Compound - III

REACTIVE MESOGEN AND LIQUID CRYSTAL COMPOSITION INCLUDING THE SAME

CROSS-REFERENCE TO RELATED APPLICATIONS

This U.S. non-provisional patent application claims priority under 35 U.S.C. § 119 of Korean Patent Application Nos. 10-2016-0093605, filed on Jul. 22, 2016, and 10-2016-0107957, filed on Aug. 24, 2016, the entire contents of which are hereby incorporated by reference.

BACKGROUND

The present disclosure herein relates to a reactive mesogen and a liquid crystal composition including the same, and more particularly, to a reactive mesogen configured to form a liquid crystal alignment layer in a liquid crystal display and a liquid crystal composition including the same.

Generally, liquid crystal displays are classified as a twisted nematic mode liquid crystal display, an in-plane switching mode liquid crystal display, a vertical alignment mode liquid crystal display, etc. In the vertical alignment mode liquid crystal display without applying an electric field, liquid crystal molecules are characterized in aligning in a pre-determined direction, and the longitudinal axes thereof are vertically aligned with respect to a substrate surface. Accordingly, the vertical alignment mode liquid crystal display has merits of a wide viewing angle and a high contrast ratio.

Meanwhile, in order to align liquid crystal molecules in a pre-determined direction, a rubbing method, a photo-aligning method, etc. are used. In a vertical alignment mode liquid crystal display, methods for aligning liquid crystal molecules in a pre-determined direction using a reactive mesogen are suggested.

SUMMARY

The present disclosure provides a novel reactive mesogen used in a liquid crystal display.

The present disclosure also provides a novel reactive mesogen configured to stably form an alignment layer in a liquid crystal display and a liquid crystal composition including the same.

An embodiment of the inventive concept provides a reactive mesogen represented by the following Formula 1.

[Formula 1]

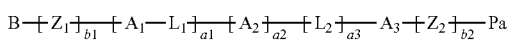

In Formula 1, $A_1$, $A_2$, and $A_3$ are each independently a substituted or unsubstituted divalent hydrocarbon ring, or a substituted or unsubstituted divalent heterocycle. a1, b1, and b2 are each independently an integer of 0 to 6, a2 and a3 are each independently 0 or 1. $L_1$ and $L_2$ are each independently a direct linkage, —O—, —S—, —CO—, —COO—, —OCOO—, —O(CH$_2$)$_{k1}$—, —S(CH$_2$)$_{k1}$—, —O(CF$_2$)$_{k1}$—, —S(CF$_2$)$_{k1}$—, —(CH$_2$)$_{k1}$—, —CF$_2$CH$_2$—, —(CF$_2$)$_{k1}$—, —CH=CH—, —CF=CF—, —C≡C—, —CH=CH—COO—, or —(CH$_2$)$_{k1}$—COO—(CH$_2$)$_{k2}$—O—, k1 and k2 are each independently an integer of 0 to 4. $Z_1$ and $Z_2$ are each independently a direct linkage, —O—, —S—, —CO—, —COO—, —OCOO—, —O(CH$_2$)$_{m1}$—, —S(CH$_2$)$_{m1}$—, —O(CF$_2$)$_{m1}$—, —S(CF$_2$)$_{m1}$—, —(CH$_2$)$_{m1}$—, —CF$_2$CH$_2$—, —(CF$_2$)$_{m1}$—, —CH=CH—, —CF=CF—, —C≡C—, —CH=CH—COO—, —(CH$_2$)$_{m1}$—COO—, —(CH$_2$)$_{m1}$—COO—(CH$_2$)$_{m2}$—O—, —CH—(S$_p$—Pa)—, —CH$_2$CH—(S$_p$—Pa)—, or —(CH—(S$_p$—Pa)—CH—(S$_p$—Pa))—, m1 and m2 are each independently an integer of 0 to 4. $S_p$ is a direct linkage, or a spacer group, Pa is a polymerizable group.

B is an unsubstituted heterocycle, a substituted or unsubstituted crown ether group, or

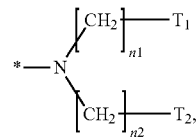

n1 and n2 are each independently an integer of 1 to 12, $T_1$ and $T_2$ are each independently —OH, —CH$_3$, —CF$_3$, —CHF$_2$, —CH$_2$F, —CH$_2$Br, —CHBr$_2$, —CHCl$_2$, or —CH$_2$Cl, and at least one of $T_1$ and $T_2$ is —OH.

In an embodiment, $A_1$, $A_2$, and $A_3$ may be each independently a substituted or unsubstituted aromatic ring having 6 to 30 carbon atoms for forming a ring, a substituted or unsubstituted heteroaromatic ring having 2 to 30 carbon atoms for forming a ring, a substituted or unsubstituted aliphatic ring having 5 to 30 carbon atoms for forming a ring, or a substituted or unsubstituted hetero aliphatic ring having 2 to 30 carbon atoms for forming a ring.

In an embodiment, $A_1$, $A_2$, and $A_3$ may be each independently selected from substituted or unsubstituted ring compounds of the following A-1 to A-22.

A-1

A-2

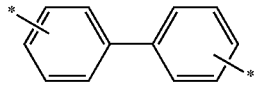

A-3

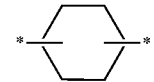

A-4

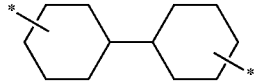

A-5

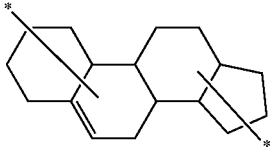

A-6

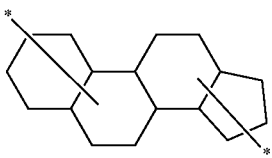

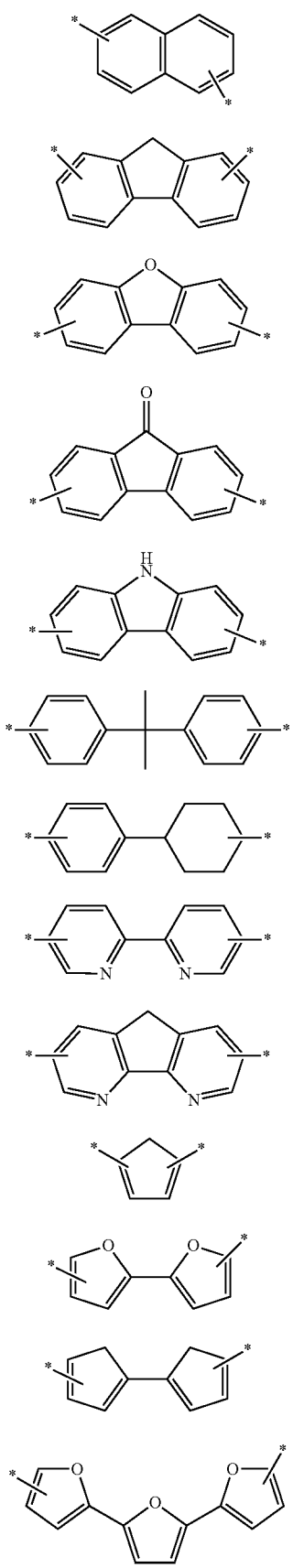
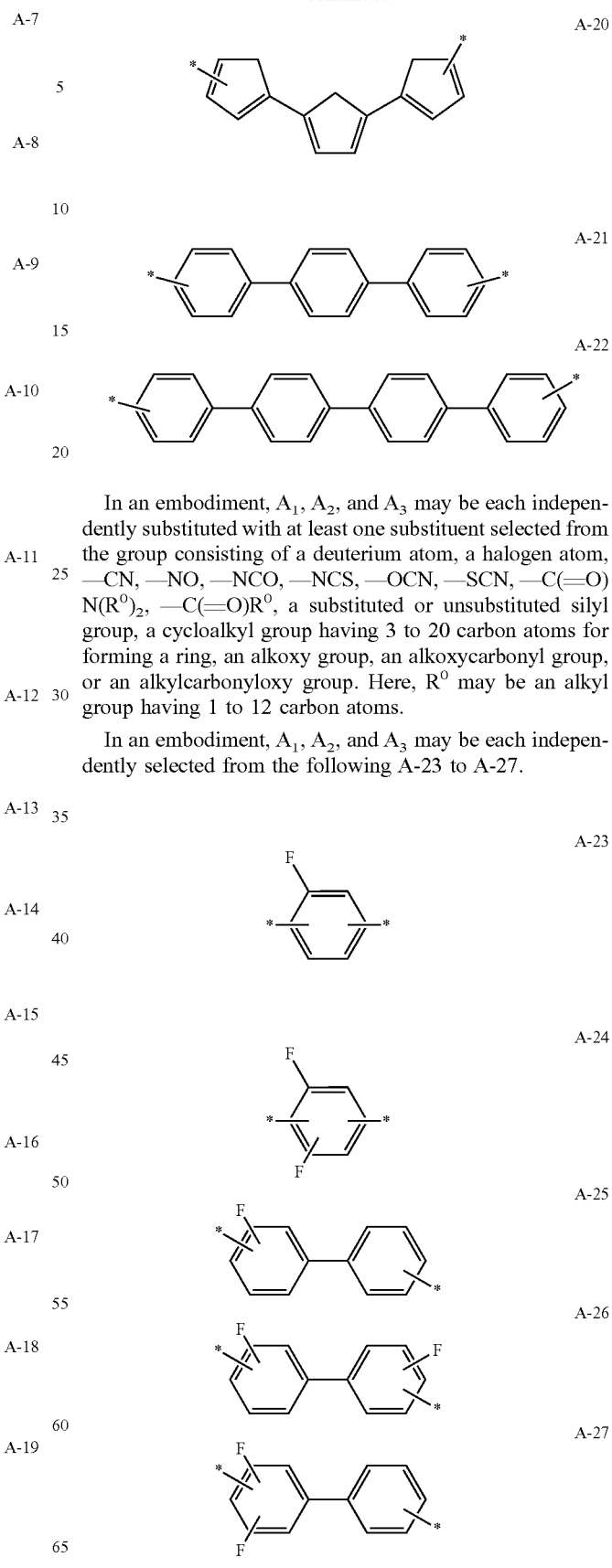

In an embodiment, $A_1$, $A_2$, and $A_3$ may be each independently substituted with at least one substituent selected from the group consisting of a deuterium atom, a halogen atom, —CN, —NO, —NCO, —NCS, —OCN, —SCN, —C(=O)N(R°)₂, —C(=O)R°, a substituted or unsubstituted silyl group, a cycloalkyl group having 3 to 20 carbon atoms for forming a ring, an alkoxy group, an alkoxycarbonyl group, or an alkylcarbonyloxy group. Here, R° may be an alkyl group having 1 to 12 carbon atoms.

In an embodiment, $A_1$, $A_2$, and $A_3$ may be each independently selected from the following A-23 to A-27.

In an embodiment, B may be
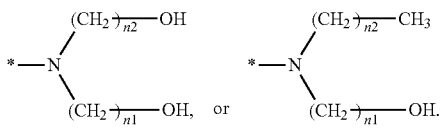
In an embodiment, B may be one of the following B-1 to B-18.
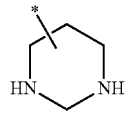
B-1
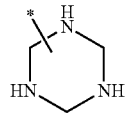
B-2
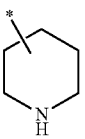
B-3
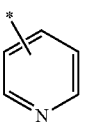
B-4
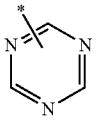
B-5
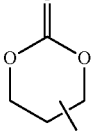
B-6
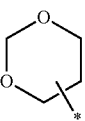
B-7
B-8
B-9
B-10
B-11
B-12
B-13
B-14
B-15
B-16
B-17
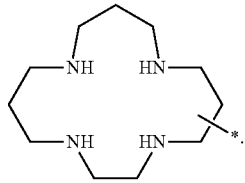
B-18
In an embodiment, B may be one of the following E-1 to E-13.
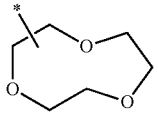
E-1
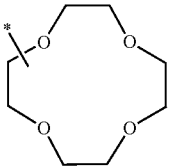
E-2

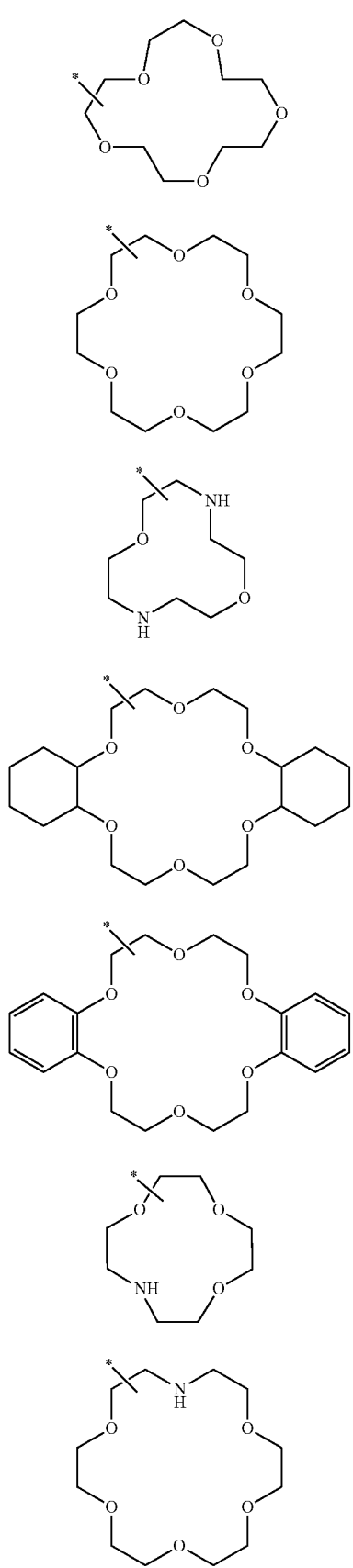
In an embodiment, Pa may be one of the following P-1 to P-9.
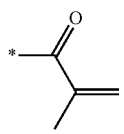
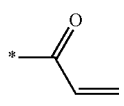
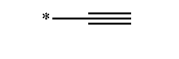
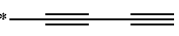

P-6
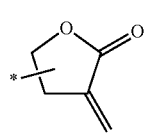
P-7
*—O—C(=O)—CH2—CH=CH2
P-8
(structure shown)
P-9
(structure shown)
In an embodiment, Formula 1 may be selected from compounds in the following Compound Group 1.
[Compound Group 1]
1
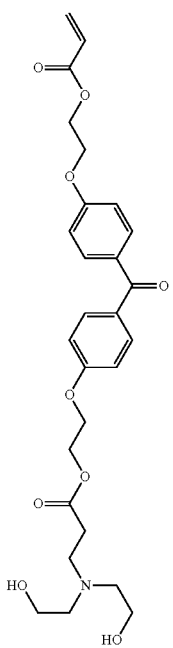
2
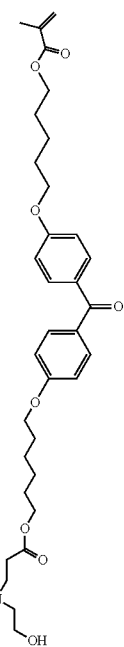
3
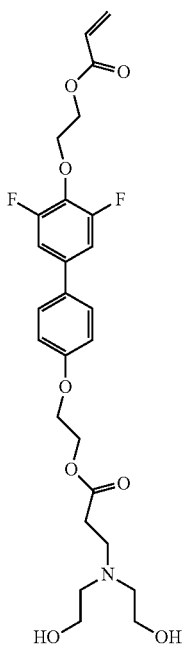

-continued
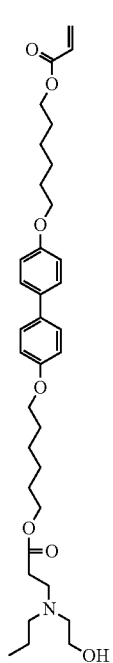
4
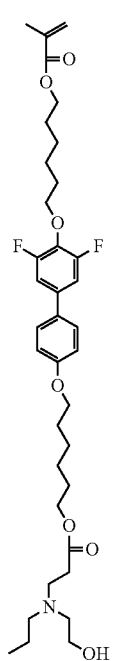
5
[Compound Group 2]
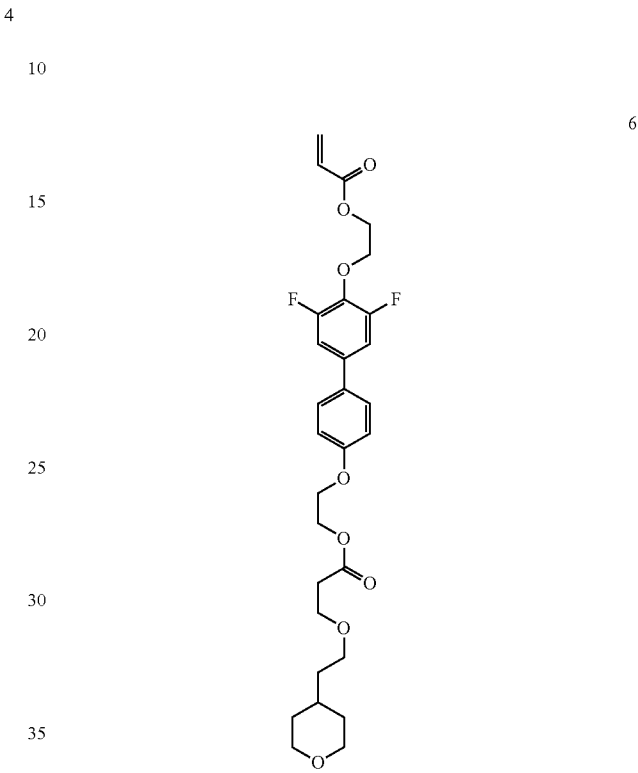
6
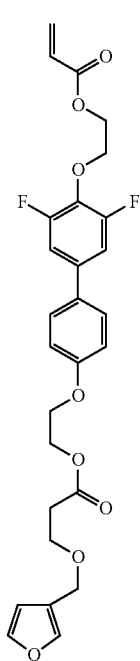
7
In an embodiment, Formula 1 may be selected from compounds in the following Compound Group 2.

8
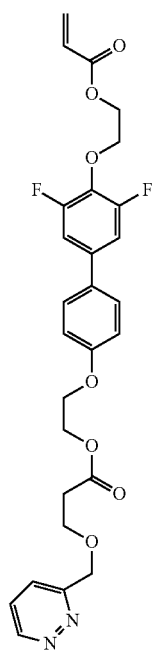
9
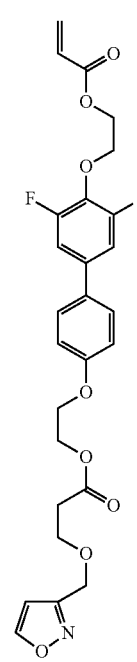
10
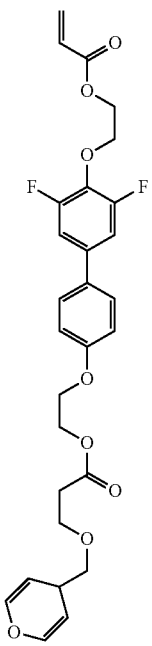
11
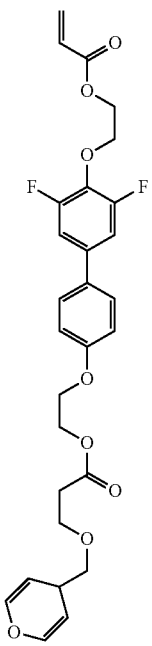
In an embodiment, Formula 1 may be selected from compounds in the following Compound Group 3.

[Compound Group 3]
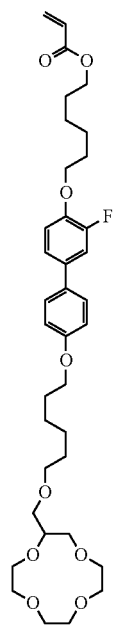
12
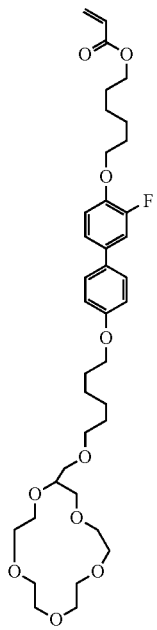
13
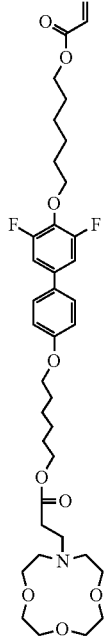
14
In an embodiment of the inventive concept, a reactive mesogen is represented by the following Formula 2.
$$B\text{-}(Z_1)_{b1}\text{-}X\text{-}(Z_2)_{b2}\text{-}Pa \quad \text{[Formula 2]}$$
In Formula 2, X is one of the following X-1 to X-17.
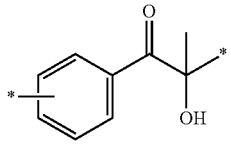
X-1
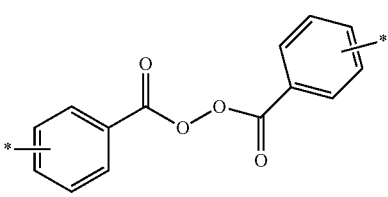
X-2
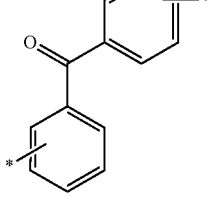
X-3

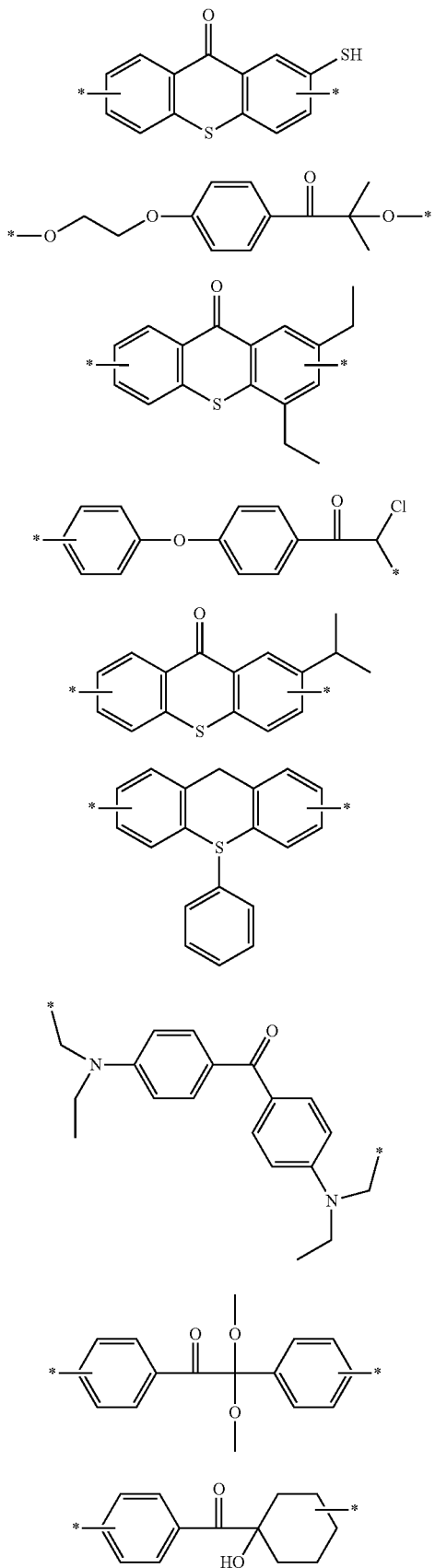
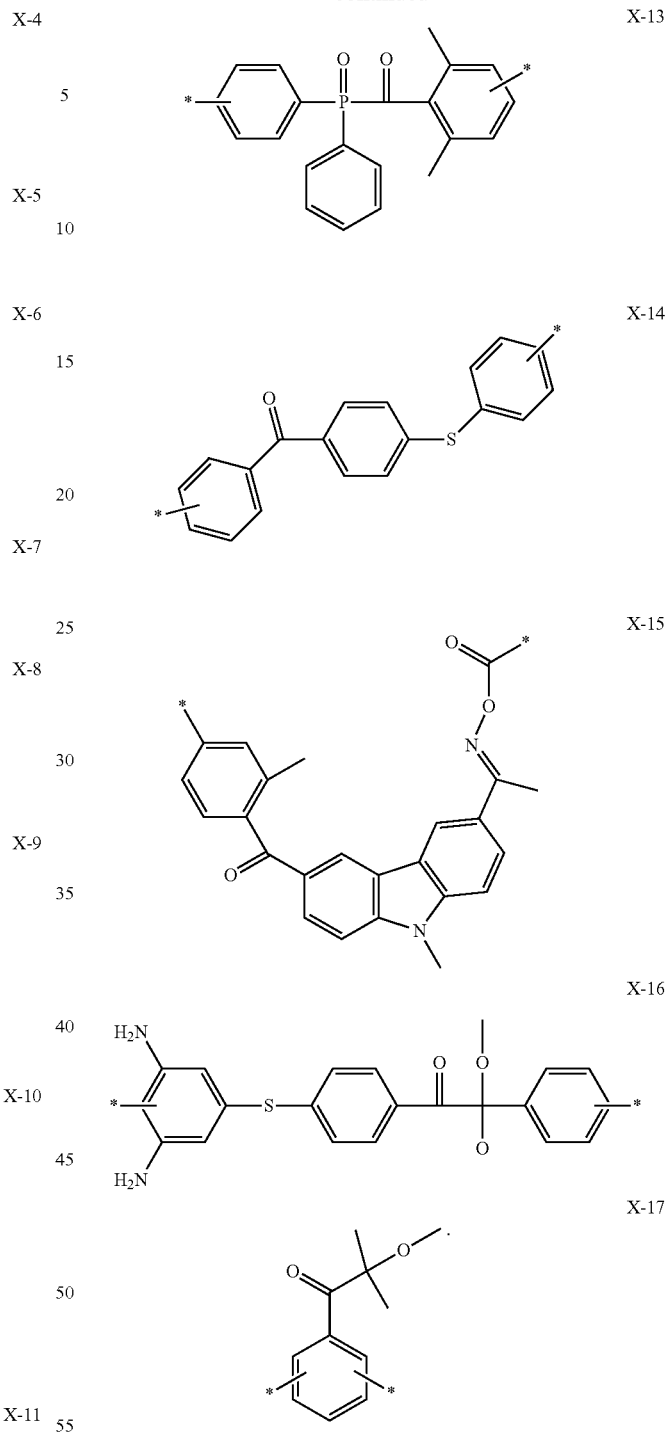

$Z_1$ and $Z_2$ are each independently a direct linkage, —O—, —S—, —CO—, —COO—, —OCOO—, —O(CH$_2$)$_{m1}$—, —S(CH$_2$)$_{m1}$—, —O(CF$_2$)$_{m1}$—, —S(CF$_2$)$_{m1}$—, —(CH$_2$)$_{m1}$—, —CF$_2$CH$_2$—, —(CF$_2$)$_{m1}$—, —CH=CH—, —CF=CF—, —C≡C—, —CH=CH—COO—, —(CH$_2$)$_{m1}$—COO—, —(CH$_2$)$_{m1}$—COO—(CH$_2$)$_{m2}$—O—, —CH—(S$_p$—Pa)—, —CH$_2$CH—(S$_p$—Pa)—, or —(CH—(S$_p$—Pa))—CH—(S$_p$—Pa))—, m1 and m2 are each independently an integer of 0 to 4. S$_p$ is a direct linkage, or a spacer group.

B is an unsubstituted heterocycle, a substituted or unsubstituted crown ether group, or

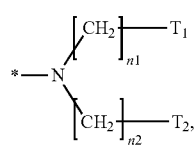
$n1$ and $n2$ are each independently an integer of 1 to 12, $T_1$ and $T_2$ are each independently —OH, —CH$_3$, —CF$_3$, —CHF$_2$, —CH$_2$F, —CH$_2$Br, —CHBr$_2$, —CHCl$_2$, or —CH$_2$Cl, and at least one of $T_1$ and $T_2$ is —OH.
In an embodiment, B may be one of the following B-1 to B-20 and E-1 to E-13.
B-1
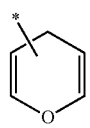
B-2
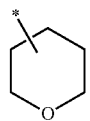
B-3
B-4
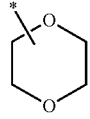
B-5
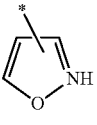
B-6
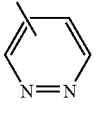
B-7
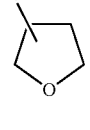
B-8
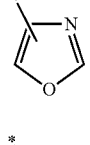
B-9
B-10
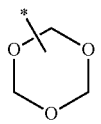
B-11
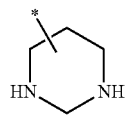
B-12
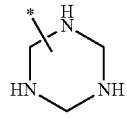
B-13
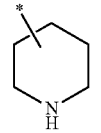
B-14
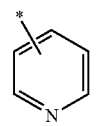
B-15
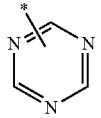
B-16
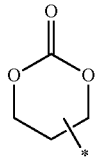
B-17
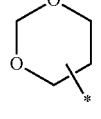
B-18
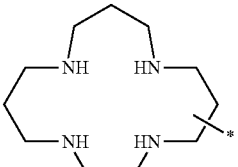
B-19
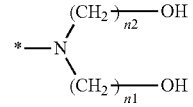
B-20

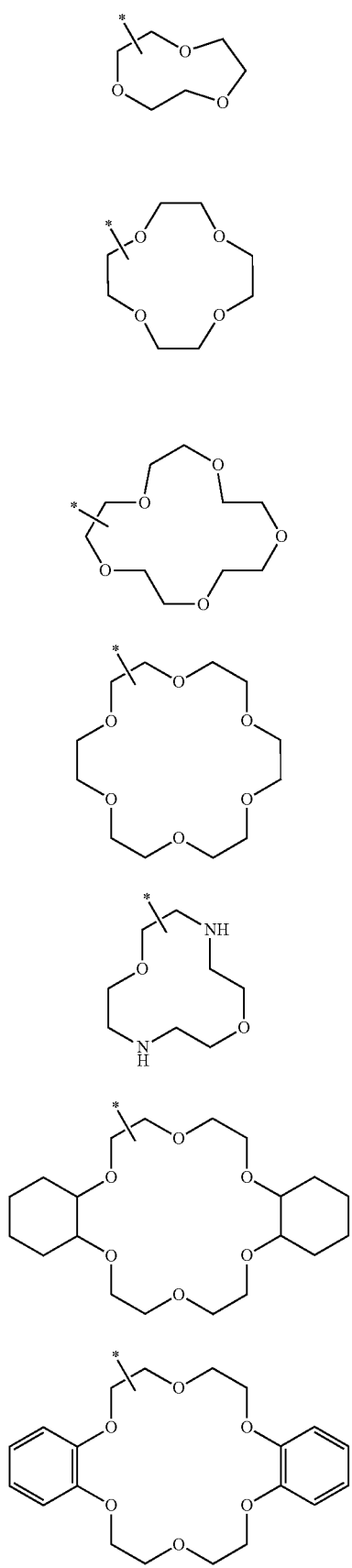
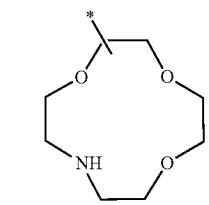
E-1
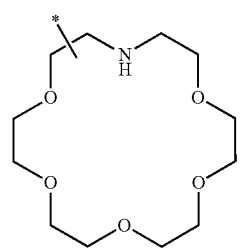
E-8
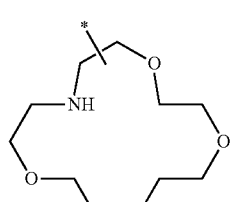
E-9
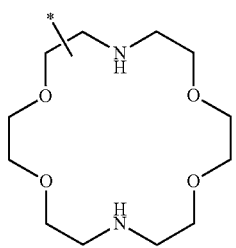
E-10
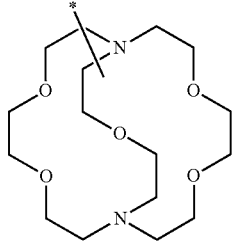
E-11
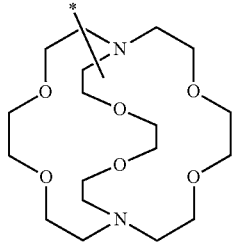
E-12
E-13
In an embodiment, Pa may be one of the following P-1 to P-9.

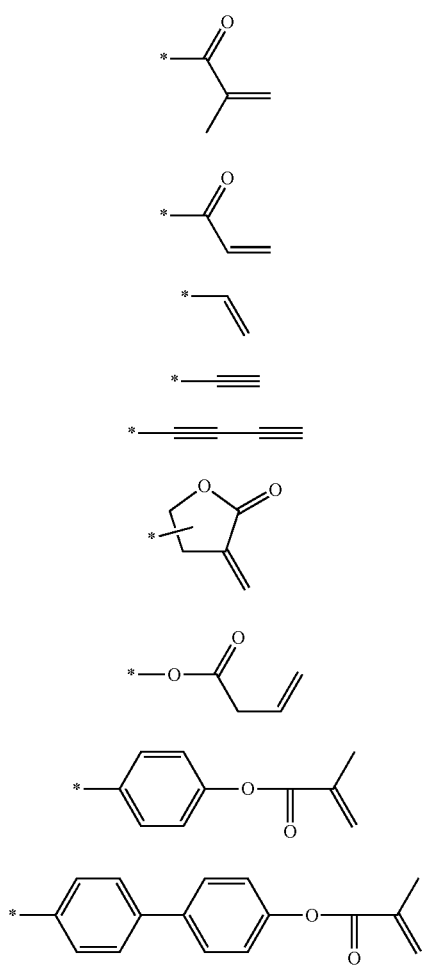

In an embodiment of the inventive concept, a liquid crystal composition includes a liquid crystal compound; and a first reactive mesogen represented by the following Formula 3.

[Formula 3]

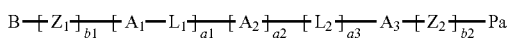

In Formula 3, $A_1$, $A_2$, $A_3$, $L_1$, $L_2$, $Z_1$, $Z_2$, Pa, B, a1, a2, a3, b1, and b2 are the same as defined in Formula 1.

In an embodiment, the liquid crystal composition may further include a second reactive mesogen represented by the following Formula 4.

[Formula 4]

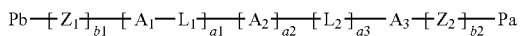

In Formula 4, Pa and Pb are each independently one of the following polymerizable groups P-1 to P-10, wherein a group where Pa and Pb are P-10 at the same time is excluded, and p is an integer of 1 to 20.

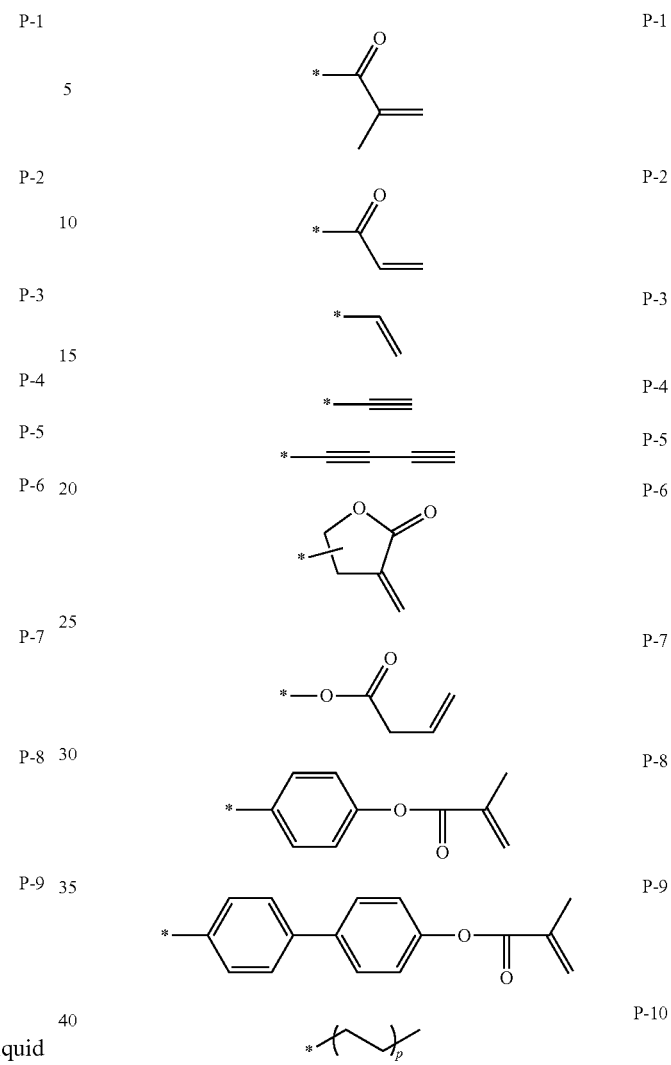

In Formula 4, each of $A_1$, $A_2$, $A_3$, $L_1$, $L_2$, $Z_1$, $Z_2$, a1, a2, a3, b1, and b2 are the same as defined in Formula 1.

In an embodiment, the liquid crystal composition may further include a third reactive mesogen represented by the following Formula 5.

[Formula 5]

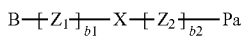

In Formula 5, X is one of the following X-1 to X-17, and $Z_1$, $Z_2$, B, and Pa are the same as defined in Formula 1.

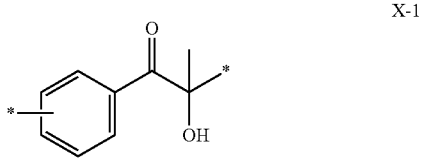

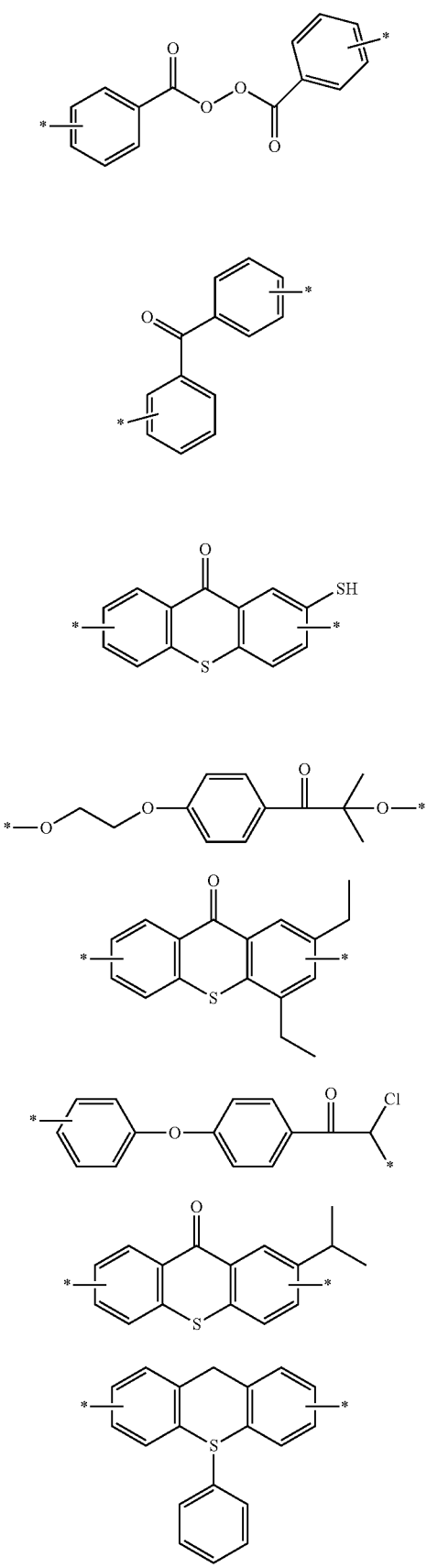
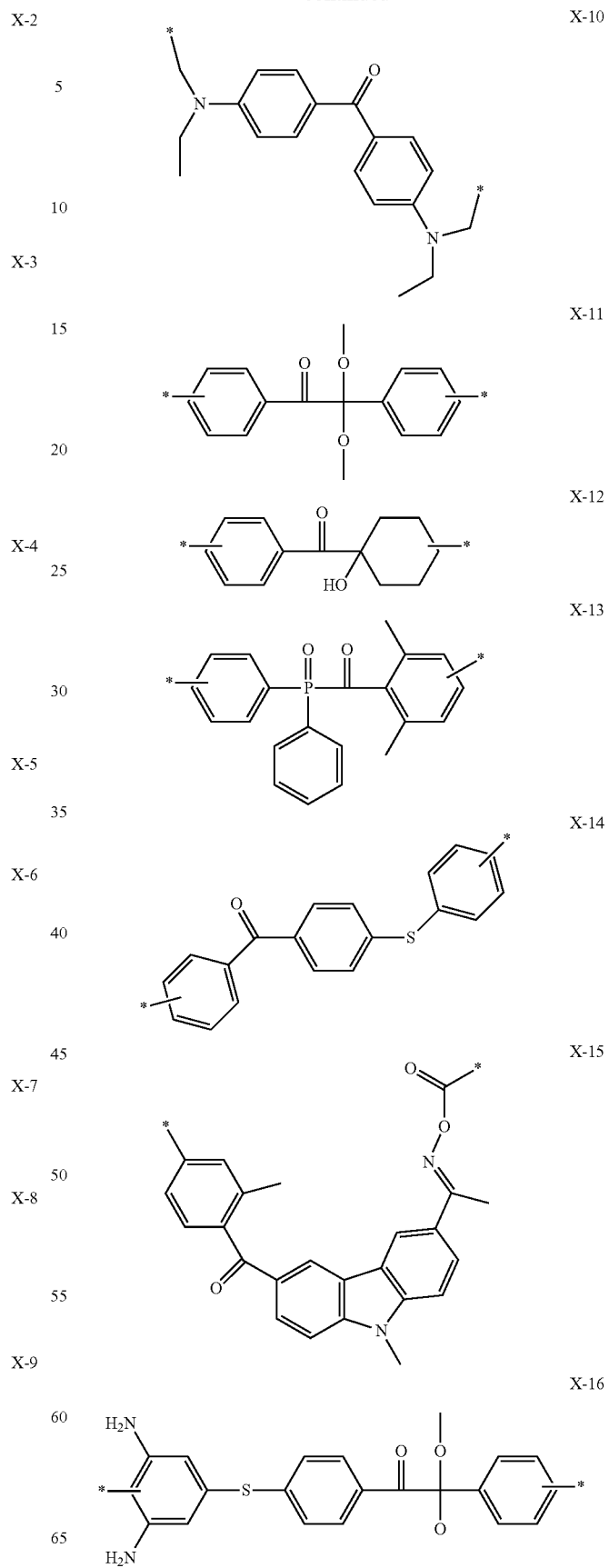

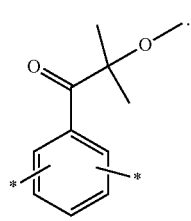
X-17

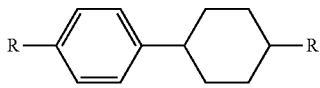
L-10

In an embodiment, the first reactive mesogen may be included in an amount 0.1 to 2 parts by weight on the basis of 100 parts by weight of the liquid crystal compound.

In an embodiment, the third reactive mesogen may be included in an amount 1 to 10 parts by weight on the basis of 100 parts by weight of a sum of the first reactive mesogen and the second reactive mesogen.

In an embodiment, the liquid crystal compound may include a nematic liquid crystal compound.

In an embodiment, the liquid crystal compound may include at least one of the following L-1 to L-10.

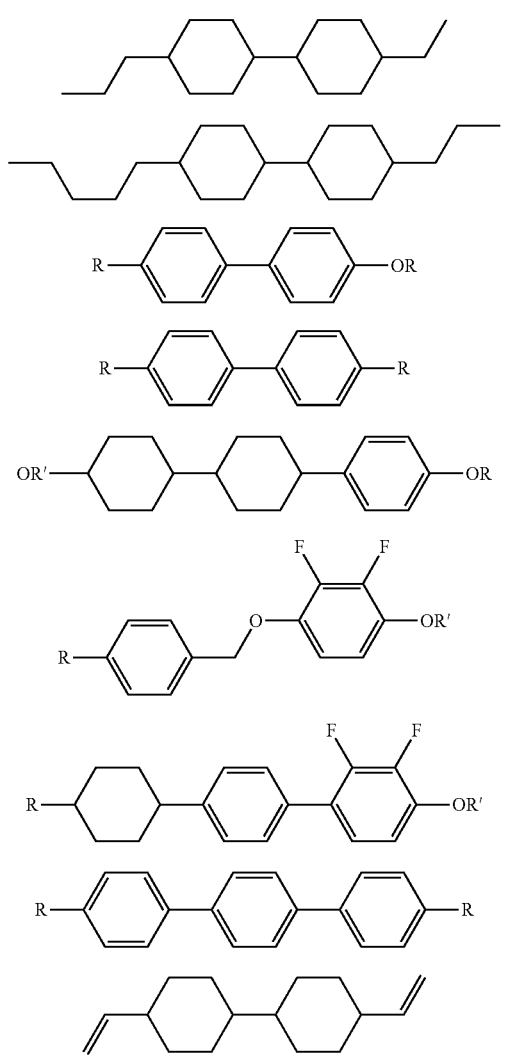

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
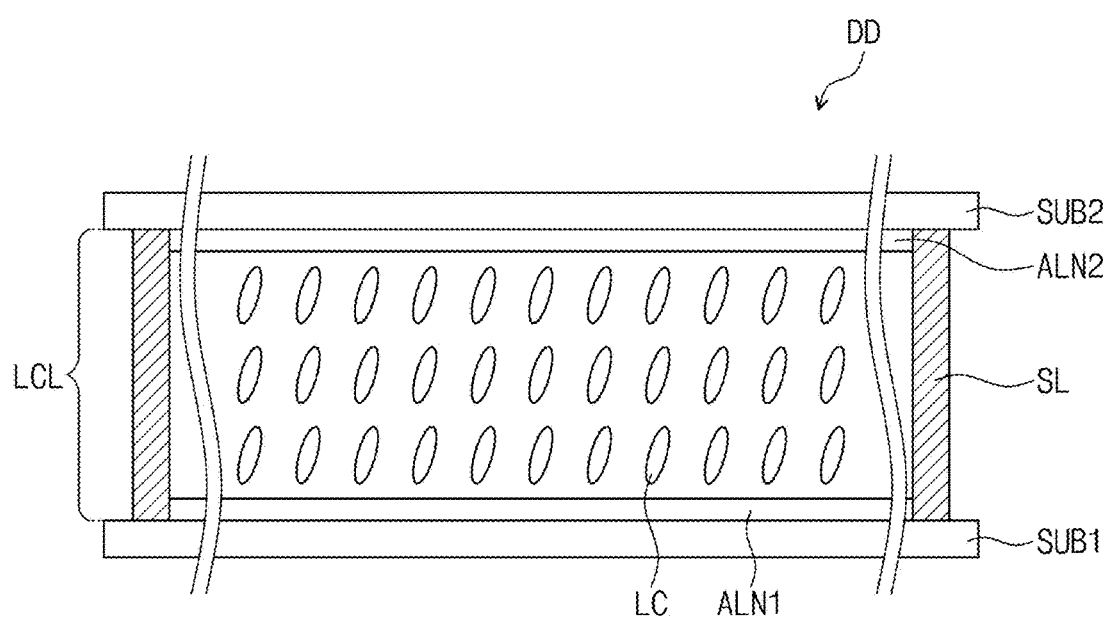
FIG. 1 is a cross-sectional view of a liquid crystal display including an alignment layer formed using a reactive mesogen according to an embodiment.

The inventive concept may be embodied in different forms and may have various modifications, and exemplary embodiments of the inventive concept will be described below in more detail with reference to the accompanying drawings. The inventive concept, however, should not be construed as limited to the embodiments set forth herein. Rather, these embodiments should be understood to include modifications, equivalents, or substitutes within the spirit and scope of the inventive concept.

In the drawings, like reference numerals refer to like elements throughout. The dimensions of structures are exaggerated for clarity of illustration. It will be understood that, although the terms first, second, etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof. It will also be understood that when a layer, a film, a region, a plate, etc. is referred to as being 'on' another part, it can be directly on the other part, or intervening layers may also be present. On the contrary, it will be understood that when a layer, a film, a region, a plate, etc. is referred to as being 'under' another part, it can be directly under, and one or more intervening layers may also be present. In addition, it will also be understood that when a plate is referred to as being disposed above another part, it can be disposed above or beneath another part.

In the description, the term "substituted or unsubstituted" corresponds to substituted or unsubstituted with at least one substituent selected from the group consisting of deuterium, a halogen atom, a cyano group, a nitrile group, a nitro group, an amino group, a silyl group, a boron group, a phosphine oxide group, an alkyl group, an alkenyl group, a fluorenyl group, an aryl group, and a heterocycle. In addition, each of the substituents may be substituted or unsubstituted. For example, a biphenyl group may be interpreted as an aryl group, or a phenyl group substituted with a phenyl group.

In the description, the terms "forming a ring via the combination of adjacent groups" may mean forming a substituted or unsubstituted hydrocarbon ring, or substituted or unsubstituted heterocycle via the combination of adjacent groups. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocycle or polycycle. In addition, a ring formed via the combination of adjacent groups may be combined with another ring to form a spiro structure.

In the description, the terms "an adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the description, the halogen may include fluorine, chlorine, bromine and iodine.

In the description, the alkyl may be a linear, branched or cyclic type. The carbon number of the alkyl may be from 1 to 30, from 1 to 20, from 1 to 10, or from 1 to 6. The alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the aryl may be monocyclic aryl or polycyclic aryl. The explanation of the arylene may be the same as that of the aryl except that the arylene is divalent. The aryl may be monocyclic aryl or polycyclic aryl. The carbon number for forming a ring in the aryl may be 6 to 30, 6 to 20, or 6 to 15. Examples of the aryl may include phenyl, naphthyl, anthracenyl, phenanthryl, biphenyl, terphenyl, quaterphenyl, quinqphenyl, sexiphenyl, triphenylene, pyrenyl, fluorenyl, benzofluoranthenyl, chrysenyl, etc. However, an embodiment of the aryl is not limited thereto. In addition, the aryl may be substituted or unsubstituted. In the substituted aryl, two substituents may combine with each other to form a spiro structure. For example, in the case where fluorenyl group is substituted,

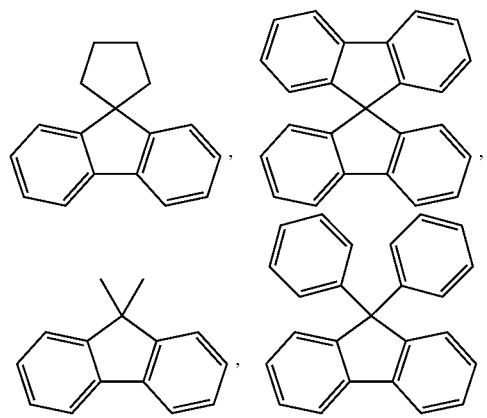

etc. may be obtained. However, an embodiment is not limited thereto.

In the description, the heteroaryl may be heteroaryl including at least one of O, N or S as a heteroatom. The carbon number for forming a ring of the heteroaryl may be 2 to 30, or 2 to 20. Examples of the heteroaryl may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzufuranyl, etc., without limitation.

In the description, explanation on the aryl may be applied to the arylene except that the arylene is a divalent group. In addition, the divalent group of biphenyl which is an aryl group may be represented by divalent biphenyl.

In the description, explanation on the heteroarylene may be applied to heteroaryl except that the heteroarylene is a divalent group.

In the description, "—*" may mean a connecting part in a compound.

Hereinafter, a reactive mesogen according to an embodiment will be explained. The reactive mesogen according to an embodiment is represented by the following Formula 1.

[Formula 1]

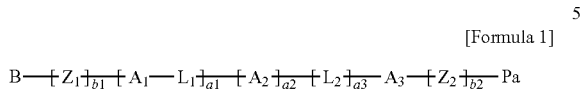

In Formula 1, $A_1$, $A_2$, and $A_3$ may be each independently a substituted or unsubstituted divalent hydrocarbon ring, or a substituted or unsubstituted divalent heterocycle. a1, b1, and b2 may be each independently an integer of 0 to 6, and a2 and a3 may be each independently 0 or 1.

Meanwhile, in the case where a1, b1, and b2 are an integer of 2 or more, $A_1$-$L_1$, $Z_1$, and $Z_2$ may be obtained by connecting the same or different groups. For example, in the case where b1 is 2 or more, $Z_1$ may be obtained by repeating one group among the exemplary groups of $Z_1$ below or by connecting different groups. In addition, the same applies to a case where a1 is 2 or more ($A_1$-$L_1$) and a case where b2 is 2 or more ($Z_2$).

$A_1$, $A_2$, and $A_3$ may be each independently a substituted or unsubstituted aromatic ring having 6 to 30 carbon atoms for forming a ring, a substituted or unsubstituted heteroaromatic ring having 2 to 30 carbon atoms for forming a ring, a substituted or unsubstituted aliphatic ring having 5 to 30 carbon atoms for forming a ring, or a substituted or unsubstituted hetero aliphatic ring having 2 to 30 carbon atoms for forming a ring. Meanwhile, a heteroatom in a heterocycle may be O, N, or S. In addition, $A_1$, $A_2$, and $A_3$ may be a polycyclic group, and the polycyclic group may be a condensed ring formed by combining an adjacent ring or an adjacent substituent with a ring.

$A_1$, $A_2$, and $A_3$ may be a divalent cyclic compound such as substituted or unsubstituted arylene having 6 to 30 carbon atoms, or substituted or unsubstituted heteroarylene having 2 to 30 carbon atoms for forming a ring. In addition, $A_1$, $A_2$, and $A_3$ may be divalent substituted or unsubstituted cycloalkane or cycloalkene having 5 to 30 carbon atoms for forming a ring, or divalent substituted or unsubstituted heterocycloalkane or heterocycloalkene having 2 to 30 carbon atoms for forming a ring.

Meanwhile, in the case where a1 is an integer of 2 or more, $A_1$-$L_1$ may be obtained by repeating the same group. In addition, $A_1$-$L_1$ may be obtained by connecting different groups.

$A_1$, $A_2$, and $A_3$ may be each independently selected from substituted or unsubstituted ring compounds of the following A-1 to A-22.

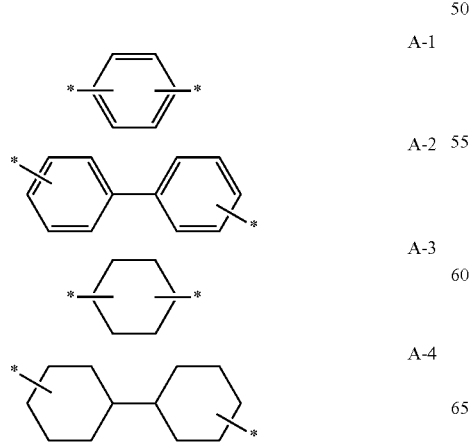

-continued

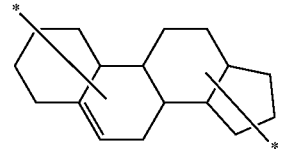
A-5

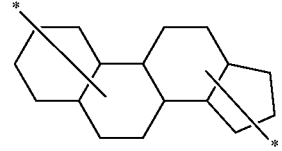
A-6

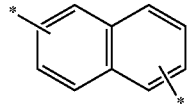
A-7

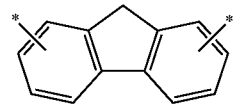
A-8

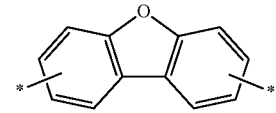
A-9

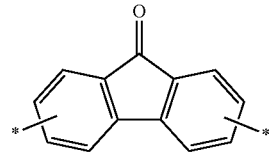
A-10

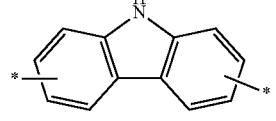
A-11

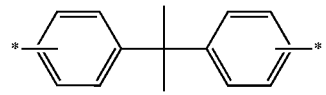
A-12

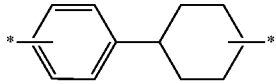
A-13

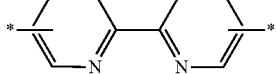
A-14

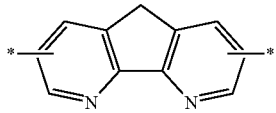
A-15

A-16

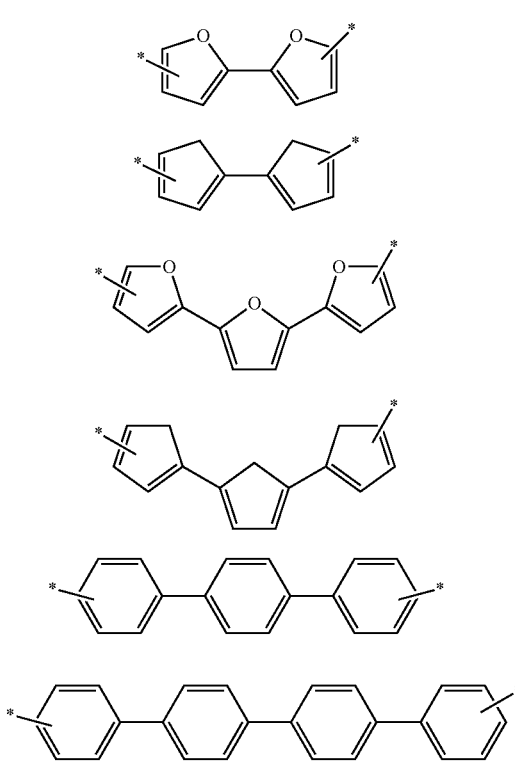

A-17

A-18

A-19

A-20

A-21

A-22

$A_1$, $A_2$, and $A_3$ may be each independently substituted with at least one substituent selected from the group consisting of a deuterium atom, a halogen atom, —CN, —NO, —NCO, —NCS, —OCN, —SCN, —C(=O)N($R^0$)$_2$, —C(=O)$R^0$, a substituted or unsubstituted silyl group, a cycloalkyl group having 3 to 20 carbon atoms for forming a ring, an alkoxy group, an alkoxycarbonyl group, or an alkylcarbonyloxy group. Here, $R^0$ may be an alkyl group having 1 to 12 carbon atoms. The halogen atom may be F, Cl, Br, or I. In addition, in the substituted silyl, a substituent may be aryl, cycloalkyl, linear alkyl, branched alkyl, alkoxy, alkylcarbonyl, or alkoxycarbonyl. In this case, the carbon number of the alkyl may be 1 to 25.

For example, $A_1$, $A_2$, and $A_3$ may be each independently selected from the following A-23 to A-27.

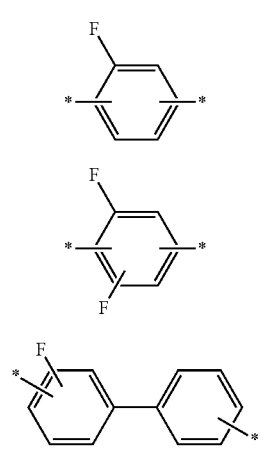

A-23

A-24

A-25

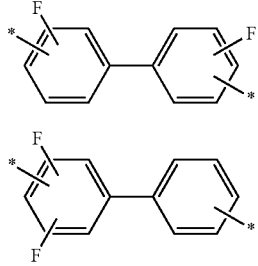

A-26

A-27

In Formula 1, B may correspond to an anchoring group. That is, B may be a bonding group so that a reactive mesogen may be adsorbed onto a substrate provided. For example, the anchoring group B may make a hydrogen bond with a transparent electrode formed on a base substrate provided in a liquid crystal display which will be explained below.

In Formula 1, B may be an unsubstituted heterocycle, a substituted or unsubstituted crown ether group, or a tertiary amine represented by

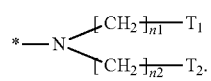

In addition, n1 and n2 may be each independently an integer of 1 to 12, $T_1$ and $T_2$ may be each independently —OH, —CH$_3$, —CF$_3$, —CHF$_2$, —CH$_2$F, —CH$_2$Br, —CHBr$_2$, —CHCl$_2$, or —CH$_2$Cl. Here, at least one of $T_1$ and $T_2$ is —OH.

B may be

In this case, n1 and n2 may be each independently an integer of 1 to 12, and n1 and n2 may be the same. In addition, n1 and n2 may be different integers. For example, n1 and n2 may be 2.

A reactive mesogen according to an embodiment may include a tertiary amine having at least one OH group as an anchoring group, so that the reactive mesogen may be stably combined with a base substrate or an electrode.

B may be an unsubstituted heterocycle. For example, B may be a hetero aromatic ring having 3 to 20 carbon atoms for forming a ring, or a hetero aliphatic ring having 3 to 20 carbon atoms for forming a ring.

B may be selected from the following B-1 to B-18.

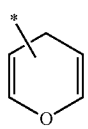

B-1

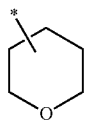

B-2

-continued

B-3 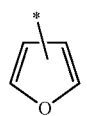

B-4 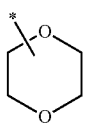

B-5 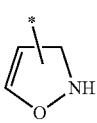

B-6 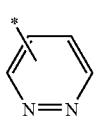

B-7 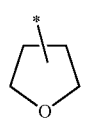

B-8 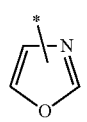

B-9 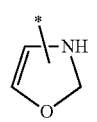

B-10 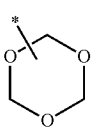

B-11 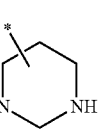

B-12 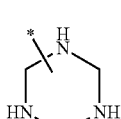

B-13 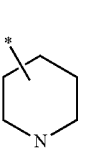

B-14 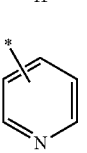

-continued

B-15 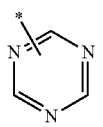

B-16 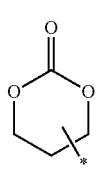

B-17 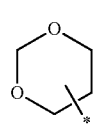

B-18 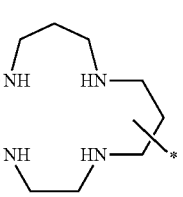

B may be a substituted or unsubstituted crown ether group. For example, B may be a crown ether group having 4 to 20 carbon atoms for forming a ring. In an embodiment, the crown ether group may form a ring using carbon and oxygen atoms. In another embodiment, the crown ether group may form a ring using a heteroatom in addition to the carbon and oxygen atoms. For example, the crown ether group may form a ring using a nitrogen atom in addition to the carbon and oxygen atoms. The crown ether group may form a ring using a plurality of nitrogen atoms. In particular, the crown ether group may include aza-12-crown-4, aza-18-crown-6, diaza-18-crown-6, etc. However, an embodiment is not limited thereto.

In addition, a substituent in a substituted crown ether group may combine with an adjacent group to form a ring. For example, the substituent of the crown ether group may be condensed to form an aliphatic hydrocarbon ring or an aromatic hydrocarbon ring. Particularly, the crown ether group may be dicyclohexano-18-crown-6, dibenzo-19-crown-6, etc. However, an embodiment is not limited thereto.

B may be selected from the following E-1 to E-13.

E-1 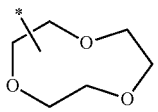

E-2 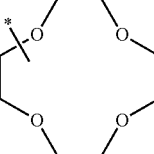

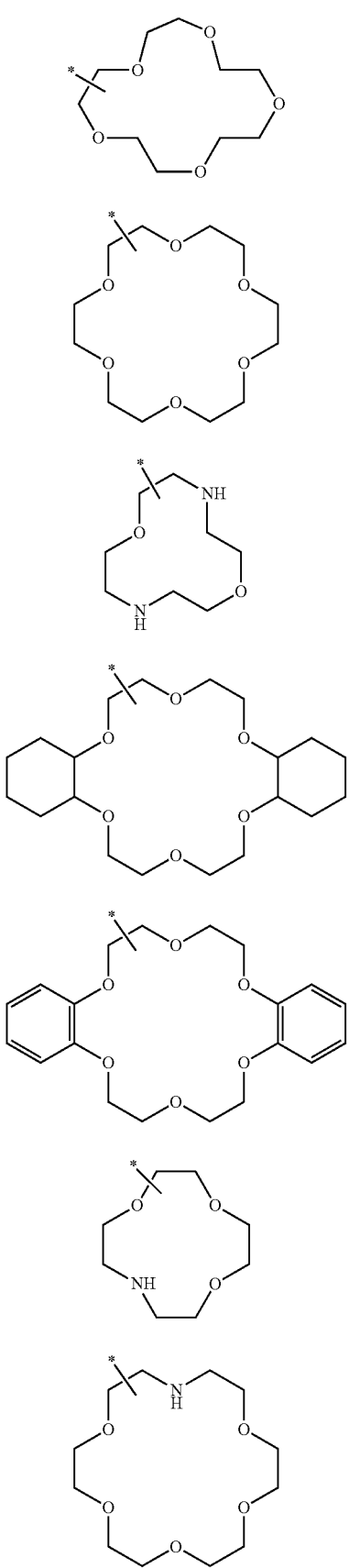
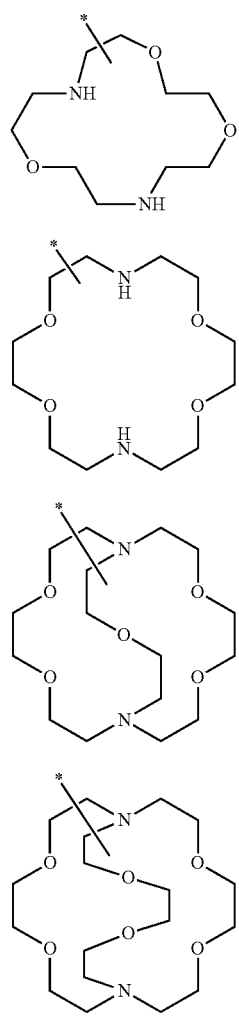
Pa may be a polymerizable group. Pa may be a polymerizable reactive group. For example, Pa may be a reactive group for a chain polymerization reaction. Particularly, Pa may be a reactive group including a —C=C— double bond, or a —C≡C— triple bond.
Pa may be one of the following P-1 to P-9.
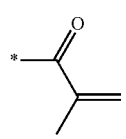

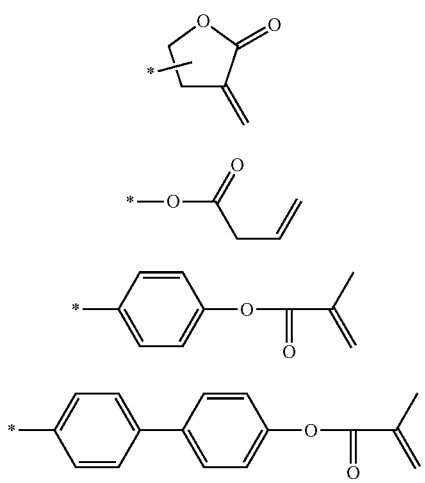

P-6

P-7

P-8

P-9

$L_1$ and $L_2$ may be each independently a direct linkage, —O—, —S—, —CO—, —COO—, —OCOO—, —O(CH$_2$)$_{k1}$—, —S(CH$_2$)$_{k1}$—, —O(CF$_2$)$_{k1}$—, —S(CF$_2$)$_{k1}$—, —(CH$_2$)$_{k1}$—, —CF$_2$CH$_2$—, —(CF$_2$)$_{k1}$, —CH=CH—, —CF=CF—, —C≡C—, —CH=CH—COO—, or —(CH$_2$)$_{k1}$—COO—(CH$_2$)$_{k2}$—O—. Here, k1 and k2 may be each independently an integer of 0 to 4.

$L_1$ and $L_2$ may be a connecting group for connecting $A_1$, $A_2$, and $A_3$, which are core groups, with each other. In addition, $L_1$ and $L_2$ may be a connecting group for connecting $A_1$, $A_2$, and $A_3$, which are core groups with a polymerizable group Pa or an anchoring group B, which are terminal groups.

Meanwhile, exemplary embodiments of $L_1$ and $L_2$ are not limited to the suggested connecting groups, and combining order may be changed. For example, —O(CH$_2$)$_{k1}$— may include —(CH$_2$)$_{k1}$O—. This may be applied to other suggested connecting groups.

$Z_1$ and $Z_2$ may be each independently a direct linkage, —O—, —S—, —CO—, —COO—, —OCOO—, —O(CH$_2$)$_{m1}$—, —S(CH$_2$)$_{m1}$—, —O(CF$_2$)$_{m1}$—, —S(CF$_2$)$_{m1}$—, —(CH$_2$)$_{m1}$—, —CF$_2$CH$_2$—, —(CF$_2$)$_{m1}$, —CH=CH—, —CF=CF—, —C≡C—, —CH=CH—COO—, —(CH$_2$)$_{m1}$—COO—(CH$_2$)$_{m2}$—O—, —CH—(S$_p$—Pa)—, —CH$_2$CH—(S$_p$—Pa)—, or —(CH—(S$_p$—Pa)—CH—(S$_p$—Pa))—. In this case, m1 and m2 may be each independently an integer of 0 to 4. $S_p$ may be a direct linkage, or a spacer group, and Pa may be a polymerizable group.

The spacer group may be a connecting group between a core group (for example, $A_1$ or $A_3$) and a polymerizable group, or a core group and an anchoring group. For example, the spacer group may be alkyl having 1 to 12 carbon atoms, or alkoxy having 1 to 12 carbon atoms. However, an embodiment is not limited thereto, and the spacer group may be, for example, —(CH$_2$)$_{i1}$—, —(CH$_2$CH$_2$O)$_{i1}$—CH$_2$CH$_2$—, —CH$_2$CH$_2$—S—CH$_2$CH$_2$—, —CH$_2$CH$_2$—NH—CH$_2$CH$_2$—, or —(SiR$_1$R$_2$—O)$_{i1}$—. In this case, $R^1$ and $R^2$ may be each independently a hydrogen atom, or alkyl having 1 to 12 carbon atoms, and it may be an integer of 1 to 12.

Meanwhile, a

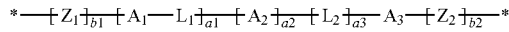

part including $A_1$, $A_2$, or $A_3$, which are core parts and $L_1$ to $L_2$, $Z_1$, and $Z_2$, which are connecting parts in a reactive mesogen of an embodiment, represented by Formula 1, may be a part for aligning liquid crystal molecules in a predetermined direction. For example, a

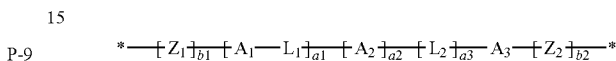

part may be a part corresponding to a vertical alignment group. Accordingly, in the case where an alignment layer of a liquid crystal display is formed using a reactive mesogen of an embodiment, represented by Formula 1, a liquid crystal compound provided may be vertically aligned.

The reactive mesogen represented by Formula 1 may be selected among the compounds represented in the following Compound Group 1.

[Compound Group 1]

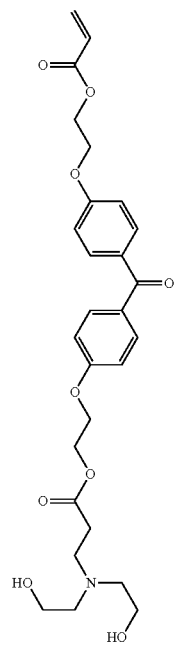

1

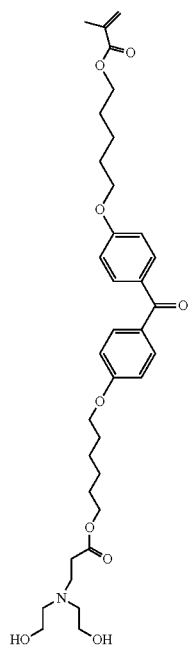

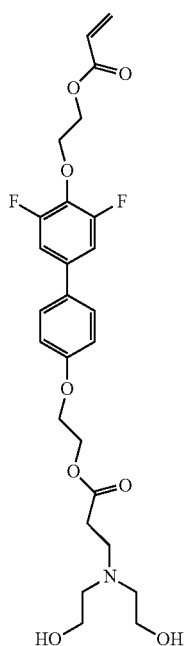

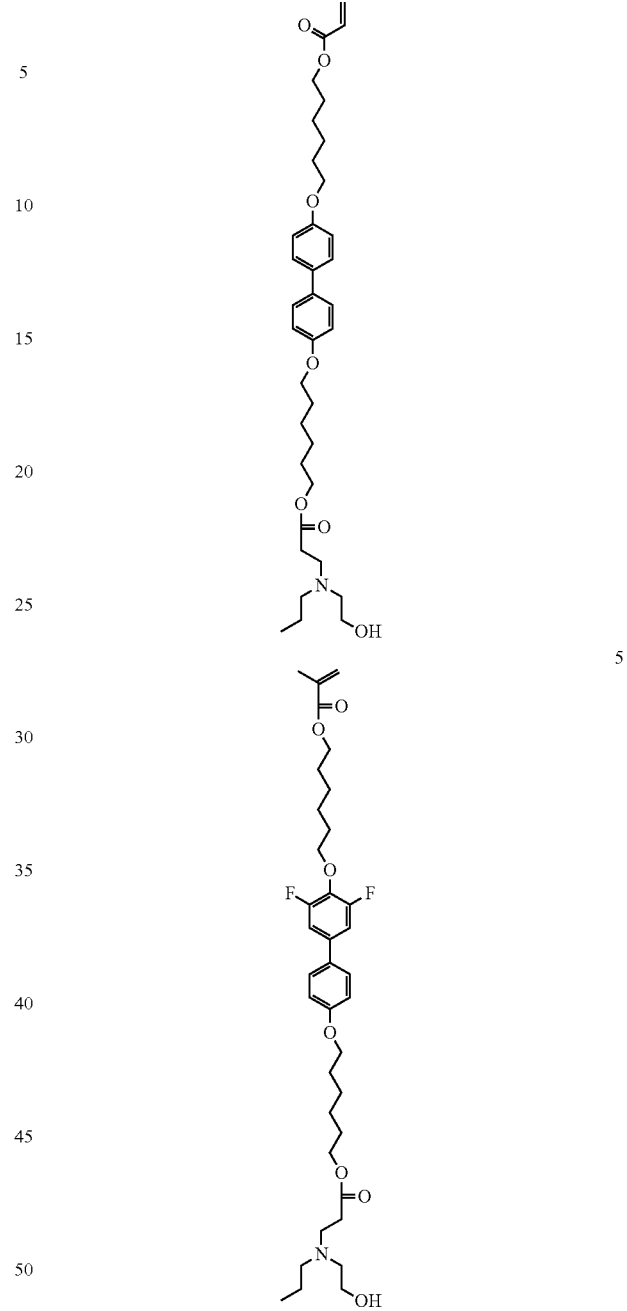

The reactive mesogens illustrated in Compound Group 1 may include a tertiary amine containing at least one —OH group as an anchoring group. Compounds 1 to 3 contain two —OH groups in an anchoring group, and Compounds 4 and 5 contain one —OH group in an anchoring group. The reactive mesogens of exemplary embodiments, represented by Compounds 1 to 5 contain at least one —OH group and may increase the combining force to a substrate on which the reactive mesogen is applied.

In addition, in Compounds 4 and 5, one —OH group and one alkyl group may be connected to a nitrogen atom in an amine group, and the combining force of the reactive mesogen to a substrate may be increased, and at the same time, the solubility of the reactive mesogen with respect to a liquid crystal compound may be improved.

Meanwhile, in Compounds 3 and 5, a phenylene group which is a core group is substituted with F which is a halogen atom. The reactive mesogen of Compound 3 or 5, in which a core group is substituted with a halogen atom may have improving effect of solubility to a liquid crystal compound when compared to an unsubstituted compound.

In addition, Compounds 1 and 2 may include benzophenone in a core part and function as an initiator, thereby producing radicals to induce a polymerization reaction of a reactive mesogen. Accordingly, the reactive mesogens of exemplary embodiments, represented by Compounds 1 and 2 may have improved producing effect of free radicals when compared to Compounds 3 to 5 and may have an increased polymerization rate of the reactive mesogen.

The reactive mesogen represented by Formula 1 may be selected from the compounds represented in the following Compound Group 2. In the particular embodiments shown in Compound Group 2, the reactive mesogen may include an unsubstituted heterocycle at an anchoring group.

[Compound Group 2]

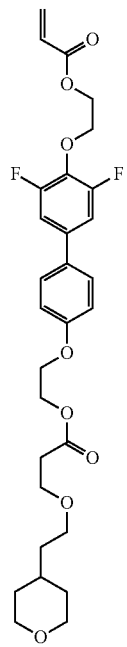
6

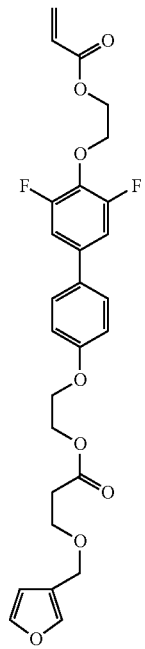
7

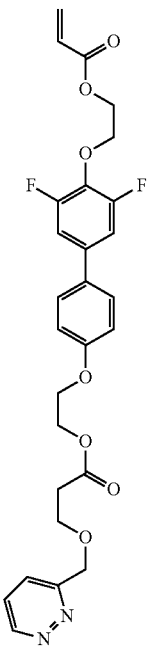
8

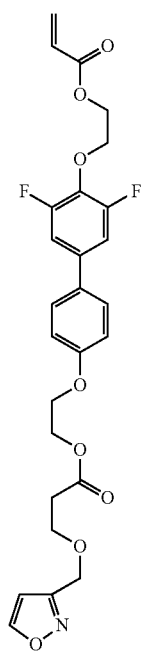
9
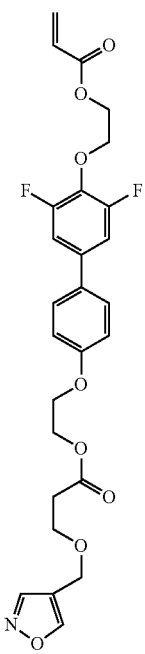
5
10
15
20
25
30
In addition, the reactive mesogen represented by Formula 1 may be selected from the compounds represented in the following Compound Group 3. In the particular embodiments shown in Compound Group 3, the reactive mesogen may include a substituted or unsubstituted crown ether group at an anchoring group.
[Compound Group 3]
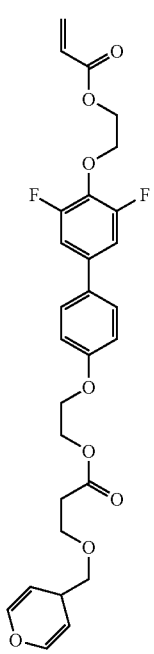
10
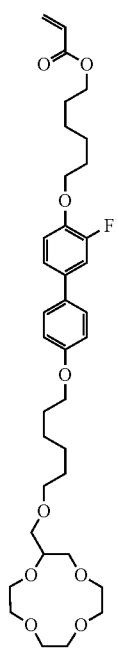
12

-continued

13

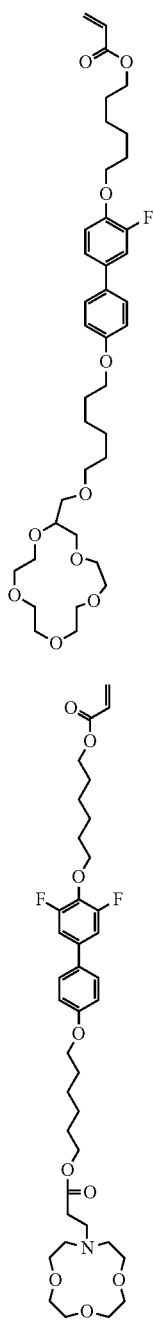

14

Compounds 12 to 14 in Compound Group 3 include a crown ether group at the terminal and may increase the combining energy of the reactive mesogen of an embodiment to a supplied substrate.

However, particular embodiments shown in Compound Groups 1, 2, and 3 are only exemplary embodiments of the reactive mesogen, and the reactive mesogen represented by Formula 1 is not limited to the compounds illustrated in Compound Groups 1, 2, and 3.

The reactive mesogen according to an embodiment may be represented by the following Formula 2.

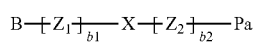

[Formula 2]

In Formula 2, X in the core part may be a part functioning as an initiator. B may be an anchoring group, and Pa may be a polymerizable group. In addition, b1 and b2 may be each independently an integer of 0 to 6.

In Formula 2, X may be one of the following X-1 to X-17.

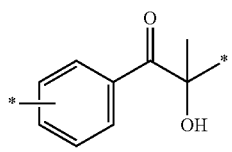
X-1

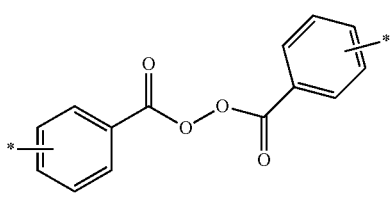
X-2

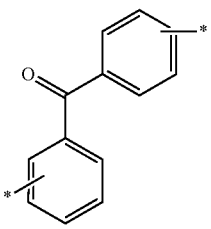
X-3

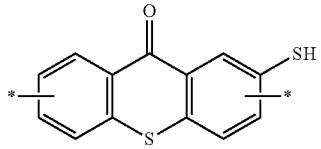
X-4

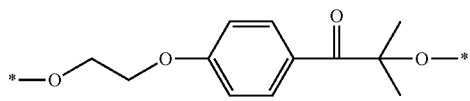
X-5

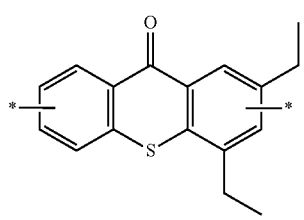
X-6

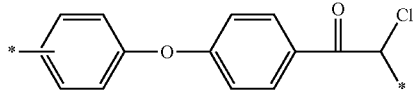
X-7

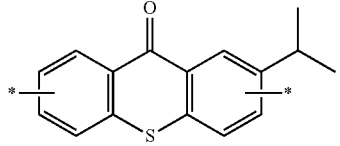
X-8

X includes a carbonyl group and thus, may play the role of an initiator which produces radicals to cause a polymerization reaction of reactive mesogens. In the case where a reactive mesogen of an embodiment, represented by Formula 2 is used, a polymerization reaction rate of the reactive mesogen may increase, thereby finally improving a polymerization degree of the reactive mesogen.

Meanwhile, B, Pa, $Z_1$, and $Z_2$ in Formula 2 are the same as defined in Formula 1. The same explanation on B, Pa, $Z_1$, and $Z_2$ in Formula 1 may be applied for B, Pa, $Z_1$, and $Z_2$ in Formula 2.

For example, B in Formula 2 may be selected from the following B-1 to B-20, and E-1 to E-13 as an anchoring group.

-continued
B-7 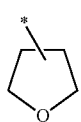
B-8 
B-9 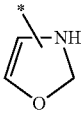
B-10 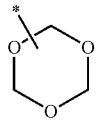
B-11 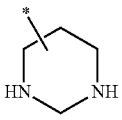
B-12 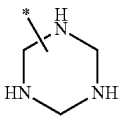
B-13 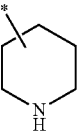
B-14 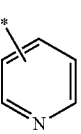
B-15 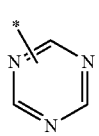
B-16 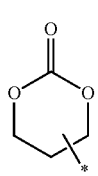
B-17 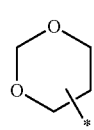
-continued
B-18 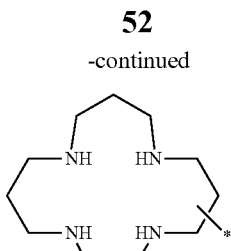
B-19 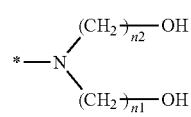
B-20 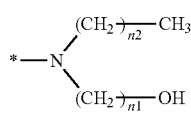
E-1 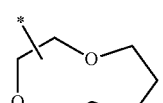
E-2 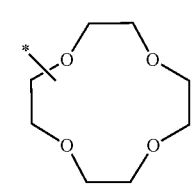
E-3 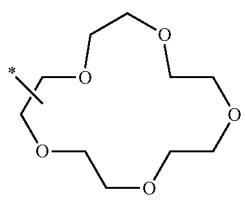
E-4 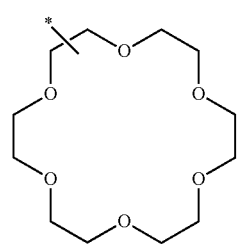
E-5 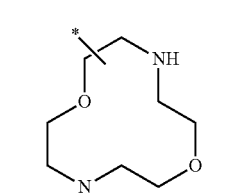
E-6 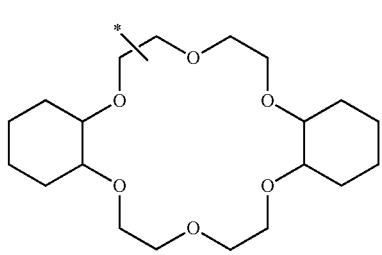

E-7
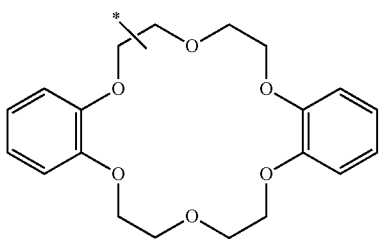

E-8
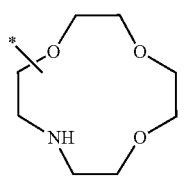

E-9
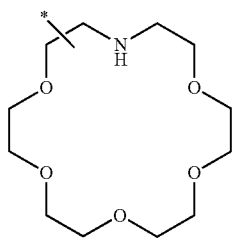

E-10
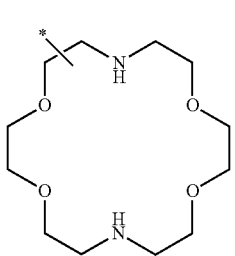

E-11
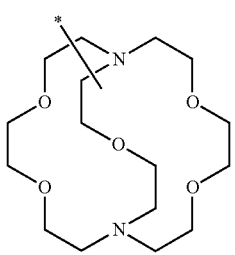

E-12
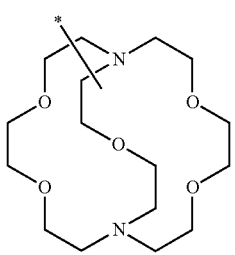

E-13
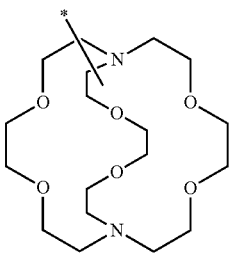

In addition, Pa is a polymerizable group and may be selected from the following P-1 to P-9.

P-1
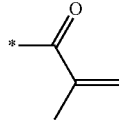

P-2
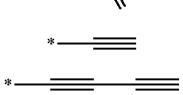

P-3
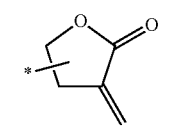

P-4
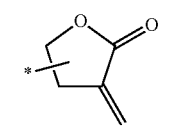

P-5
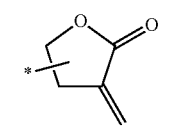

P-6
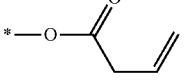

P-7
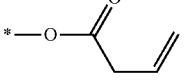

P-8
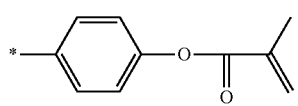

P-9
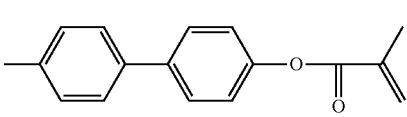

The reactive mesogen of an embodiment, represented by Formula 1 or 2 may be used for the formation of an alignment layer in a liquid crystal display which will be explained below. For example, the reactive mesogen of an embodiment may be supplied together with a liquid crystal compound to a liquid crystal layer of a liquid crystal display to form an alignment layer. Alternatively, the reactive mesogen of an embodiment may be supplied together with an alignment agent to form an alignment layer. In this case, alignment agents may be polyimides, polyamic acids, polyamides, polyamic imides, polyesters, polyethylenes, polyurethanes, or monomers, dimmers, or oligomers of a polymer such as polystyrene, or a mixture thereof. The reactive mesogen of an embodiment may be used for directly forming an alignment layer on an electrode on which an alignment layer is not formed.

In this case, the alignment layer formed by the reactive mesogen according to an embodiment may be formed on at least one substrate among an upper substrate or a lower substrate of a liquid crystal display.

In an embodiment, a liquid crystal composition including a liquid crystal compound and a first reactive mesogen represented by Formula 3 may be provided.

[Formula 3]

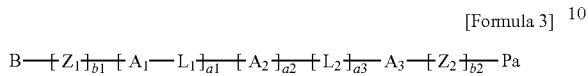

In Formula 3, $A_1$, $A_2$, and $A_3$ may be each independently a substituted or unsubstituted and divalent hydrocarbon ring, or a substituted or unsubstituted divalent heterocycle. a1, b1, and b2 may be each independently an integer of 0 to 6, and a2 and a3 may be each independently 0 or 1.

In Formula 3, B may be an anchoring group, Pa may be a polymerizable group, and

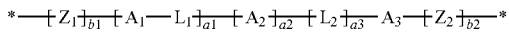

may be a vertical alignment group.

Meanwhile, B, Pa, $L_1$ to $L_2$, and $Z_1$ to $Z_2$ in Formula 3 are the same as defined in Formula 1. The same explanation on B, Pa, $L_1$ to $L_2$, and $Z_1$ and $Z_2$ in Formula 1 may be applied to B, Pa, $L_1$ to $L_2$, and $Z_1$ and $Z_2$ in Formula 3.

The first reactive mesogen represented by Formula 3 may form an alignment layer for vertically aligning liquid crystal molecules which are liquid crystal compounds with respect to a substrate. For example, an alignment layer formed by the first reactive mesogen may be a vertical alignment inducing layer for vertically aligning liquid crystal molecules with respect to a substrate.

The liquid crystal compound may include a nematic liquid crystal compound. The liquid crystal compound may represent one kind of liquid crystal molecules or may include a plurality of different kinds of liquid crystal molecules.

For example, a liquid crystal compound may include at least one of the following L-1 to L-10.

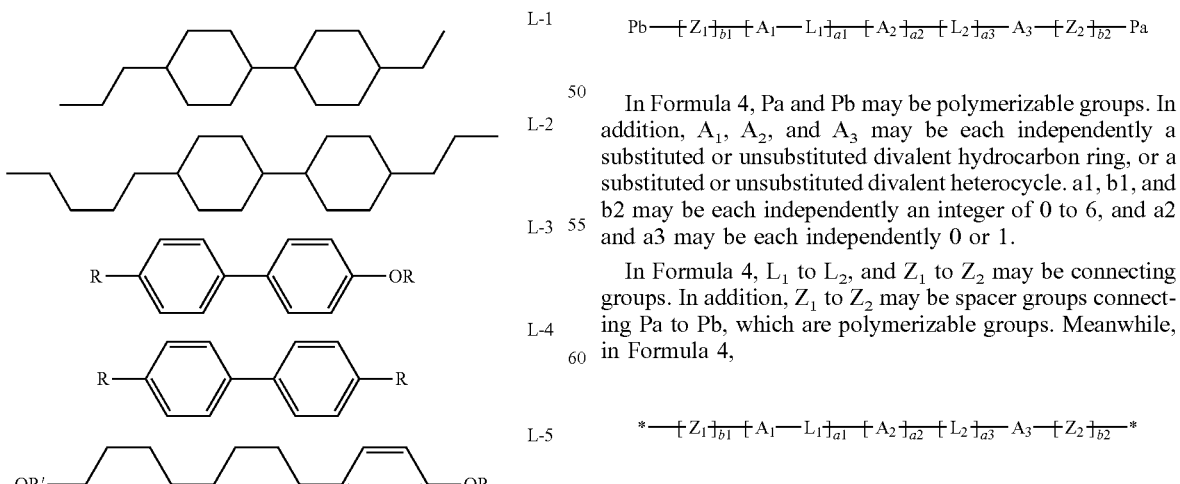

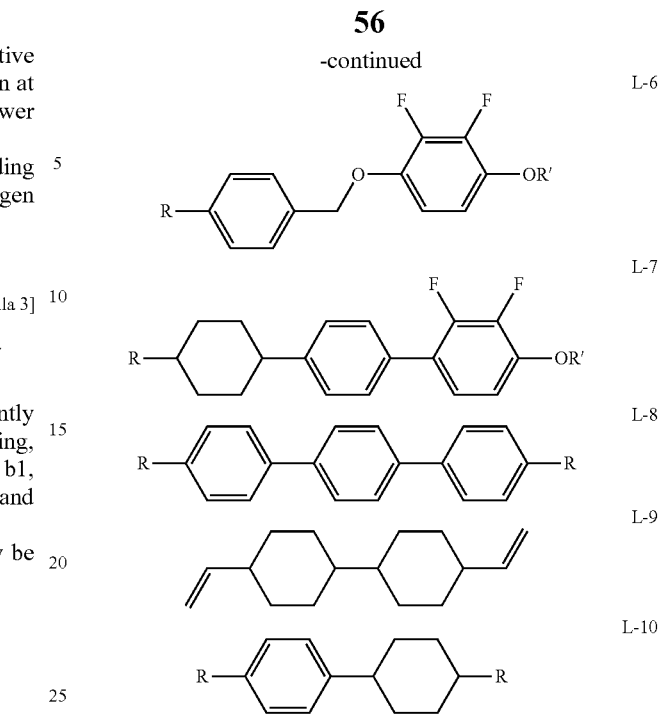

In a liquid crystal composition according to an embodiment, the first reactive mesogen may be included in an amount ratio of about 0.1 parts by weight to about 2 parts by weight on the basis of about 100 parts by weight of a liquid crystal compound. In the case where the amount of the first reactive mesogen is less than about 0.1 parts by weight, the formation of an alignment layer for aligning liquid crystal compounds may not be easy. In addition, in the case where the amount of the first reactive mesogen is greater than about 2 parts by weight, the solubility of the first reactive mesogen with respect to a liquid crystal compound may decrease.

The reactive mesogen according to an embodiment may further include a second reactive mesogen represented by Formula 4 in addition to the first reactive mesogen represented by Formula 3.

[Formula 4]

Pb—$\{Z_1\}_{b1}$—$\{A_1$—$L_1\}_{a1}$—$\{A_2\}_{a2}$—$\{L_2\}_{a3}$—$A_3$—$\{Z_2\}_{b2}$—Pa

In Formula 4, Pa and Pb may be polymerizable groups. In addition, $A_1$, $A_2$, and $A_3$ may be each independently a substituted or unsubstituted divalent hydrocarbon ring, or a substituted or unsubstituted divalent heterocycle. a1, b1, and b2 may be each independently an integer of 0 to 6, and a2 and a3 may be each independently 0 or 1.

In Formula 4, $L_1$ to $L_2$, and $Z_1$ to $Z_2$ may be connecting groups. In addition, $Z_1$ to $Z_2$ may be spacer groups connecting Pa to Pb, which are polymerizable groups. Meanwhile, in Formula 4,

*—$\{Z_1\}_{b1}$—$\{A_1$—$L_1\}_{a1}$—$\{A_2\}_{a2}$—$\{L_2\}_{a3}$—$A_3$—$\{Z_2\}_{b2}$—* may be a vertical alignment group for aligning a liquid crystal compound.

In Formula 4, $L_1$ to $L_2$, and $Z_1$ to $Z_2$ are the same as in Formula 1. The same explanation on $L_1$ to $L_2$, and $Z_1$ to $Z_2$ in Formula 1 may be applied for $L_1$ to $L_2$, and $Z_1$ to $Z_2$ in Formula 4.

In the second reactive mesogen represented by Formula 4, Pa and Pb may be each independently one polymerizable group among P-1 to P-10. In P-10, p may be an integer between 1 and 20, included. However, a case where both Pa and Pb are P-10 is excluded. That is, in the case where Pa is P-10, Pb may be any one selected from P-1 to P-9, and in the case where Pb is P-10, Pa may be any one selected from P-1 to P-9.

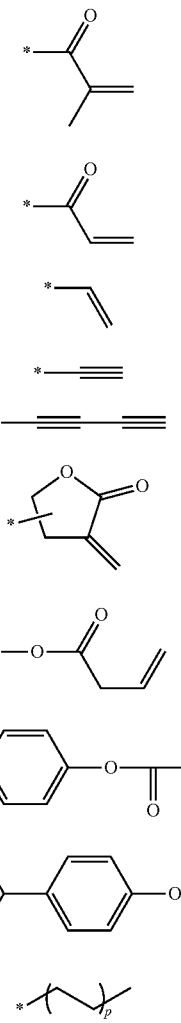

That is, both terminals of the second reactive mesogen included in a liquid crystal composition according to an embodiment may have polymerizable groups. In addition, in the case where one of Pa and Pb is

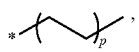, only one terminal may have a polymerizable group.

A liquid crystal composition according to an embodiment may further include a third reactive mesogen represented by the following Formula 5.

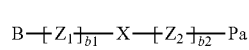 [Formula 5]

In Formula 5, X may be any one of the following X-1 to X-17.

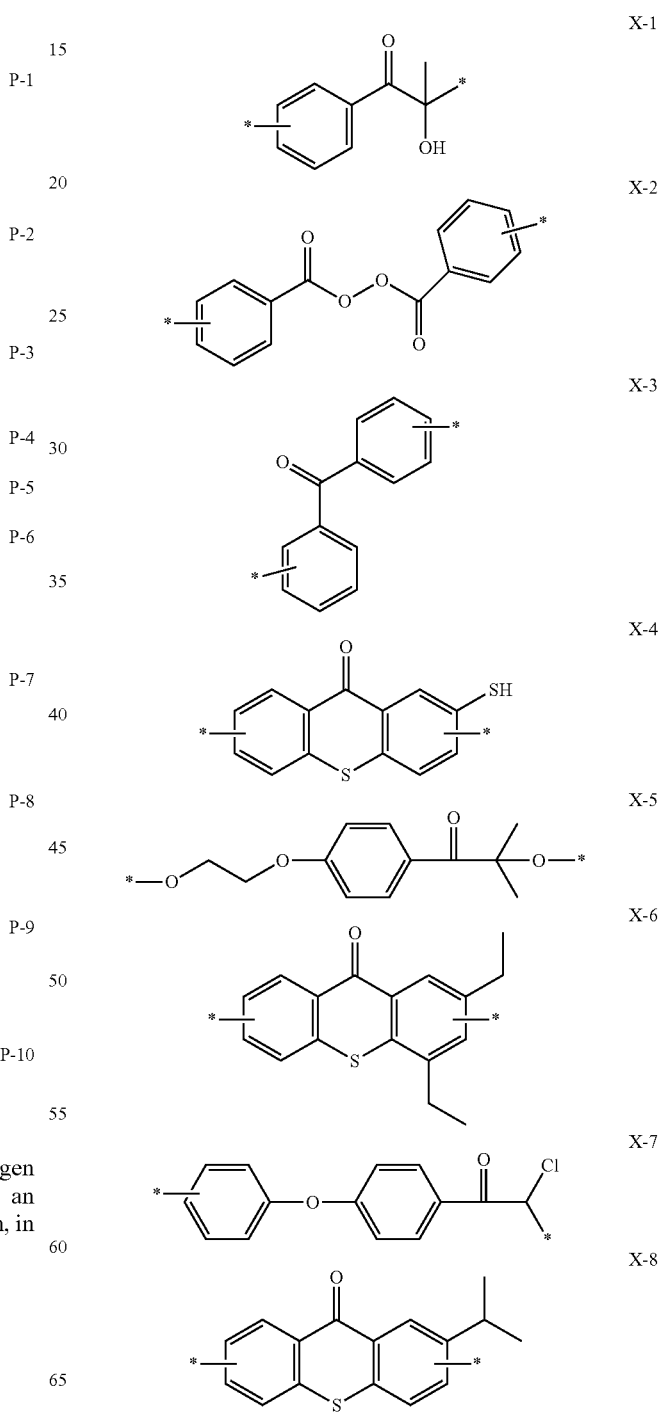

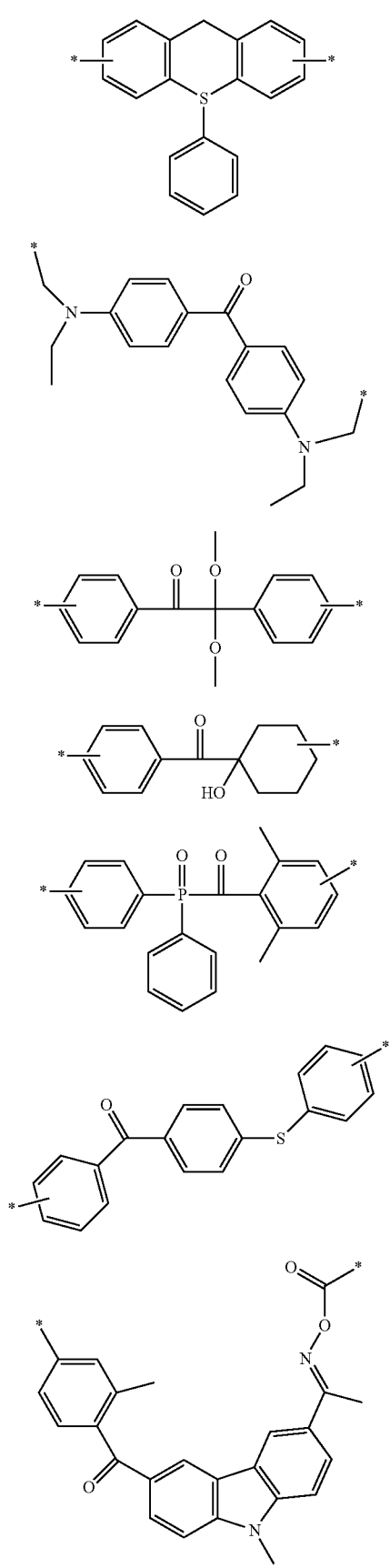
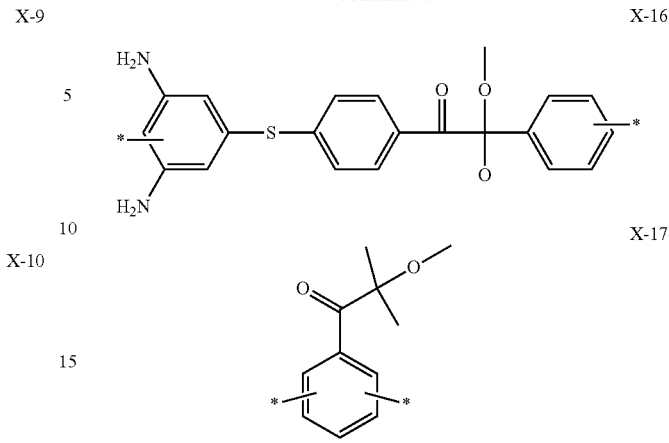

Meanwhile, in a reactive mesogen according to an embodiment, represented by Formula 5, $Z_1$, $Z_2$, B, Pa, b1, and b2 are the same as defined in Formula 1. The same explanation on $Z_1$, $Z_2$, B, Pa, b1, and b2 in Formula 1 may be applied for $Z_1$, $Z_2$, B, Pa, b1, and b2 in Formula 5.

The liquid crystal composition according to an embodiment may further include a third reactive mesogen represented by Formula 5 to increase the polymerization degree of the reactive mesogen. In addition, a liquid crystal composition including a third reactive mesogen according to an embodiment is provided, and an alignment layer of a liquid crystal display may tilt a liquid crystal compound provided on the alignment layer at a pre-determined angle. That is, an alignment layer formed by providing a liquid crystal composition including a third reactive mesogen may lead an increased pre-tilt angle of a liquid crystal compound when compared to an alignment layer formed by providing a liquid crystal composition not including a third reactive mesogen.

The third reactive mesogen may be included in an amount ratio of about 1 part by weight to about 10 parts by weight on the basis of about 100 parts by weight of the sum of the first reactive mesogen and the second reactive mesogen. In the case where the amount of the third reactive mesogen is less than about 1 part by weight, a radical producing part which may function as an initiator may be insufficient, and a polymerization rate of the reactive mesogen may not be improved. In addition, in the case where the amount of the third reactive mesogen is greater than about 10 parts by weight, an excessive polymerization reaction of the reactive mesogen may occur. In this case, an alignment layer formed by providing a liquid crystal composition by the excessive polymerization reaction may not satisfy physical properties required for aligning a liquid crystal compound. For example, in the case where greater than about 10 parts by weight of a third reactive mesogen is included in a liquid crystal composition, the pre-tilt angle of a liquid crystal compound aligned on an alignment layer may deviate from required conditions.

Hereinafter, a liquid crystal display manufactured by providing a reactive mesogen according to an embodiment or a liquid crystal composition according to an embodiment will be explained.

FIG. 1 is a diagram schematically illustrating a cross-sectional view of a liquid crystal display according to an embodiment. The liquid crystal display shown in FIG. 1 may include an alignment layer formed using a reactive mesogen.

Referring to FIG. 1, a liquid crystal display DD may include a first substrate SUB1, a second substrate SUB2, and a liquid crystal layer LCL provided between the first substrate SUB1 and the second substrate SUB2. On the first substrate SUB1, a first alignment layer ALN1 may be disposed, and on the second substrate SUB2, a second alignment layer ALN2 may be disposed. The second alignment layer ALN2 may be disposed on one side of the second substrate SUB2 which is opposite to the first substrate SUB1. Between the first alignment layer ALN1 and the second alignment layer ALN2, the liquid crystal layer LCL may be disposed.

A liquid crystal compound LC aligned between the first alignment layer ALN1 and the second alignment layer ALN2 may be vertically aligned with respect to the first substrate SUB1 and the second substrate SUB2. In addition, the liquid crystal compound LC may be aligned at a predetermined angle with respect to the first substrate SUB1 and the second substrate SUB2.

At least one of the first alignment layer ALN1 and the second alignment layer ALN2 may be an alignment layer formed using the above-described reactive mesogen according to an embodiment. That is, in the liquid crystal display DD shown in FIG. 1 according to an embodiment, the alignment layers ALN1 and ALN2 may be formed by the reactive mesogen according to an embodiment without providing a polyimide alignment layer, etc. For example, one of the first alignment layer ALN1 and the second alignment layer ALN2 may be an alignment layer formed using the above-described reactive mesogen according to an embodiment, and the remaining one may be an alignment layer formed as a polyimide alignment layer. Particularly, the first alignment layer ALN1 may be formed by the reactive mesogen according to an embodiment, and the second alignment layer ALN2 may be an alignment layer formed as a polyimide alignment layer. Alternatively, the first alignment layer ALN1 may be an alignment layer formed as a polyimide alignment layer, and the second alignment layer ALN2 may be formed by the reactive mesogen according to an embodiment. In addition, both the first alignment layer ALN1 and the second alignment layer ALN2 may be formed by the reactive mesogen according to an embodiment.

Between the first substrate SUB1 and the second substrate SUB2 of the liquid crystal display DD, a sealing layer SL may be provided. The sealing layer SL may be disposed at the edge position of the first substrate SUB1 and the second substrate SUB2 to combine two opposite substrates SUB1 and SUB2 so as to protect the liquid crystal layer LCL.

Figure 2:
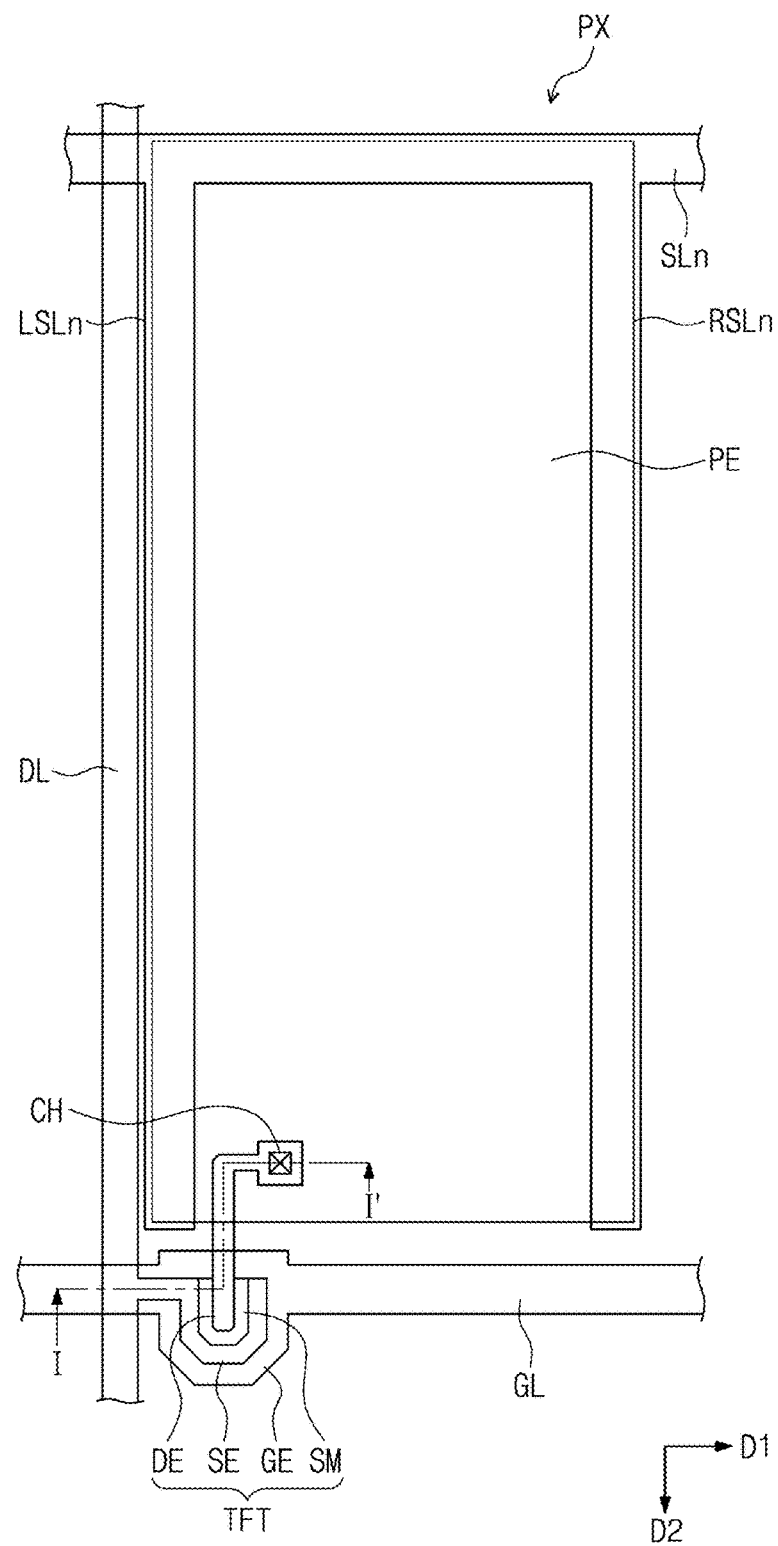
FIG. 2 is a plan view schematically illustrating one pixel included in a liquid crystal display including an alignment layer formed using a reactive mesogen according to an embodiment.
Figure 3:
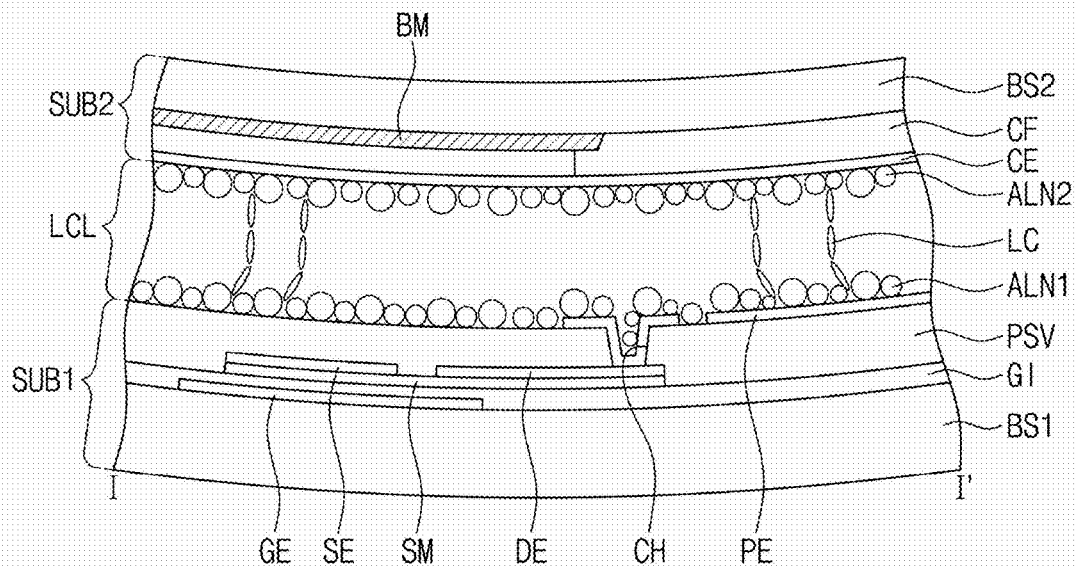
FIG. 3 is a cross-sectional view corresponding to line I-I' in FIG. 2.

FIG. 2 is a plan view illustrating a part of a pixel in a liquid crystal display, and FIG. 3 is a cross-sectional view of a liquid crystal display corresponding to line I-I' in FIG. 2. FIGS. 2 and 3 may be exaggerated via extension or contraction for the convenience of explanation.

A liquid crystal display shown in FIG. 3 according to an embodiment may be a curved liquid crystal display. That is, the liquid crystal display shown in FIG. 3 may be bent with a pre-determined curvature. The curved liquid crystal display may be a flexible one or a rigid one. The liquid crystal display shown in FIG. 3 may be dented when seen from the second substrate SUB2 which is an upper substrate. However, an embodiment is not limited thereto and the liquid crystal display may be convexly curved when seen from the second substrate SUB2.

For the convenience of explanation, one pixel PX connected with one gate line among gate lines GL and one data line among data lines DL is shown in FIGS. 2 and 3. However, an embodiment is not limited thereto. For example, one gate line and one data line may be connected with a plurality of pixels, or a plurality of gate lines and a plurality of data lines may be connected with one pixel.

The first substrate SUB1 may include a first base substrate BS1 and a circuit layer formed on the first base substrate BS1. The first base substrate BS1 may be a polymer substrate, a plastic substrate, a glass substrate, a quartz substrate, etc. The first base substrate BS1 may be a transparent insulating substrate. The first base substrate BS1 may be flexible or rigid.

Referring to the drawings in FIGS. 2 and 3, the gate lines GL are extended in a first direction D1. The gate lines GL may be formed on the first base substrate BS1. The data lines DL may be extended in a second direction D2 which crosses the gate lines GL in the first direction D1.

Each of the pixels PX includes a thin film transistor TFT, a pixel electrode PE connected with the thin film transistor TFT, and a storage electrode part. The thin film transistor TFT includes a gate electrode GE, a gate insulating layer GI, a semiconductor pattern SM, a source electrode SE, and a drain electrode DE. The storage electrode part may further include a storage line SLn extended in the first direction D1, and a first branched electrode LSLn and a second branched electrode RSLn, which are branched from the storage line SLn and extended in the second direction D2.

The gate electrode GE protrudes from the gate lines GL or provided in a partial region of the gate lines GL. The gate electrode GE may be formed using a metal. The gate electrode GE may be formed using nickel, chromium, molybdenum, aluminum, titanium, copper, tungsten, or an alloy including the same. The gate electrode GE may be formed as a single layer or a multilayer using a metal. For example, the gate electrode GE may be a triple layer obtained by laminating molybdenum, aluminum, and molybdenum one by one, a double layer obtained by laminating titanium and copper one by one, or a single layer formed using an alloy of titanium and copper.

The semiconductor pattern SM is provided on the gate insulating layer GI. The semiconductor pattern SM is provided on the gate electrode GE with the gate insulating layer GI disposed therebetween. The semiconductor pattern SM is partially overlapped with the gate electrode GE. The semiconductor pattern SM includes an active pattern (not shown) provided on the gate insulating layer GI and an ohmic contact layer (not shown) formed on the active pattern. The active pattern may be formed using an amorphous silicon thin film, and the ohmic contact layer may be formed using an n+ amorphous silicon thin film. The ohmic contact layer makes an ohmic contact between the active pattern, and the source electrode SE and the drain electrode DE, respectively.

The source electrode SE is branched from the data lines DL and provided. The source electrode SE is formed on the ohmic contact layer and is partially overlapped with the gate electrode GE.

The drain electrode DE is separated from the source electrode SE with the semiconductor pattern SM therebetween. The drain electrode DE is formed on the ohmic contact layer and is partially overlapped with the gate electrode GE.

The source electrode SE and the drain electrode DE may be formed using nickel, chromium, molybdenum, aluminum, titanium, copper, tungsten, or an alloy including the same. The source electrode SE and the drain electrode DE may be formed as a single layer or a multilayer using a metal. For example, the source electrode SE and the drain electrode DE may be a double layer obtained by laminating titanium and copper one by one, or a single layer formed using an alloy of titanium and copper.

Accordingly, the upper side of the active pattern between the source electrode SE and the drain electrode DE is exposed and becomes a channel part forming a conductive channel between the source electrode SE and the drain electrode DE depending on whether a voltage is applied to the gate electrode GE or not. The source electrode SE and the drain electrode DE are partially overlapped with the semiconductor pattern SM in a region excluding the channel part separately formed between the source electrode SE and the drain electrode DE.

The pixel electrode PE is connected with the drain electrode DE with a passivation layer PSV therebetween. The pixel electrode PE is partially overlapped with the storage line SLn, a first branched electrode LSLn, and a second branched electrode RSLn to form a storage capacitor.

The passivation layer PSV covers the source electrode SE, the drain electrode DE, the channel part, and the gate insulating layer GI and has a contact hole CH exposing a portion of the drain electrode DE. The passivation layer PSV may include, for example, silicon nitride, or silicon oxide.

The pixel electrode PE is connected with the drain electrode DE via a contact hole CH formed in the passivation layer PSV. The pixel electrode PE is formed using a transparent conductive material. Particularly, the pixel electrode PE is formed using a transparent conductive oxide. The transparent conductive oxide may be indium tin oxide (ITO), indium zinc oxide (IZO), indium tin zinc oxide (ITZO), etc.

In addition, the first alignment layer ALN1 may be provided on the pixel electrode PE and the passivation layer PSV.

Meanwhile, the liquid crystal display shown in FIG. 3 includes the first substrate SUB1, the second substrate SUB2 opposite to the first substrate SUB1, and the liquid crystal layer LCL provided between the first substrate SUB1 and the second substrate SUB2. The gate insulating layer GI is provided on the entire surface of the first base substrate BS1 and covers the gate lines GL. The alignment layers ALN1 and ALN2 may be formed on the first substrate SUB1 and the second substrate SUB2. The alignment layers ALN1 and ALN2 may cause the alignment of the liquid crystal compound LC provided between the first substrate SUB1 and the second substrate SUB2 at a pre-tilt angle.

The second substrate SUB2 includes a second base substrate BS2, a color filter CF, a black matrix BM, and a common electrode CE. The second base substrate BS2 may be a polymer substrate, a plastic substrate, a glass substrate, a quartz substrate, etc. The second base substrate BS2 may be a transparent insulating substrate. The second base substrate BS2 may be flexible or rigid.

The color filter CF is provided on the second base substrate BS2 and provides colors. In an embodiment of the inventive concept, the color filter CF is included in the second substrate SUB2. However, an embodiment is not limited thereto, and the color filter CF may be included in the first substrate SUB1.

The black matrix BM is provided so as to correspond to a light shielding region of the first substrate SUB1. The light shielding region may be defined as a region in which data lines DL, a thin film transistor TFT, and gate lines GL are formed. The black matrix BM is formed in the light shielding region and shields light leakage. In an embodiment of the inventive concept, the black matrix BM is included in the second substrate SUB2. However, an embodiment is not limited thereto, and the black matrix BM may be included in the first substrate SUB1. Even though not shown, an insulating layer (not shown) may be formed on the color filter CF and the black matrix BM.

The common electrode CE is provided on the second base substrate BS2 and forms an electric field with the pixel electrode PE, thereby driving the liquid crystal layer LCL. In an embodiment of the inventive concept, the common electrode CE is included in the second substrate SUB2. However, an embodiment is not limited thereto, and the common electrode CE may be included in the first substrate SUB1. The common electrode CE may be formed using a transparent conductive material. The common electrode CE may be formed using a conductive metal oxide such as ITO, IZO, ITZO, etc. On the common electrode CE of the second base substrate BS2, a second alignment layer ALN2 may be disposed.

A liquid crystal layer LCL including the liquid crystal compound LC is provided between the first substrate SUB1 and the second substrate SUB2. The liquid crystal layer LCL in which a liquid crystal compound LC having dielectric anisotropy is aligned may be provided. Commonly used liquid crystal molecules may be used as the liquid crystal compound LC, without specific limitation, for example, an alkenyl liquid crystal compound, or an alkoxy liquid crystal compound may be used. The liquid crystal compound LC used in an embodiment may have negative dielectric anisotropy, but may have positive dielectric anisotropy, without limitation.

The alignment layers ALN1 and ALN2 may be formed using spherical or elliptical particles having a random size. The spherical or elliptical particles having a random size may be particles obtained by the polymerization reaction of a reactive mesogen. For example, the alignment layers ALN1 and ALN2 may be layers formed by laminating the particles which have a random size and are formed by the reactive mesogen.

Figure 4:
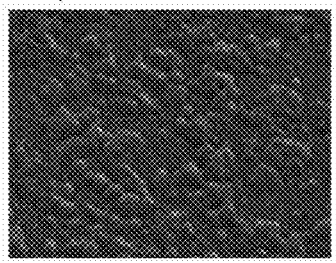
FIG. 4 illustrates SEM images on the surfaces of alignment layers formed by providing liquid crystal compositions according to exemplary embodiments.
Figure 4:
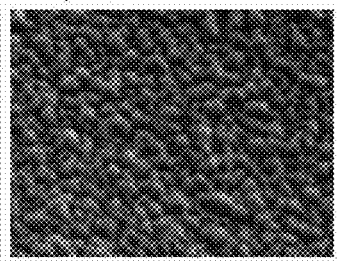
Figure 4:
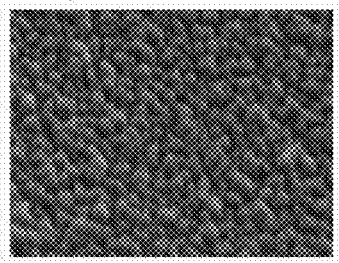

FIG. 4 illustrates scanning electron microscope (SEM) images on the surfaces of an alignment layer ALN1 or ALN2 formed by a reactive mesogen. The surface images observed in FIG. 4 illustrate alignment layers formed by including a reactive mesogen according to an embodiment and a reactive mesogen represented by the following Formula 6.

[Formula 6]

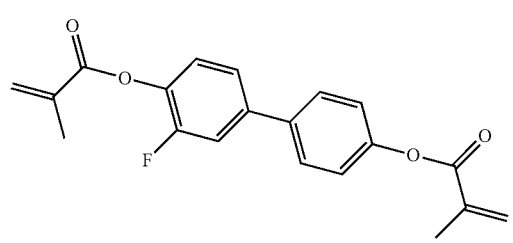

Table 1 illustrates reactive mesogens according to exemplary embodiments used in Compound-I, Compound-II, and Compound-III in the SEM images. Compound-I corresponds to an alignment layer formed by including Compound 1 disclosed in Compound Group 1, Compound-II corresponds to an alignment layer formed by including Compound 4 disclosed in Compound Group 1, and Compound-III corresponds to an alignment layer formed by including Compound 6 disclosed in Compound Group 2.

TABLE 1

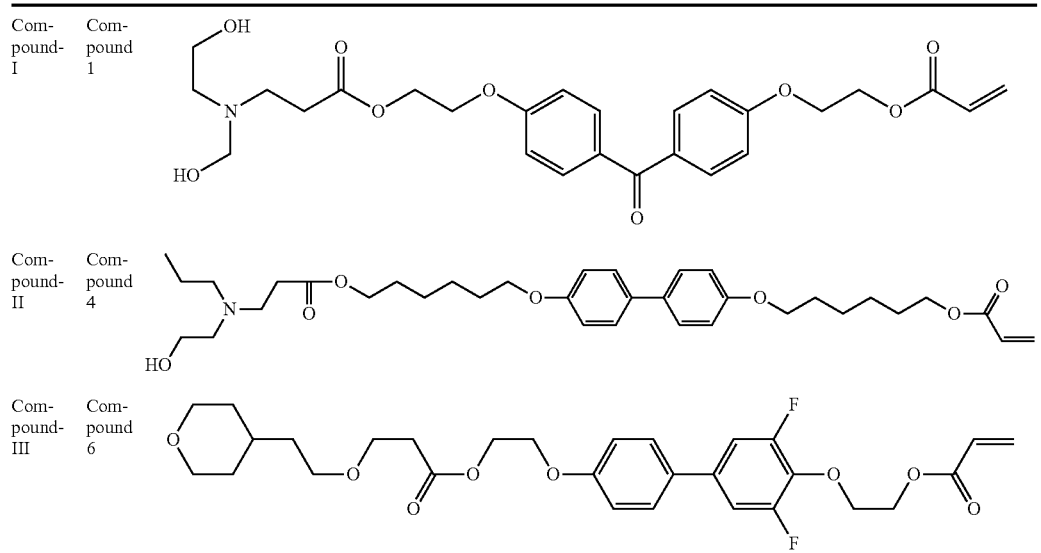

| Compound-I | Compound 1 | |
| Compound-II | Compound 4 | |
| Compound-III | Compound 6 | |

As schematically shown in FIG. 3, the alignment layer formed by the reactive mesogen is formed by laminating the particles with a random size, and random protrusions are formed on the surface of the alignment layer as shown in SEM images in FIG. 4.

An average particle diameter of the random particles formed by the reactive mesogen according to an embodiment may be from about 1 nm to less than about 30 nm. In this case, the thickness of the alignment layers ALN1 and ALN2 may be from about 30 nm to about 40 nm. However, an embodiment is not limited thereto.

In addition, in an embodiment of the liquid crystal display shown in FIG. 3, the pre-tilt angle of the liquid crystal compound LC disposed on the first alignment layer ALN1 and the pre-tilt angle of the liquid crystal compound LC disposed on the second alignment layer ALN2 may be different. For example, the liquid crystal compound LC disposed adjacent to and on the second alignment layer ALN2 may be vertically aligned with respect to the second substrate SUB2. In comparison, the liquid crystal compound LC disposed adjacent to and on the first alignment layer ALN1 may be disposed with a predetermined tilted angle with respect to the first substrate SUB1.

That is, in the curved liquid crystal display shown in FIG. 3, the alignment stability of the liquid crystal compound in the liquid crystal layer LCL may be improved, and texture defects of the liquid crystal display may be improved by controlling the pre-tilt angle of the liquid crystal compound LC disposed on the first alignment layer ALN1 and the pre-tilt angle of the liquid crystal compound LC disposed on the second alignment layer ALN2 differently. That is, the display quality of a liquid crystal display may be improved by forming an alignment layer by providing a liquid crystal composition including the reactive mesogen according to an embodiment.

Meanwhile, the liquid crystal display shown in FIGS. 1 to 3 may be a super vertical alignment (SVA) mode liquid crystal display. However, an embodiment is not limited thereto, and another type of a vertical alignment mode or in-plane switching mode liquid crystal display may be used.

The reactive mesogen of an embodiment may be used in the liquid crystal display of FIGS. 1 to 3 in addition to various types of liquid crystal displays requiring a liquid crystal alignment layer. For example, the reactive mesogen according to an embodiment and a liquid crystal display including the same may be used in a photoluminescent liquid crystal display (PL-LCD). The PL-LCD may include a color conversion member formed by including phosphors or quantum dots.

Figure 5:
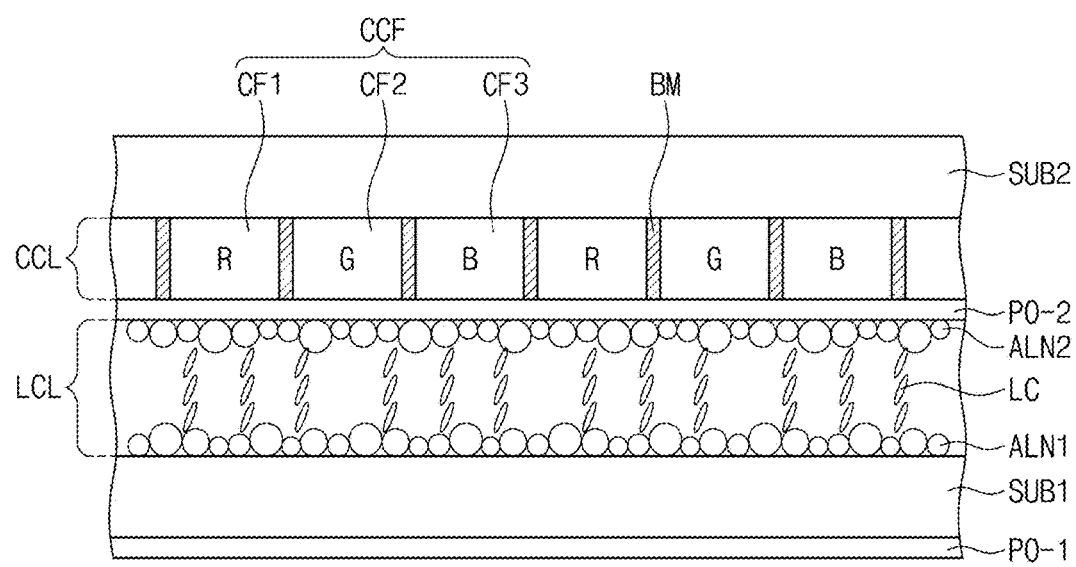
FIG. 5 is a cross-sectional view of a liquid crystal display including an alignment layer formed using a reactive mesogen according to an embodiment.

FIG. 5 is a cross-sectional view of a PL-LCD. The PL-LCD may include a first substrate SUB1, a second substrate SUB2 opposite to the first substrate SUB1, a liquid crystal layer LCL between the first substrate SUB1 and the second substrate SUB2, and a color conversion member CCL.

The liquid crystal layer LCL may include alignment layers ALN1 and ALN2 formed using the reactive mesogen of an embodiment and a liquid crystal compound LC aligned between the alignment layers ALN1 and ALN2. The liquid crystal compound LC between the alignment layers ALN1 and ALN2 may be vertically aligned with respect to the substrates SUB1 and SUB2 or aligned with a pre-determined pre-tilt angle.

Meanwhile, the same explanation on the first alignment layer ALN1, the second alignment layer ALN2, and the liquid crystal compound LC in FIGS. 1 to 3 may be applied to that of alignment layers ALN1 and ALN2 and a liquid crystal compound LC in FIG. 5. For example, in an embodiment shown in FIG. 5, at least one of the alignment layers ALN1 and ALN2 may be an alignment layer formed by the above-described reactive mesogen. Both the first alignment layer ALN1 and the second alignment layer ALN2 may be alignment layers formed by the reactive mesogen. In addition, at least one of the first alignment layer ALN1 and the second alignment layer ALN2 may be an alignment layer formed by the reactive mesogen, and the remaining one may be an alignment layer including a polyimide alignment layer.

Even not shown in FIG. 5, a first substrate SUB1 may include a base substrate and a first electrode layer formed on the base substrate. For example, the first electrode layer formed on the base substrate may be a pixel electrode layer. A second substrate SUB2 may include a base substrate and a second electrode layer formed on the base substrate. For example, the second electrode layer formed on the base substrate in the second substrate may be a common electrode layer.

The base substrate may be a polymer substrate, a plastic substrate, a glass substrate, a quartz substrate, etc. The base substrate in first substrate SUB1 and the second substrate SUB2 may be a transparent insulating substrate. The base substrate may be flexible or rigid.

On the bottom of the first substrate SUB1, a first polarization member PO-1 may be disposed. The first polarization member PO-1 may have various embodiments. For example, the first polarization member PO-1 may be provided as a film type and may be disposed or attached to by a separately provided attaching member on the rear of the first substrate SUB1. The first polarization member PO-1 may be provided as a liquid phase and may be formed via direct coating or deposition on the first substrate SUB1. In other embodiments, different from the illustration in the drawing, the first polarization member PO-1 may be disposed between the first substrate SUB1 and the first alignment layer ALN1.

A second polarization member PO-2 may be disposed between the liquid crystal layer LCL and the color conversion member CCL. The second polarization member PO-2 may be formed using a material having a light transmittance. Accordingly, light provided via the liquid crystal layer LCL may be provided to the color conversion member CCL through the second polarization member PO-2.

The second polarization member PO-2 may polarize incident light and selectively reflect or transmit. For example, the second polarization member PO-2 may be a polarization layer formed adjacent to the liquid crystal layer LCL and may function as a polarization layer opposite to the first polarization member PO-1. Accordingly, the second polarization member PO-2 may polarize light incident to the second polarization member PO-2 in a perpendicular direction to a polarization direction by the first polarization member PO-1.

The second polarization member PO-2 may be a coating type polarization layer or a polarization layer formed by deposition. For example, the second polarization member PO-2 may be an in-cell polarizer. In an embodiment, the second polarization member PO-2 may be a wire grid polarizer. However, an embodiment is not limited thereto. Meanwhile, the disposition of the second polarization member PO-2 is not limited to that shown in FIG. 5, and the second polarization member PO-2 may be disposed on the second substrate SUB.

The light transmitted through the second polarization member PO-2 may be provided as a color conversion member CCL. The color conversion member CCL may include a color conversion part CCF and a black matrix BM. The color conversion part CCF may convert the color according to the energy of incident light via the second polarization member PO-2 or may transmit as it is. Each of filters CF1, CF2 and CF3 of the color conversion part CCF may include at least one optical conversion particle.

The optical conversion particle may absorb at least a part of incident light, and emit light with a certain color or transmit as it is. For example, the optical conversion particle may be quantum dot (QD).

In particular, in an embodiment shown in FIG. 5, a first filter CF1, a second filter CF2, and a third filter CF3 may produce lights having red, green, and blue color, respectively. However, an embodiment is not limited thereto. For example, in the case where a back light unit (not shown) disposed under the first polarization member PO-1 and providing light to a liquid crystal layer LCL provides blue light, the first filter CF1 and the second filter CF2 may produce red light and green light, respectively, and the third filter CF3 may not include an optical conversion particle and transmit and emit blue light provided from the back light unit.

In addition, different from the embodiment shown in the drawing, the color conversion member CCL may be disposed on the second substrate SUB2.

Hereinafter, a reactive mesogen according to an embodiment and a liquid crystal display including the same according to an embodiment will be explained in detail referring to embodiment and comparative embodiments. In addition, the following embodiments are illustrated for the understanding of the inventive concept, and the scope of the invention is not limited thereto.

Examples

1. Synthesis of Reactive Mesogen

The synthetic method of a reactive mesogen according to an embodiment of the inventive concept will be particularly explained referring to synthetic methods of Compounds 1 and 4 in Compound Group 1, Compounds 6 to 9 in Compound Group 2, and Compounds 12 to 14 in Compound Group 3. In addition, the following synthetic method of a reactive mesogen according to an embodiment of the inventive concept is only an illustration, and the synthetic method of a reactive mesogen according to an embodiment of the inventive concept is not limited thereto. For example, the synthetic process of a reactive mesogen according to an embodiment is not limited the suggested reaction conditions, and any conditions well known in the art may be applied.

[Synthesis of Compound 1]

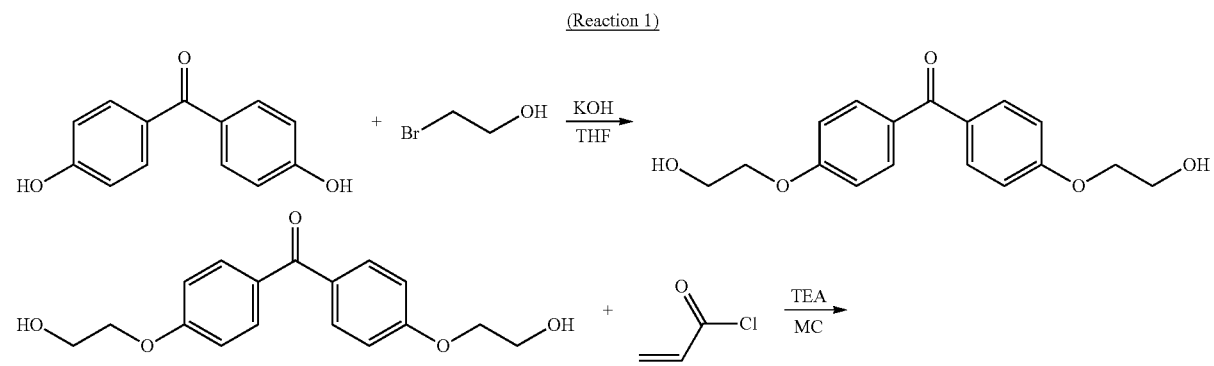

(Reaction 1)

-continued

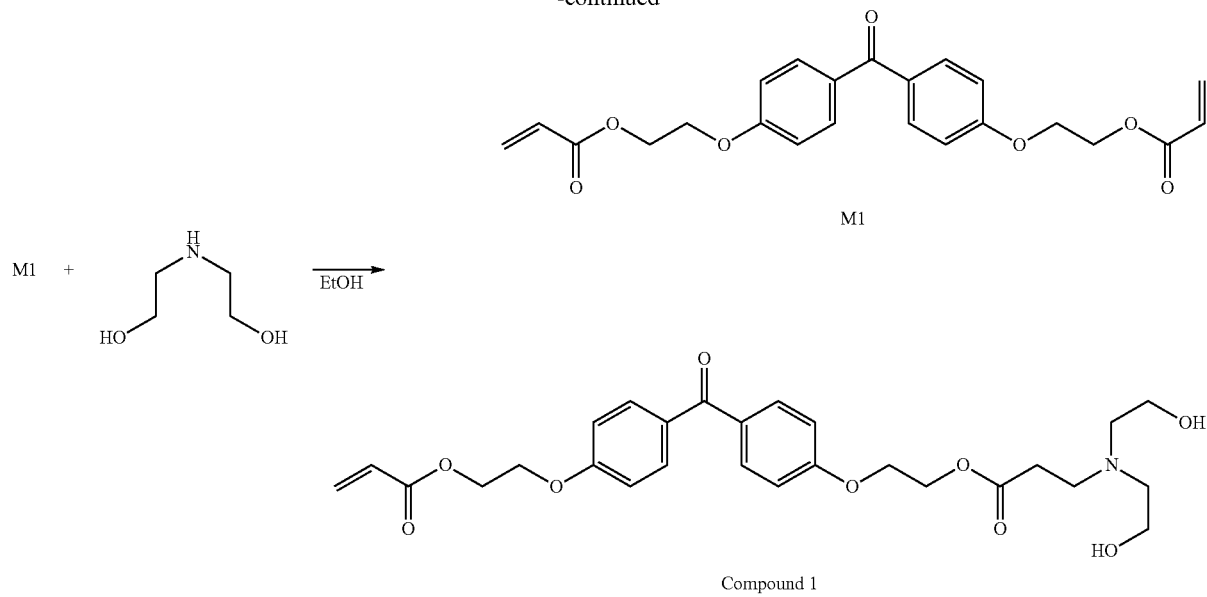

Compound 1 of Compound Group 1 may be prepared on the basis of the preparation example of the reaction process in Reaction 1.

Figure 6:
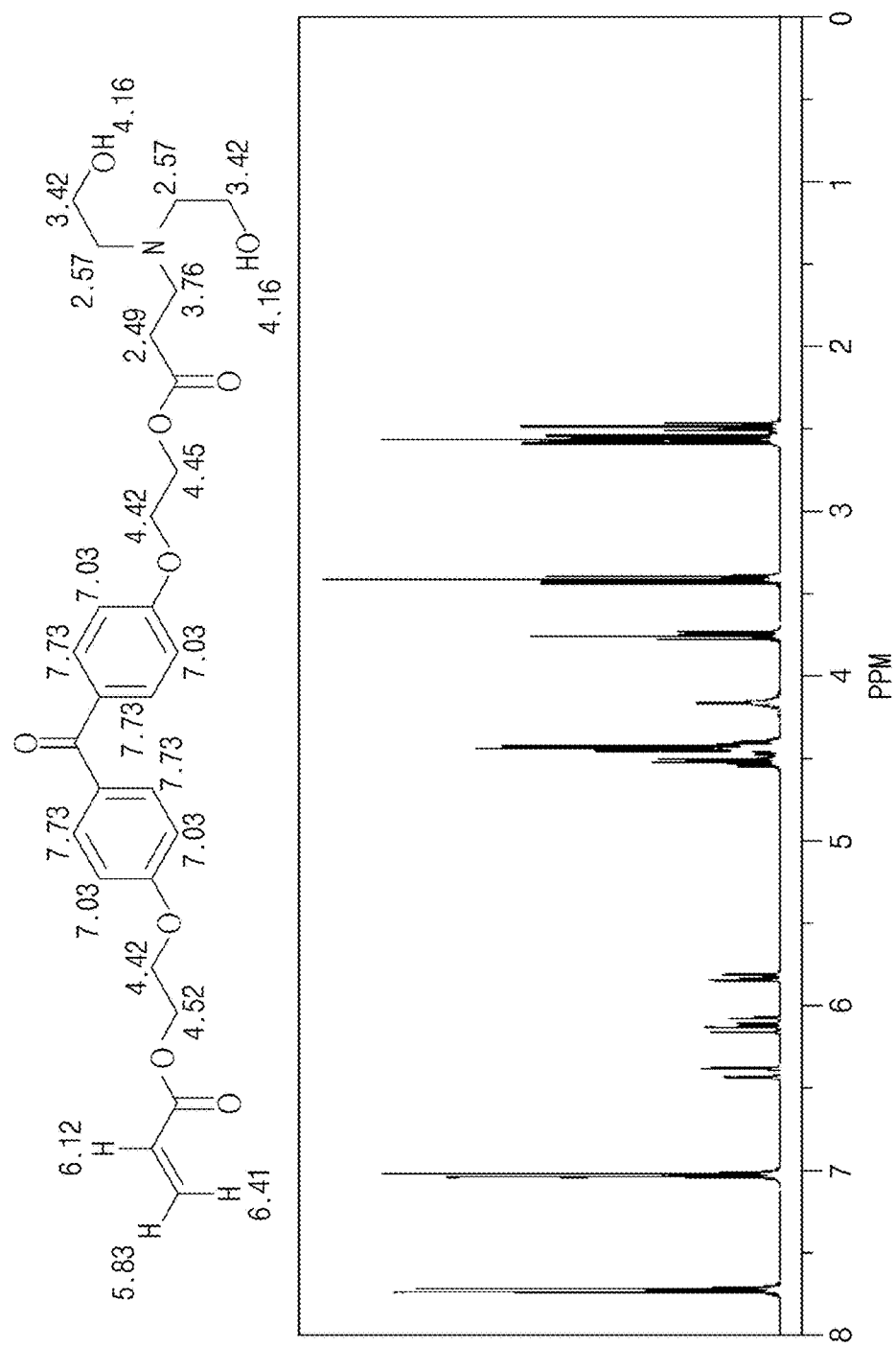
FIGS. 6, 7, 8, 9, 10, 11, 12, 13, and 14 illustrate NMR spectra for identifying the synthesis of Compounds 1, 2, 6 to 9, and 12 to 14, which are reactive mesogens according to exemplary embodiments.

Compound 1 thus synthesized was identified using $^1$H NMR (CDCl3, δ in ppm, 300 MHz) spectrum. NMR spectrum and chemical shift values on Compound 1 synthesized by Reaction 1 are shown in FIG. 6. Referring to FIG. 6, the synthesis of Compound 1 was secured from the NMR spectrum.

[Synthesis of Compound 4]

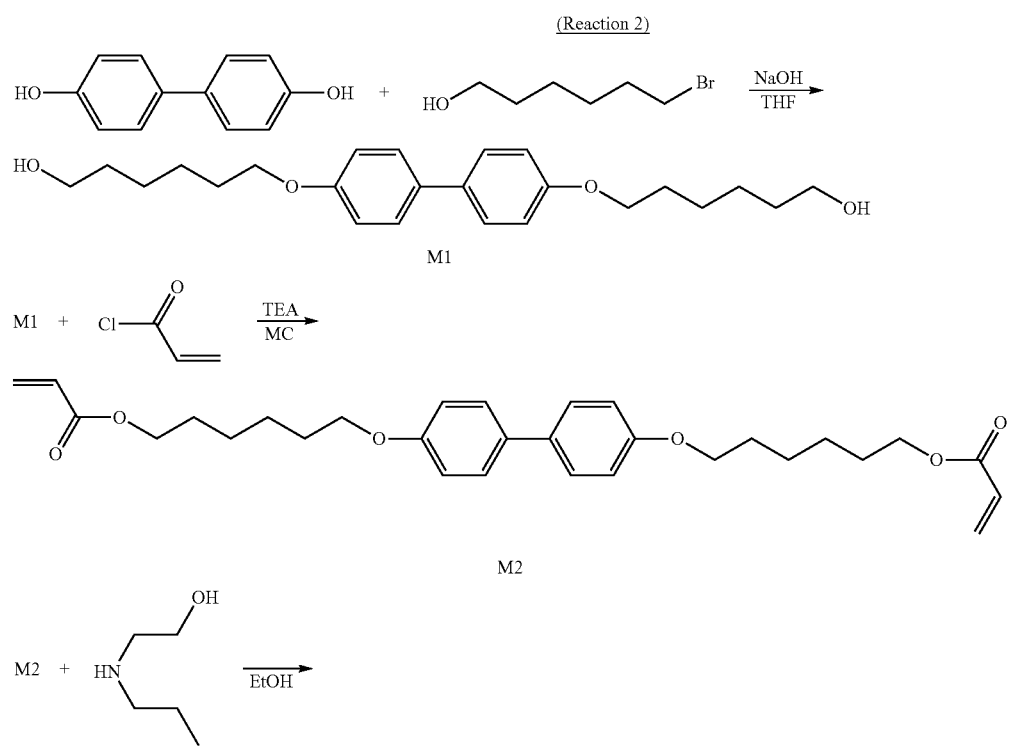

-continued

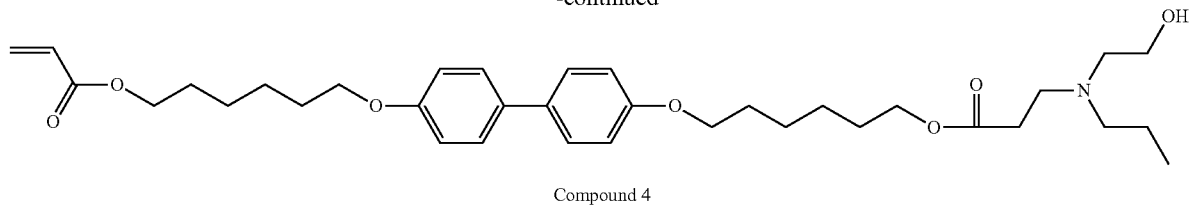

Compound 4

Compound 4 of Compound Group 1 may be prepared on the basis of the preparation example of the reaction process in Reaction 2.

Figure 7:
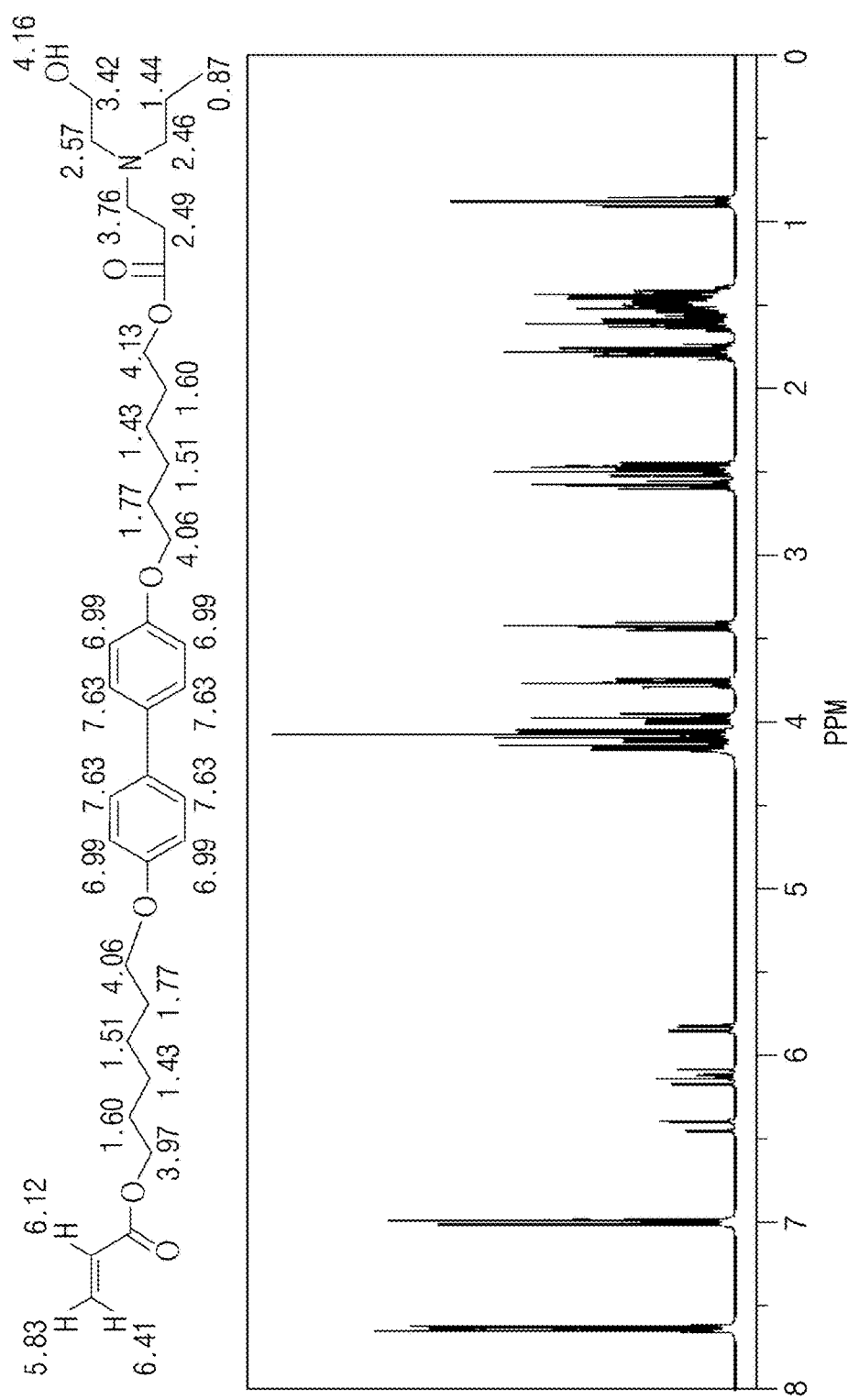

Compound 4 thus synthesized was identified using $^1$H NMR (CDCl3, δ in ppm, 300 MHz) spectrum. NMR spectrum and chemical shift values on Compound 4 synthesized by Reaction 2 are shown in FIG. 7. Referring to FIG. 7, the synthesis of Compound 4 was secured from the NMR spectrum.

[Synthesis of Compound 6]

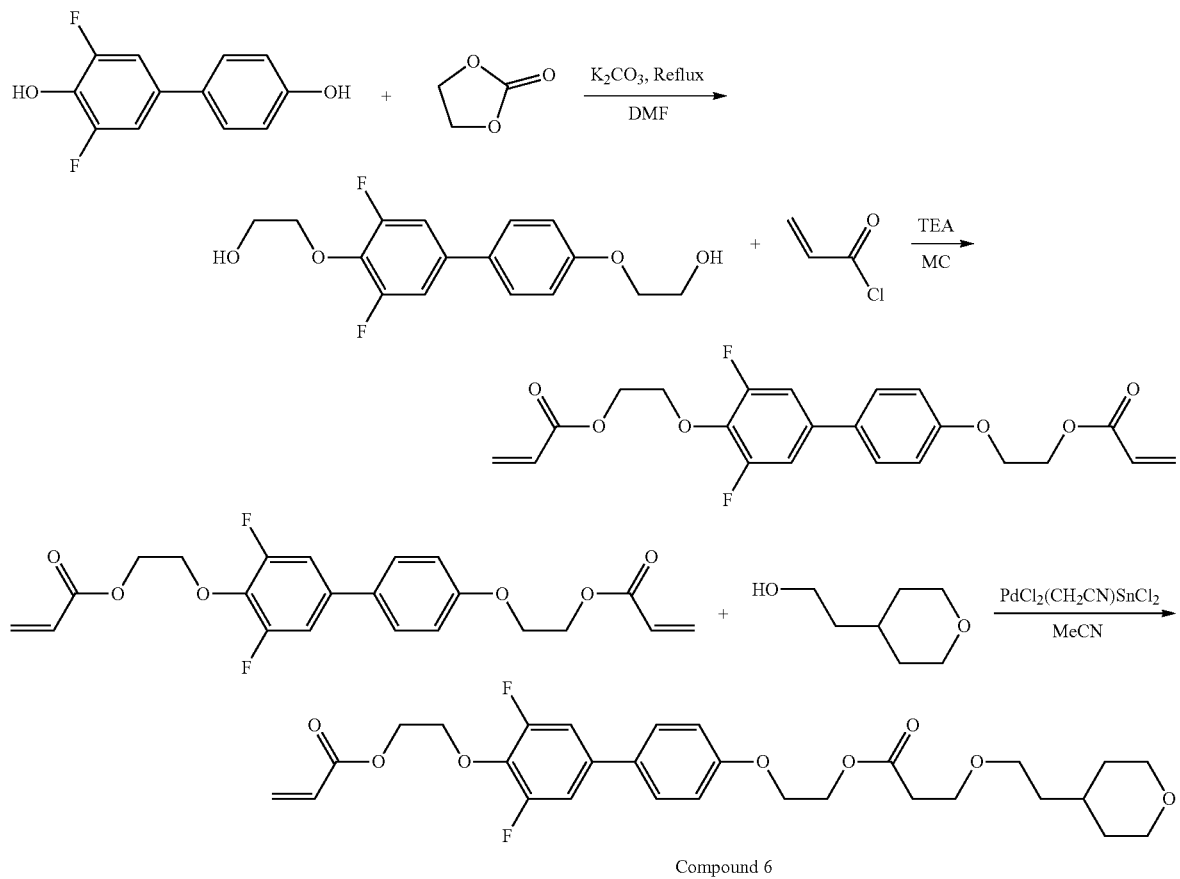

Compound 6

Compound 6 of Compound Group 2 may be prepared on the basis of the preparation example of the reaction process in Reaction 3.

Figure 8:
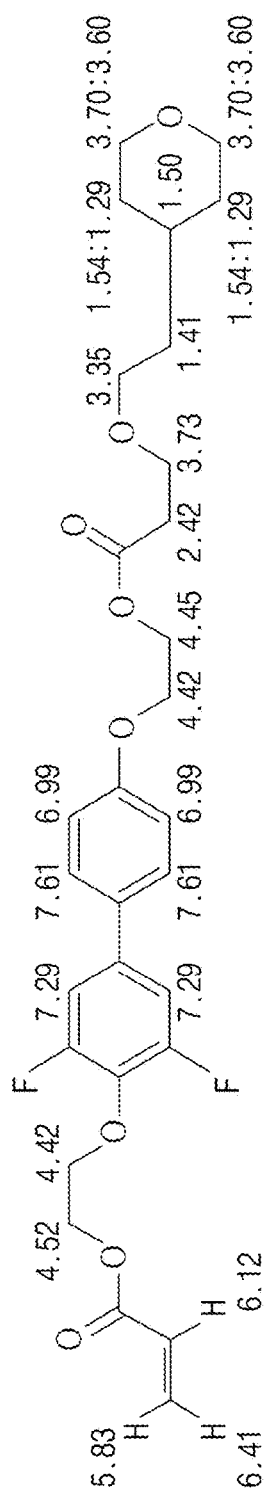
Figure 8:
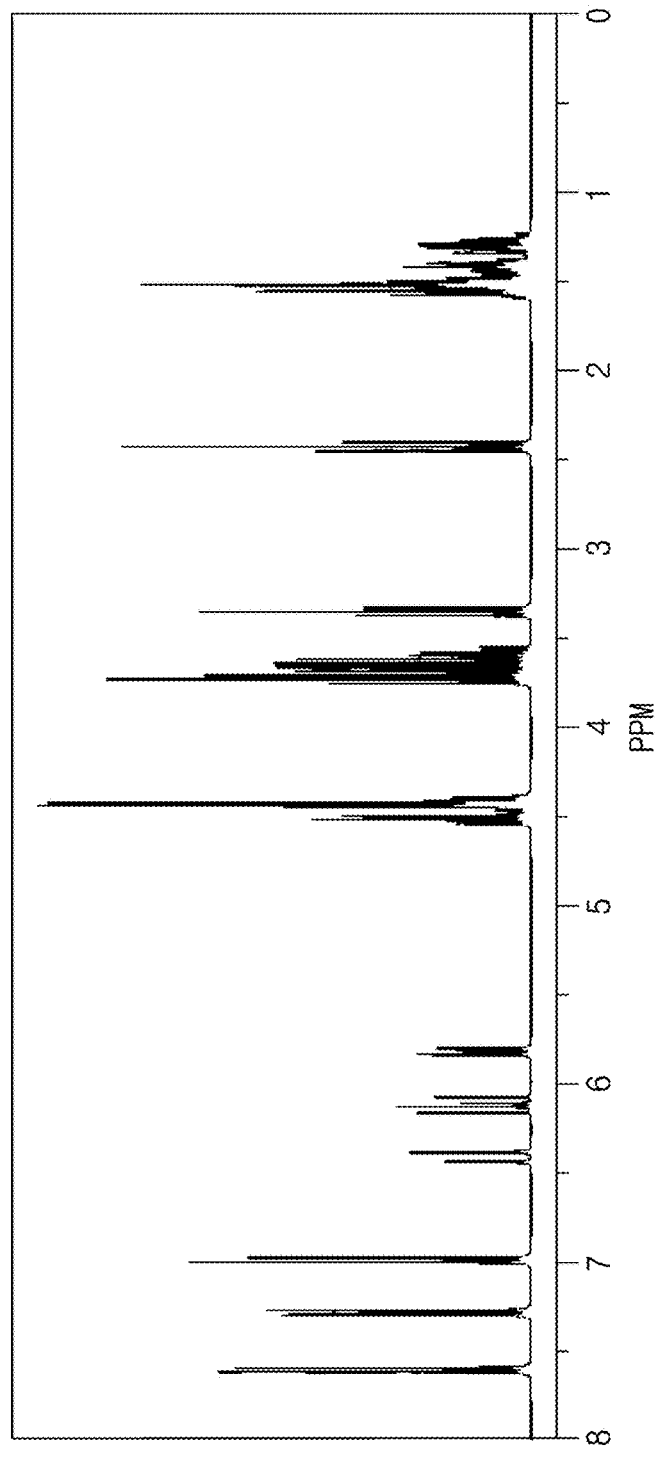

Compound 6 thus synthesized was identified using $^1$H NMR (CDCl3, δ in ppm, 300 MHz) spectrum. NMR spectrum and chemical shift values on Compound 4 synthesized by Reaction 3 are shown in FIG. 8. Referring to FIG. 8, the synthesis of Compound 6 was secured from the NMR spectrum.

[Synthesis of Compound 7]

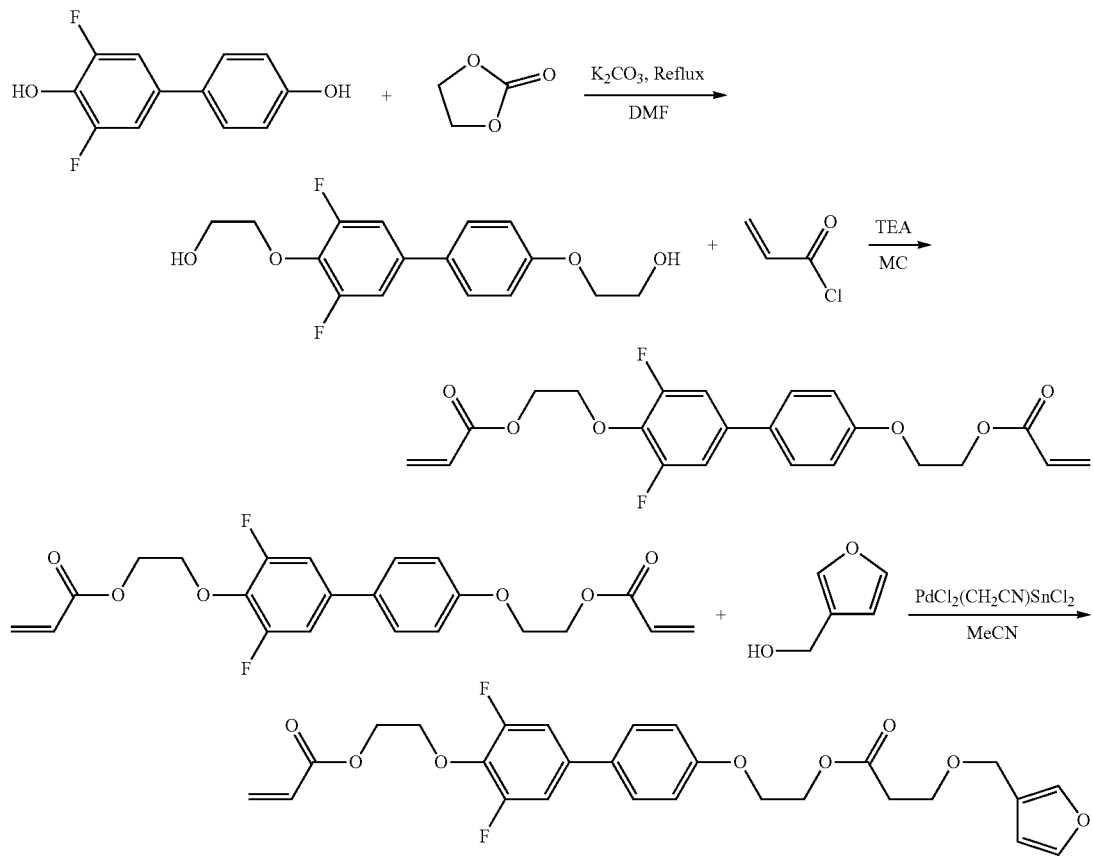

(Reaction 4)

Compound 7

Compound 7 of Compound Group 2 may be prepared on the basis of the preparation example of the reaction process in Reaction 4.

Figure 9:
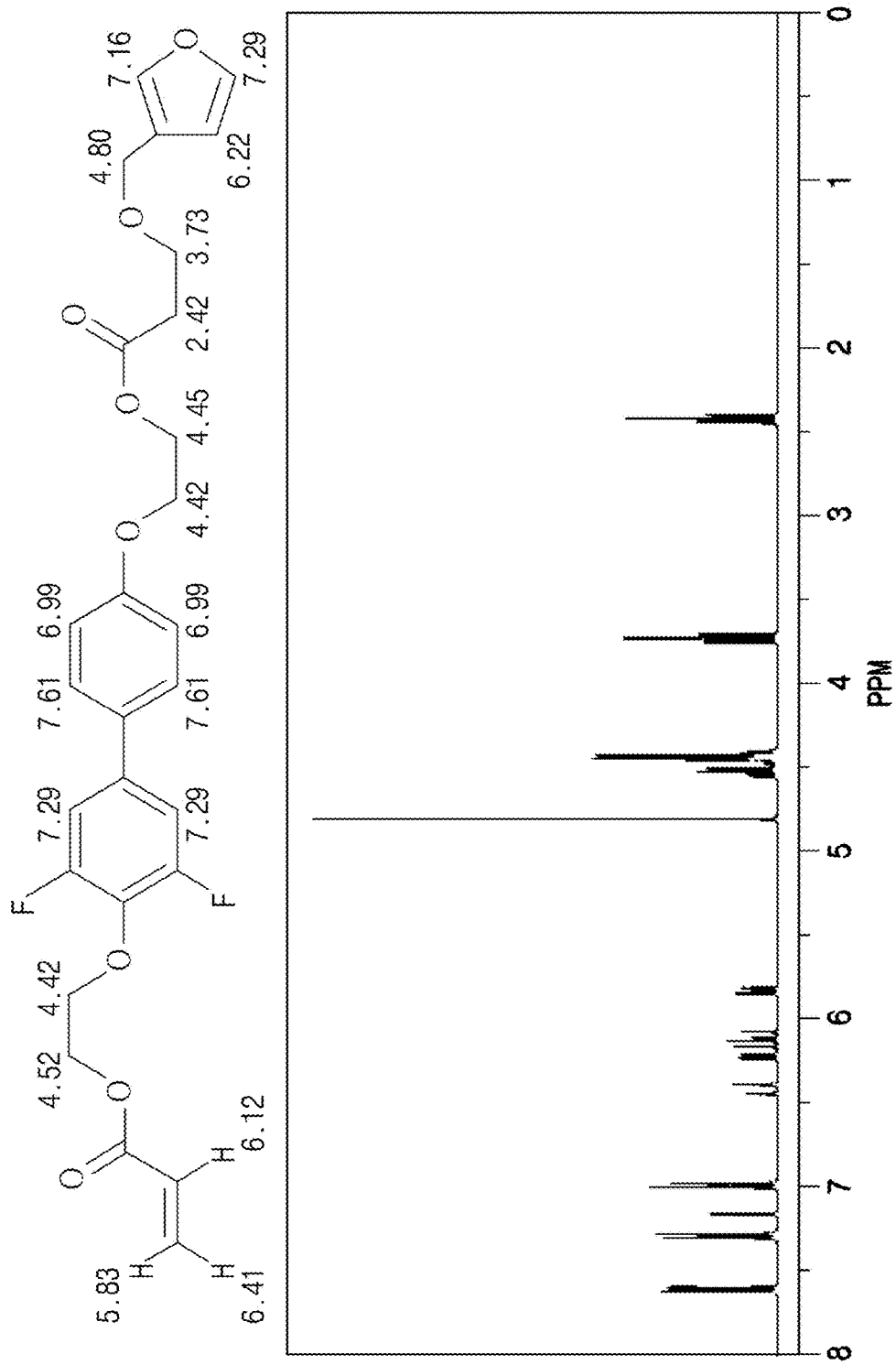

Compound 7 thus synthesized was identified using $^1$H NMR (CDCl3, δ in ppm, 300 MHz) spectrum. NMR spectrum and chemical shift values on Compound 7 synthesized by Reaction 4 are shown in FIG. 9. Referring to FIG. 9, the synthesis of Compound 7 was secured from the NMR spectrum.

[Synthesis of Compound 8]

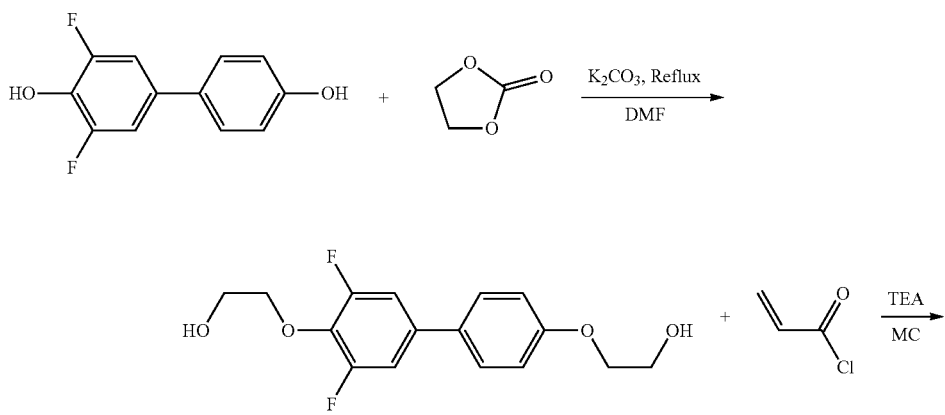

(Reaction 5)

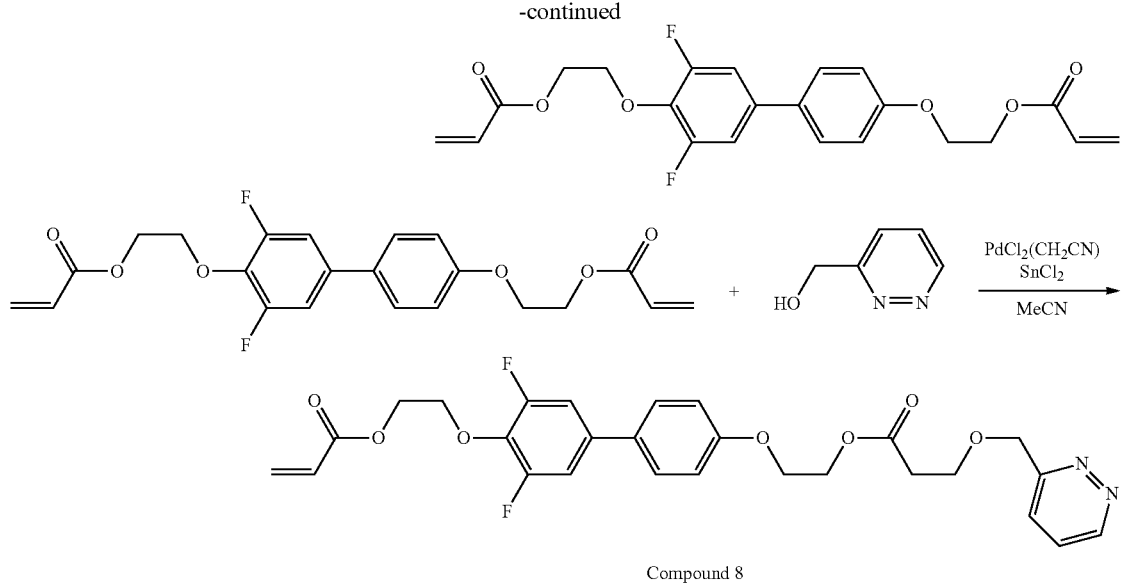

Compound 8 of Compound Group 2 may be prepared on the basis of the preparation example of the reaction process in Reaction 5.

Figure 10:
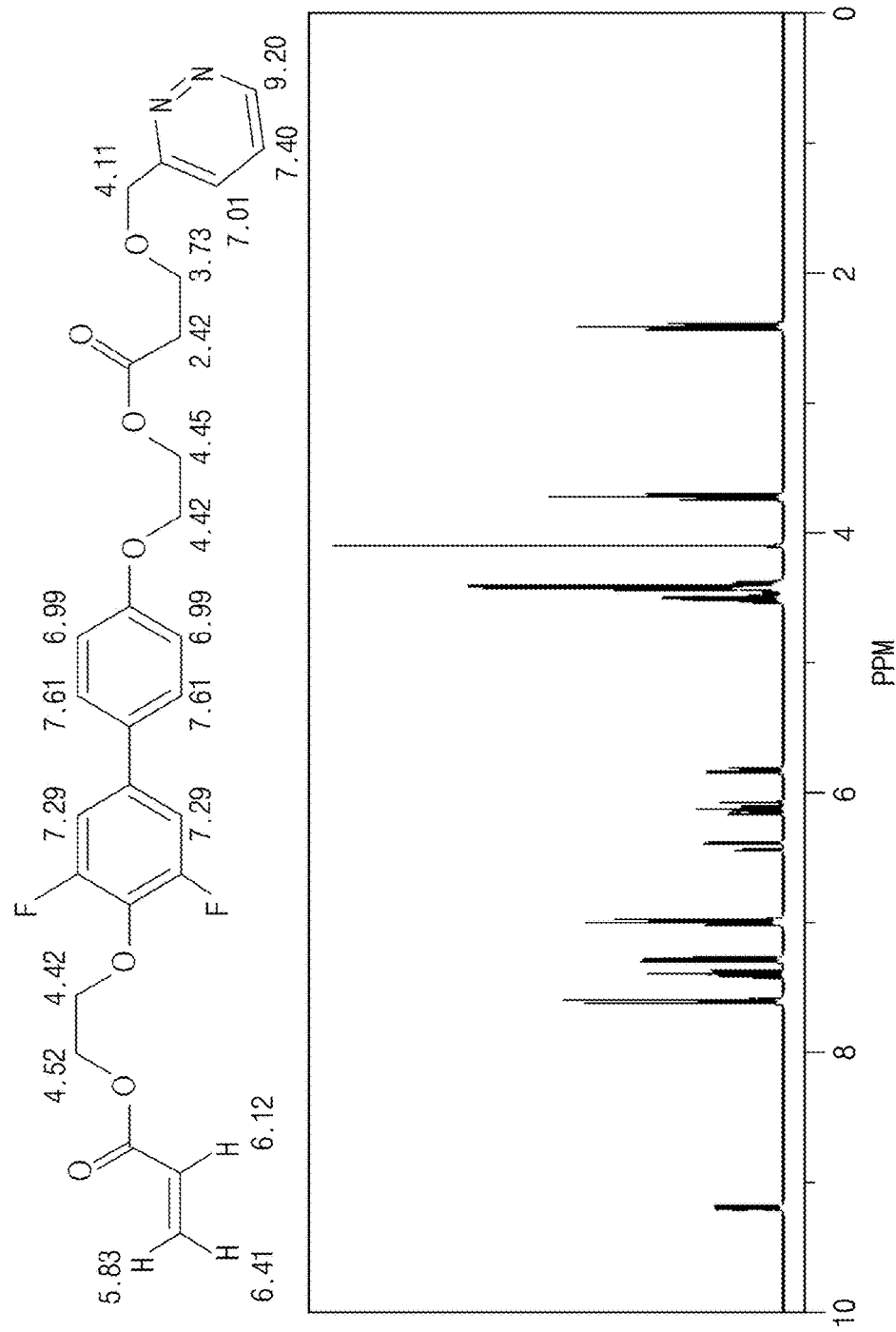

Compound 8 thus synthesized was identified using $^1$H NMR (CDCl3, δ in ppm, 300 MHz) spectrum. NMR spectrum and chemical shift values on Compound 8 synthesized by Reaction 5 are shown in FIG. 10. Referring to FIG. 10, the synthesis of Compound 8 was secured from the NMR spectrum.

[Synthesis of Compound 9]

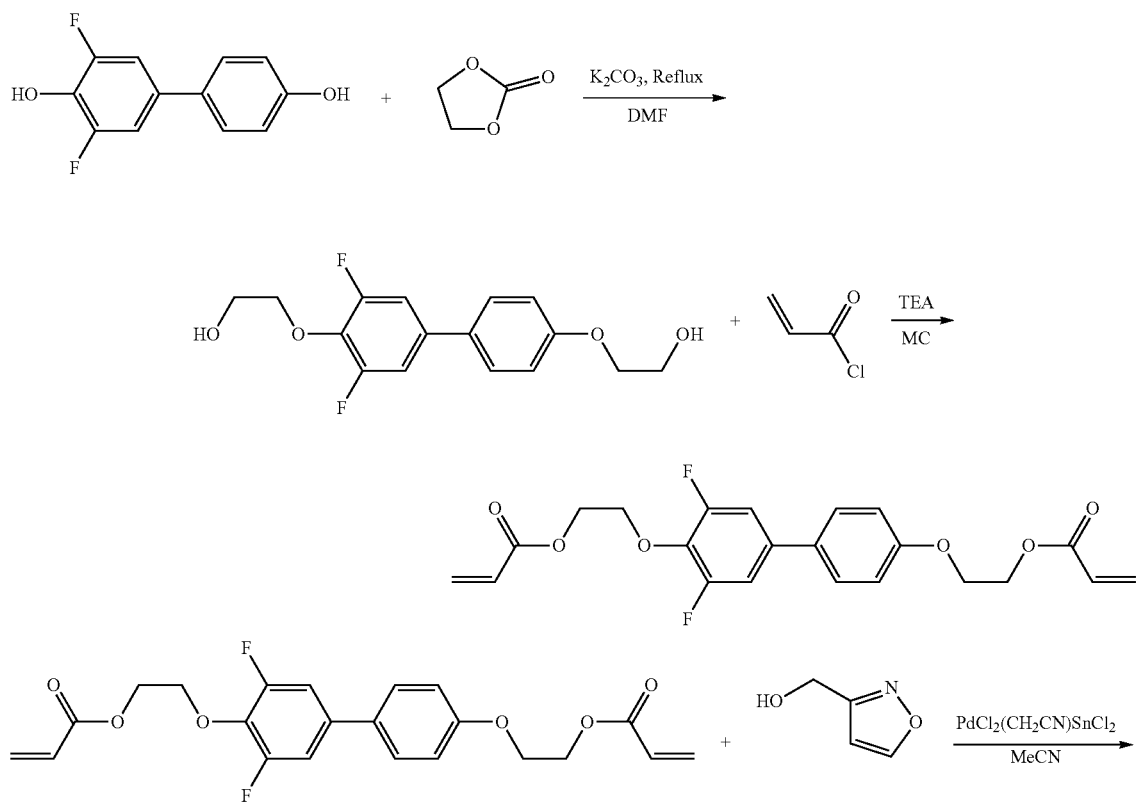

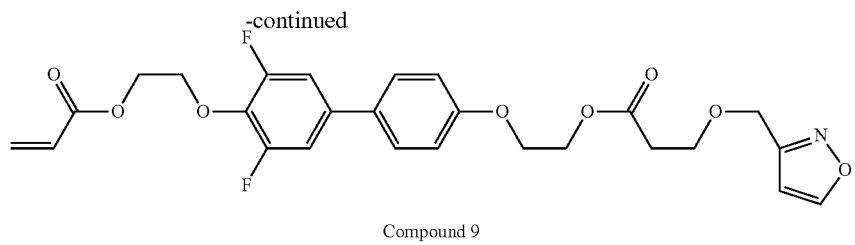

Compound 9

Compound 9 of Compound Group 2 may be prepared on the basis of the preparation example of the reaction process in Reaction 6.

Figure 11:
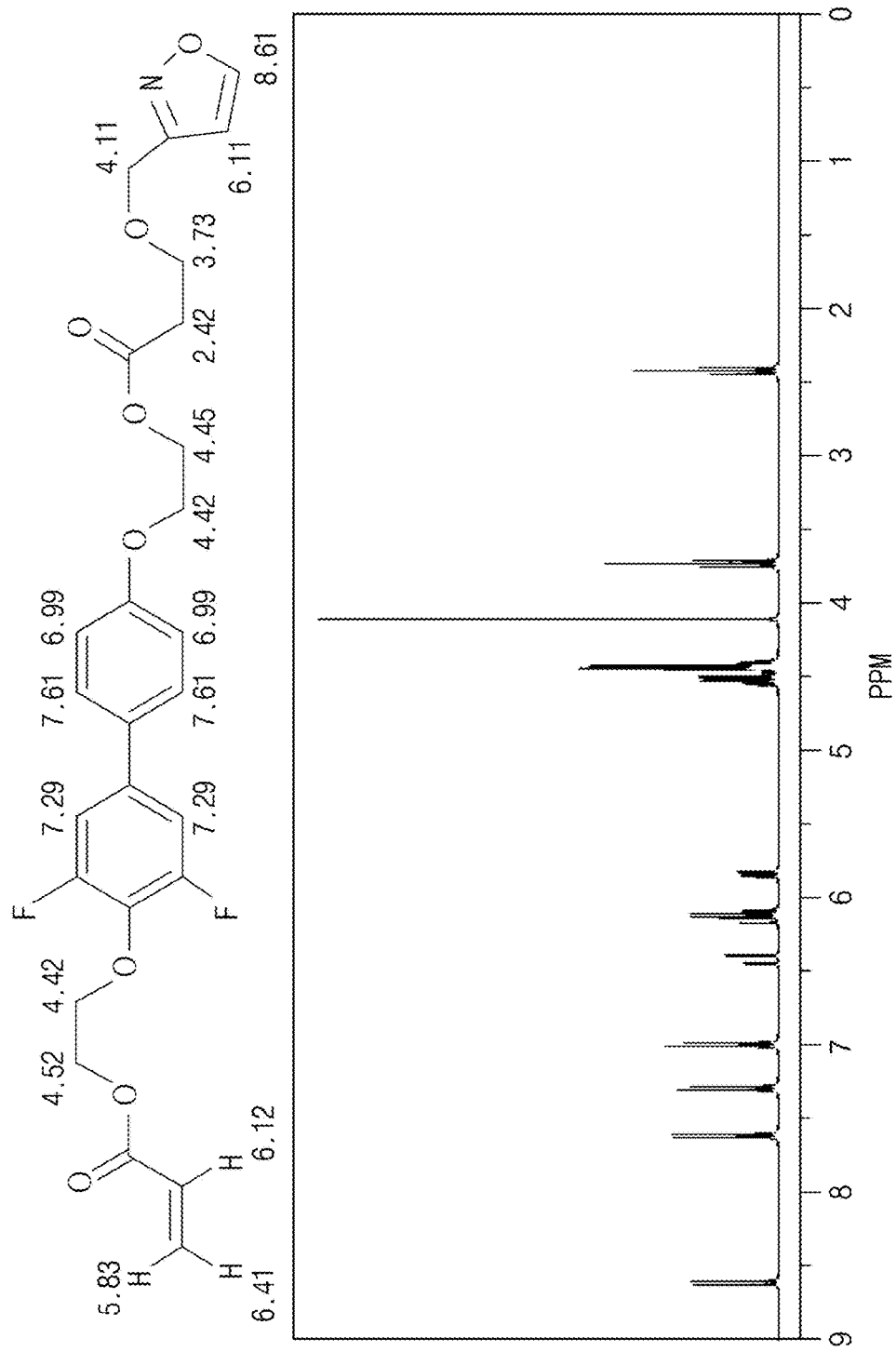

Compound 9 thus synthesized was identified using $^1$H NMR (CDCl3, δ in ppm, 300 MHz) spectrum. NMR spectrum and chemical shift values on Compound 9 synthesized by Reaction 6 are shown in FIG. 11. Referring to FIG. 11, the synthesis of Compound 9 was secured from the NMR spectrum.

[Synthesis of Compound 12]

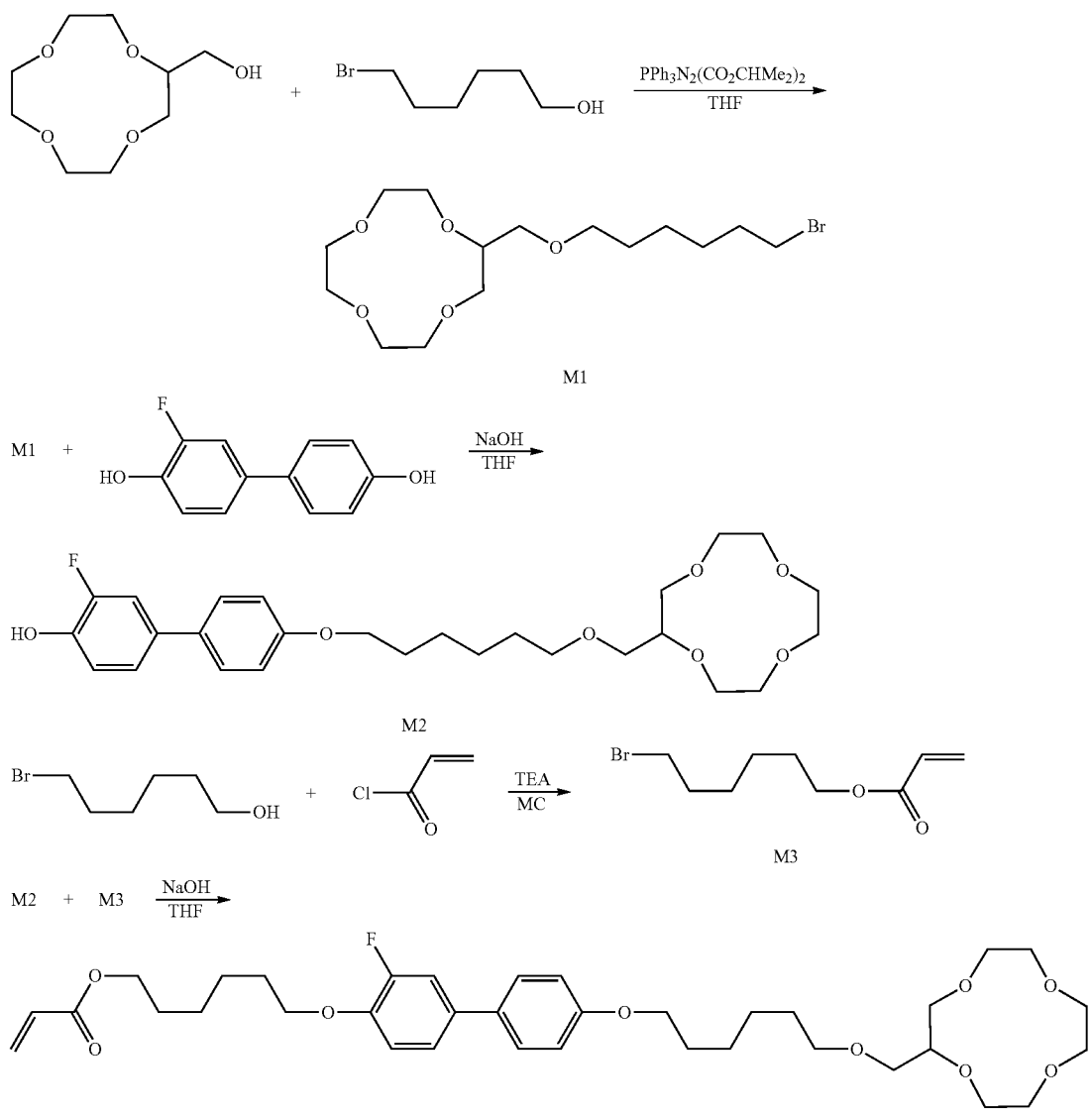

Compound 12

Compound 12 of Compound Group 3 may be prepared on the basis of the preparation example of the reaction process in Reaction 7.

Figure 12:
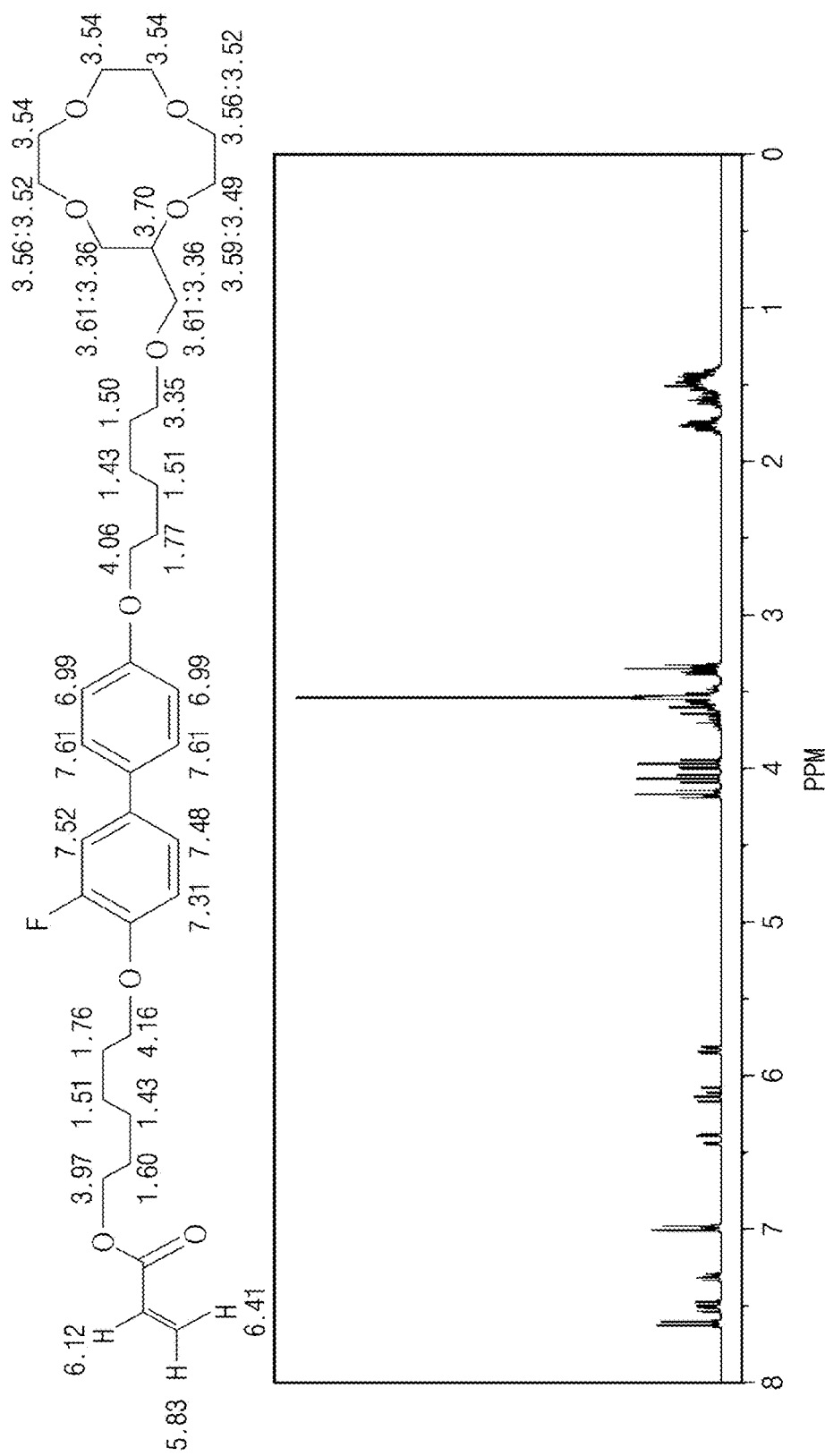

Compound 12 thus synthesized was identified using $^1$H NMR (CDCl3, δ in ppm, 300 MHz) spectrum. NMR spectrum and chemical shift values on Compound 12 synthesized by Reaction 7 are shown in FIG. 12. Referring to FIG. 12, the synthesis of Compound 12 was secured from the NMR spectrum.

[Synthesis of Compound 13]

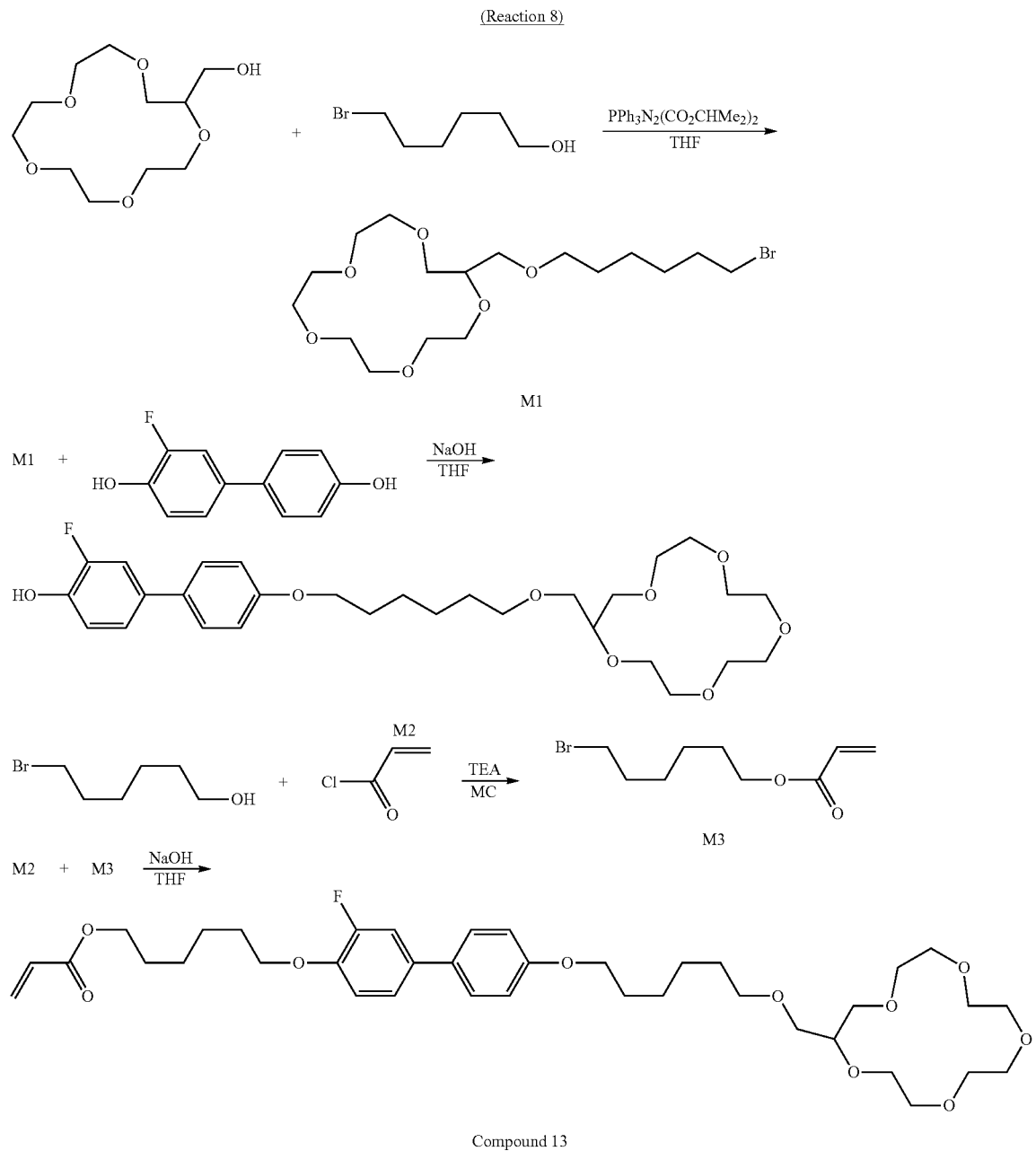

(Reaction 8)

Compound 13 of Compound Group 3 may be prepared on the basis of the preparation example of the reaction process in Reaction 8.

Figure 13:
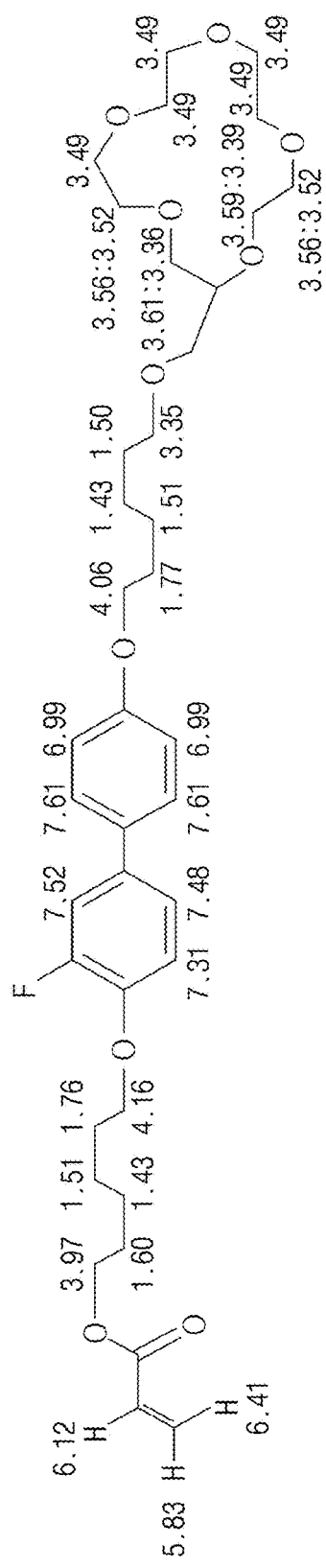
Figure 13:
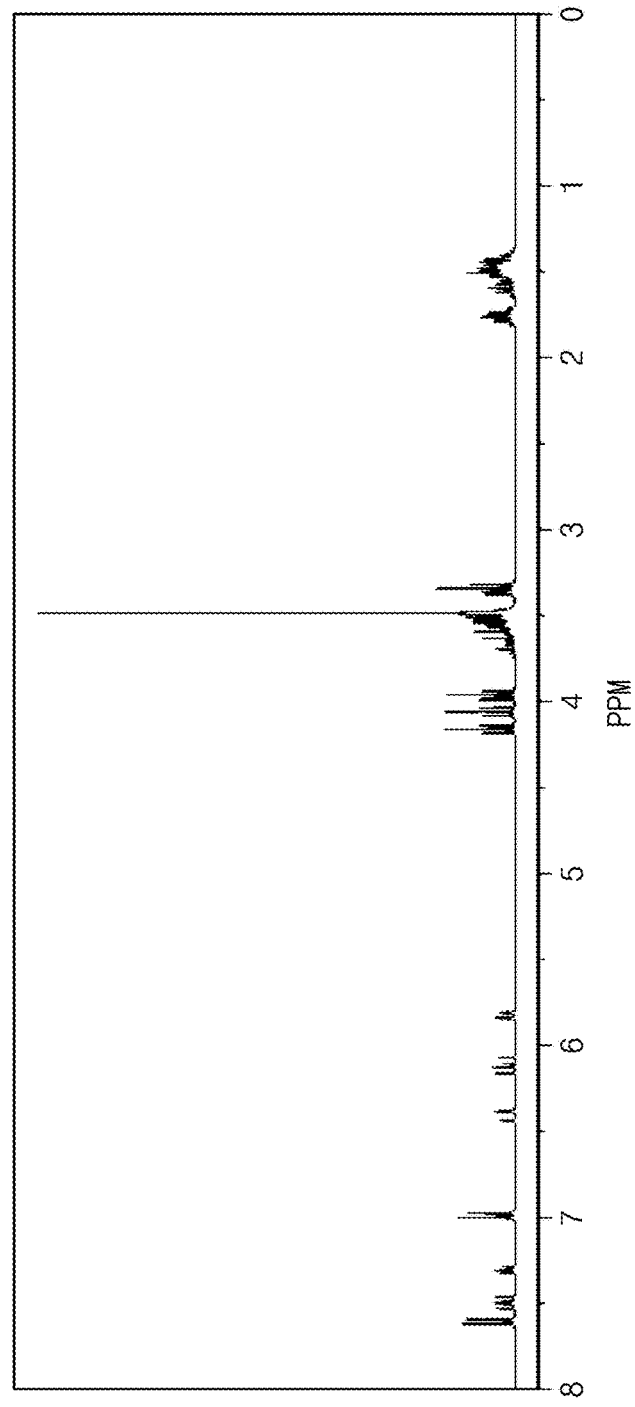

Compound 13 thus synthesized was identified using $^1$H NMR (CDCl3, δ in ppm, 300 MHz) spectrum. NMR spectrum and chemical shift values on Compound 13 synthesized by Reaction 8 are shown in FIG. 13. Referring to FIG. 13, the synthesis of Compound 13 was secured from the NMR spectrum.

[Synthesis of Compound 14]

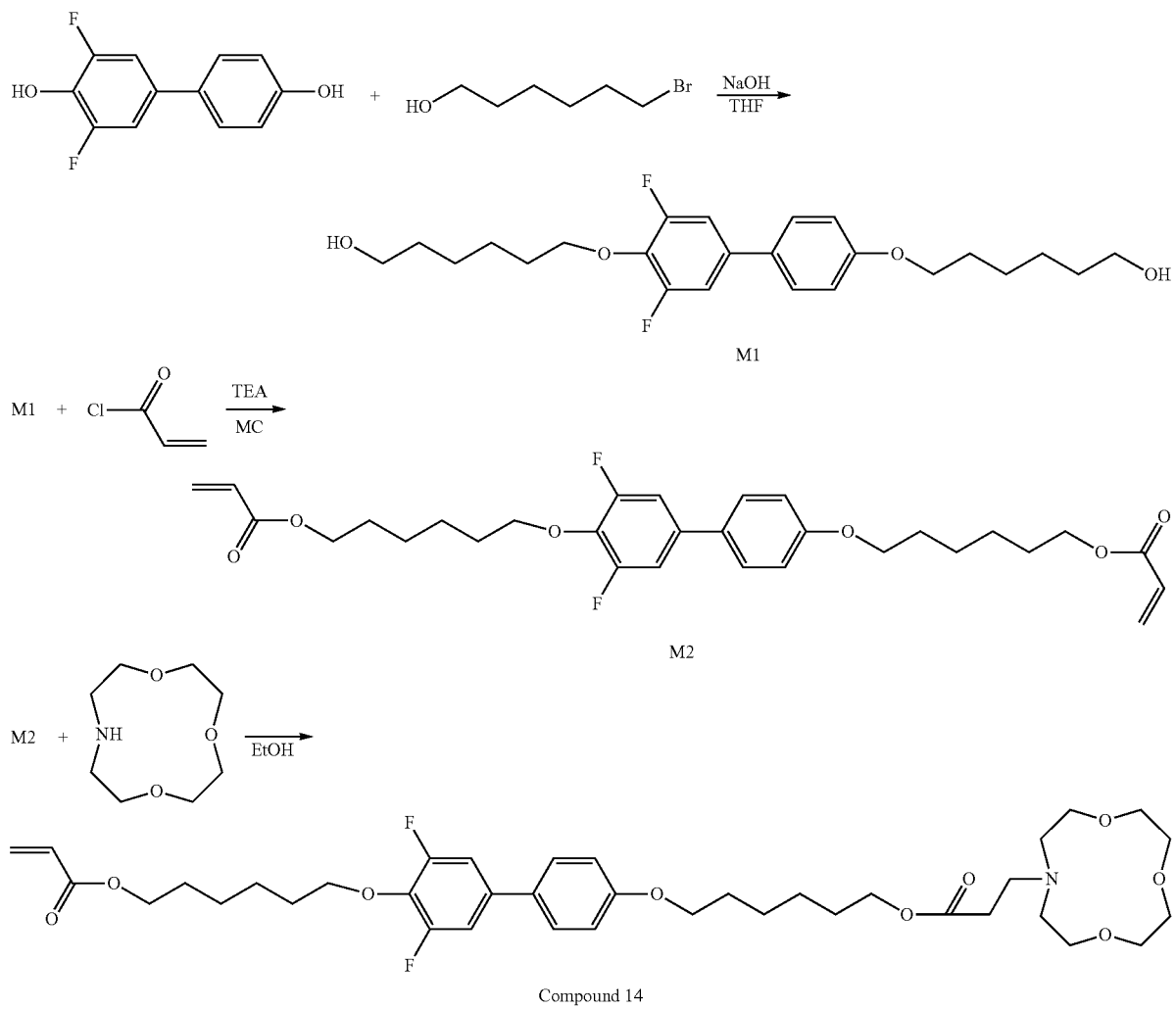

(Reaction 9)

Compound 14

Compound 14 of Compound Group 3 may be prepared on the basis of the preparation example of the reaction process in Reaction 9.

Figure 14:
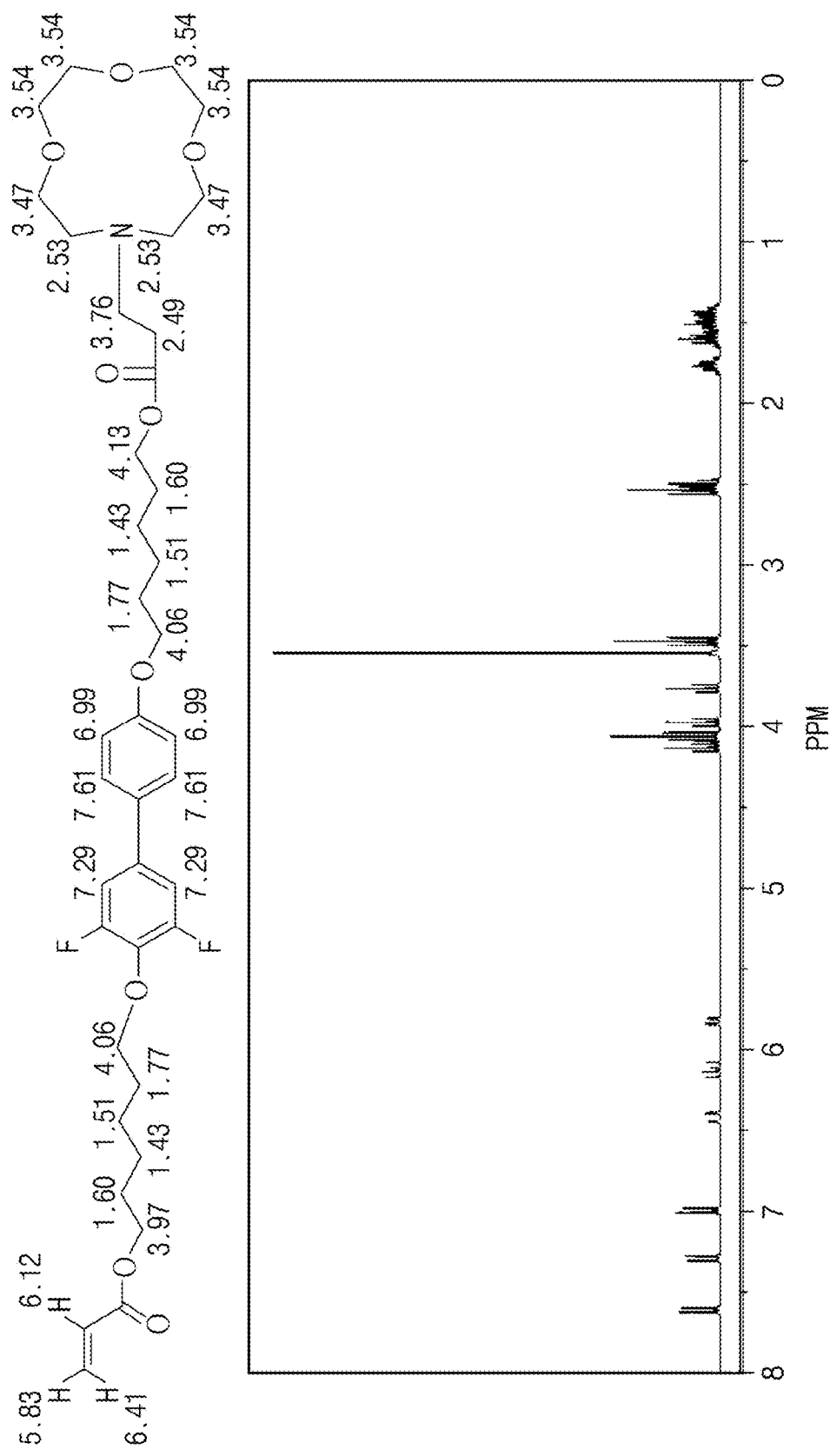

Compound 14 thus synthesized was identified using $^1$H NMR (CDCl3, δ in ppm, 300 MHz) spectrum. NMR spectrum and chemical shift values on Compound 14 synthesized by Reaction 9 are shown in FIG. 14. Referring to FIG. 14, the synthesis of Compound 14 was secured from the NMR spectrum thus measured.

2. Evaluation of Physical Properties of Reactive Mesogens

The solubility with a liquid crystal compound and the adsorption energy with an electrode of the reactive mesogens according to exemplary embodiments were evaluated. The evaluation on the solubility and adsorption energy were performed using a Materials Studio simulation program, and a comparative compound and example compounds used are listed in Table 2 below. The resulting values of the simulation are obtained using quantum calculation and molecular dynamics.

TABLE 2

| Division | Reactive mesogen | Formula |
|---|---|---|
| Comparative Example | Comparative Compound | |

TABLE 2-continued

| Division | Reactive mesogen | Formula |
|---|---|---|
| Example 1 | Compound 1 | |
| Example 2 | Compound 2 | |
| Example 3 | Compound 4 | |
| Example 4 | Compound 6 | |
| Example 5 | Compound 7 | |
| Example 6 | Compound 8 | |
| Example 7 | Compound 9 | |
| Example 8 | Compound 12 | |

TABLE 2-continued

| Division | Reactive mesogen | Formula |
|---|---|---|
| Example 9 | Compound 13 | (structure shown) |
| Example 10 | Compound 14 | (structure shown) |

The simulation results on Comparative Compound, and Compounds 1, 2, 4, 6 to 9, and 12 to 14 disclosed in Table 2 were compared and shown in Table 3. In Table 3, the solubility (Δδ) represents solubility for a case where a liquid crystal compound and the comparative compound or the example compounds shown in Table 2, which are reactive mesogens, were mixed. As the "solubility (Δδ)" value decreases, the solubility of the reactive mesogen with respect to the liquid crystal compound increases. The liquid crystal compounds used for the simulation correspond to a nematic liquid crystal mixture. The adsorption energy represents adsorption energy of the compounds according to the comparative example and the examples with respect to an ITO electrode. As the absolute value of the adsorption energy increases, the adsorption energy of the reactive mesogen with respect to the ITO electrode increases. In addition, "self initiation efficiency" may be a value representing the production rate of free radicals. As the value of "self initiation efficiency" increases, the production rate of free radicals may increase, and the polymerization rate of the reactive mesogen may increase.

TABLE 3

| Division | Reactive mesogen | Solubility (Δδ) | Adsorption energy (eV) | Self initiation efficiency |
|---|---|---|---|---|
| Comparative Example | Comparative Compound | 1.5 | −0.49 | 0.167 |
| Example 1 | Compound 1 | 5.1 | −1.27 | 0.764 |
| Example 2 | Compound 2 | 3.1 | −1.34 | 0.247 |
| Example 3 | Compound 4 | 1.3 | −0.99 | 0.127 |
| Example 4 | Compound 6 | 1.8 | −0.40 | 0.138 |
| Example 5 | Compound 7 | 1.6 | −0.45 | 0.179 |
| Example 6 | Compound 8 | 1.5 | −0.51 | 0.236 |
| Example 7 | Compound 9 | 1.5 | −0.53 | 0.128 |
| Example 8 | Compound 12 | 1.2 | −0.73 | 0.235 |
| Example 9 | Compound 13 | 1.1 | −0.82 | 0.235 |
| Example 10 | Compound 14 | 1.2 | −0.97 | 0.367 |

Referring to the results in Table 3, the absolute values of the adsorption energy for Examples 1, 2 and 3 using Compounds 1, 2 and 4 in Compound Group 1, which are reactive mesogens according to exemplary embodiments, were greater when compared to that for Comparative Example using the comparative compound. That is, the reactive mesogen according to an embodiment has greater adsorption energy with respect to an ITO electrode when compared to that of the reactive mesogen of the comparative compound. Particularly, the adsorption energy of Examples 1 and 2, which include a reactive mesogen having two —OH groups at the terminal thereof, was greater than that of Example 3. Since the reactive mesogens according to exemplary embodiments, represented by Compounds 1, 2 and 4, have increased adsorption energy with respect to an electrode when compared to the reactive mesogen of Comparative Example, a stable alignment layer may be formed.

In addition, Example 3 has a smaller Δδ value, which exhibits the solubility of the reactive mesogen with respect to the liquid crystal compound when compared to Examples 1 and 2, and the solubility with respect to the liquid crystal compound of Example 3 is secured to be greater when compared to those of Examples 1 and 2. That is, by introducing an alkyl group in place of an —OH group at the terminal which corresponds to an anchoring group of a reactive mesogen, increasing effect of the solubility with respect to the liquid crystal compound may be obtained when compared to Examples 1 and 2.

Examples 4 to 7, which correspond to novel reactive mesogens of exemplary embodiments having an unsubstituted heterocycle at the terminal thereof and represented by Compounds 6 to 9 exhibited the same degree of physical properties such as solubility and adsorption energy as the reactive mesogen of Comparative Example.

The "self initiation efficiency" value was high for Examples 1 and 2. The reactive mesogens of Compounds 1 and 2 include

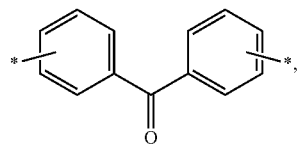

which may generate free radicals, at a core part to increase a polymerization degree, so that high "self initiation efficiency" may be exhibited.

In Examples 8, 9 and 10 using Compounds 12, 13 and 14 in Compound Group 3, the absolute values of the adsorption energy were large when compared to those of Comparative Example. That is, the reactive mesogen of an embodiment having a crown ether group at the terminal thereof has greater adsorption energy with respect to an ITO electrode when compared to the reactive mesogen of the comparative compound. Therefore, the reactive mesogens of Examples 8 to 10, which include a crown ether group at the terminal group which is an anchoring group, have increased adsorption energy with respect to an electrode, and a stable alignment layer may be formed.

In addition, the Δδ values of the reactive mesogens according to Examples 8 to 10 were relatively smaller than that of Comparative Example, and thus, it is secured that the solubility of the reactive mesogens of Examples 8 to 10 with respect to the liquid crystal compound is greater than that of Comparative Example. The "self initiation efficiency" values of Examples 8 to 10 were also greater than that of Comparative Example.

Figure 15A:
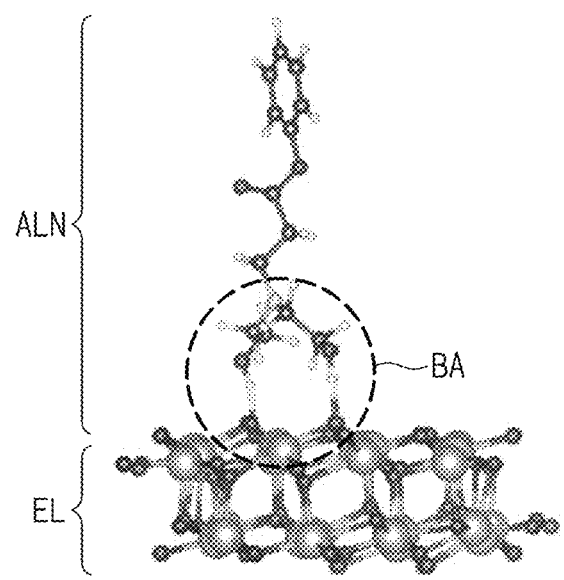
FIGS. 15A, 15B, and 15C are diagrams schematically illustrating the combination relation between a reactive mesogen according to an embodiment and an electrode.
Figure 15B:
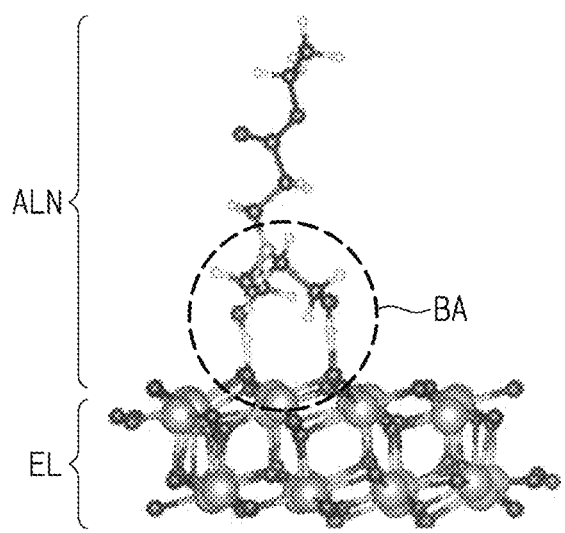
Figure 15C:
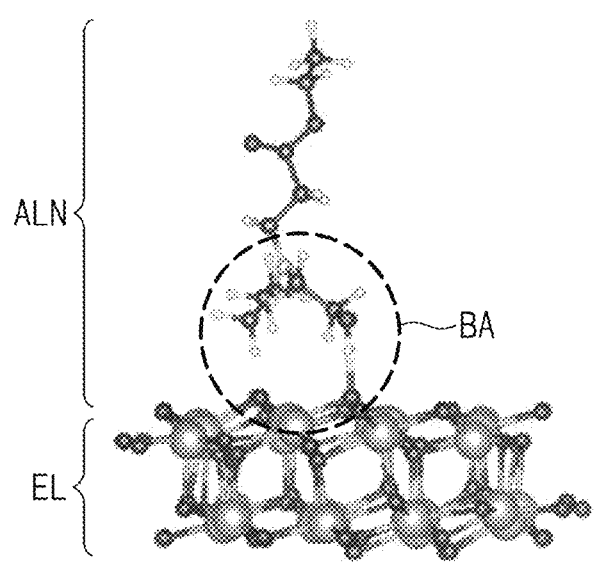

FIGS. 15A to 15C are diagrams schematically illustrating the combination relation between a reactive mesogen according to an embodiment and an electrode layer to which the reactive mesogen is provided. FIGS. 15A to 15C may show the combination relation between the reactive mesogens of Compounds 1, 2 and 4 disclosed in Table 2 and an electrode layer.

Referring to FIGS. 15A to 15C, an alignment layer ALN may be formed on an electrode layer EL. In FIGS. 15A to 15C, the electrode layer EL may be an ITO electrode. In FIGS. 15A to 15C, the alignment layer ALN may schematically illustrate a portion of the stereochemical structure of the reactive mesogen compound. Particularly, "BA" part may be a part corresponding to an anchoring group in the reactive mesogen according to an embodiment.

In FIGS. 15A to 15B, since Compounds 1 and 2 have two —OH groups at the anchoring group, two —OH groups are combined with the electrode layer EL, respectively. In comparison, FIG. 15C corresponds to the reactive mesogen of Compound 4, and only one —OH group in the anchoring group of Compound 4 is combined with the electrode layer EL.

3. Manufacture of Liquid Crystal Display and Evaluation of Display Quality of Liquid Crystal Display (1) Manufacture of Liquid Crystal Display A first substrate on which a pixel electrode, etc, is formed, and a second substrate on which a common electrode, etc. is formed are prepared. A liquid crystal composition is provided on the first substrate by a liquid crystal dropping method. In this case, the supplied liquid crystal composition includes a liquid crystal compound and Compound 2 of Compound Group 1. Compound 2 was provided after controlling the amount to about 0.1 parts by weight, about 0.15 parts by weight, about 0.25 parts by weight, and about 0.3 parts by weight on the basis of about 100 parts by weight of the liquid crystal compound.

Then, the first substrate to which the liquid crystal composition is dropped and the second substrate are attached. In this case, a sealing layer is provided at the edge part between the first substrate and the second substrate to combine the first substrate and the second substrate. After combining the first substrate and the second substrate, ultraviolet rays are irradiated to cure the sealing layer. In this case, a shadow mask is used for curing the sealing layer. Then, an electric field is applied between the first substrate and the second substrate to polymerize the reactive mesogen in the liquid crystal composition, thereby achieving alignment for tilting the liquid crystal compound. Then, the electric field between the first substrate and the second substrate is removed, and ultraviolet rays are additionally irradiated to the liquid crystal layer to polymerize unreacted reactive mesogen.

(2) Evaluation of Display Quality of Liquid Crystal Display

Figure 16:
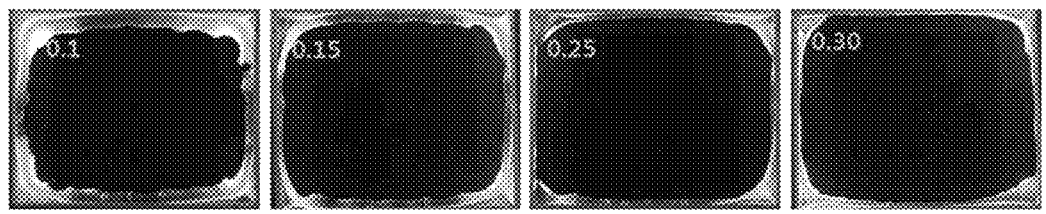
FIG. 16 illustrates images illustrating display quality of a liquid crystal display in accordance with an amount included of a reactive mesogen according to an embodiment.

FIG. 16 illustrates images on the display quality in accordance with the amount included of a reactive mesogen according to an embodiment in a liquid crystal composition provided to a liquid crystal display.

Referring to FIG. 16, according to the increase of the amount of Compound 2, which is a reactive mesogen, the alignment of a liquid crystal compound in a peripheral region of a display is improved, and the display quality of a liquid crystal display is improved.

4. Manufacture of Liquid Crystal Display and Evaluation of Electrical Properties of Liquid Crystal Display (1) Manufacture of Liquid Crystal Display A first substrate on which a pixel electrode, etc. is formed and a second substrate and a second substrate on which a common electrode, etc. is formed are prepared. A liquid crystal composition is provided on the first substrate by a liquid crystal dropping method. In this case, the supplied liquid crystal composition includes a liquid crystal compound and Compound 12 of Compound Group 3.

Then, the first substrate to which the liquid crystal composition is dropped and the second substrate are attached. In this case, a sealing layer is provided at the edge part between the first substrate and the second substrate to combine the first substrate and the second substrate. After combining the first substrate and the second substrate, ultraviolet rays are irradiated to cure the sealing layer. In this case, a shadow mask is used for curing the sealing layer. Then, an electric field is supplied between the first substrate and the second substrate to polymerize the reactive mesogen in the liquid crystal composition, thereby achieving alignment for tilting the liquid crystal compound. Then, the electric field between the first substrate and the second substrate is removed, and ultraviolet rays are additionally irradiated to the liquid crystal layer to polymerize unreacted reactive mesogen.

(2) Evaluation of Electrical Properties of Liquid Crystal Display

Figure 17A:
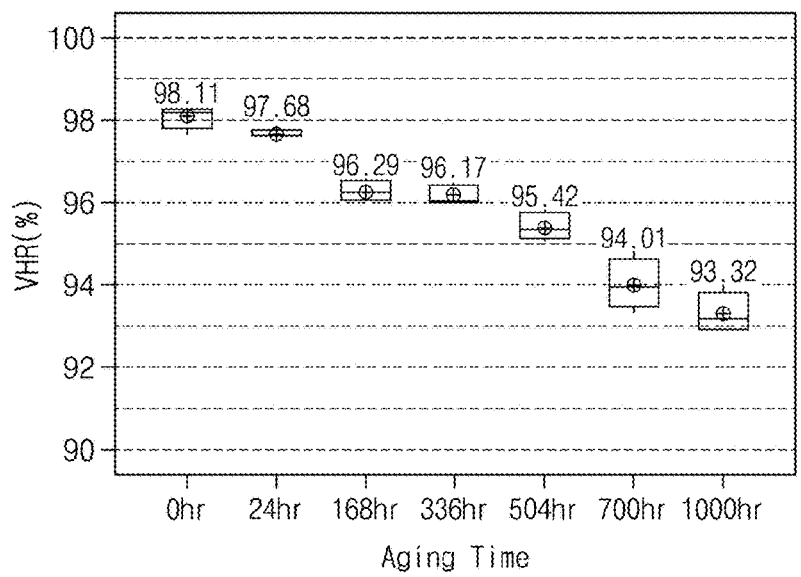
FIGS. 17A and 17B are graphs illustrating a voltage holding ratio in accordance with time in a liquid crystal display.
Figure 17B:
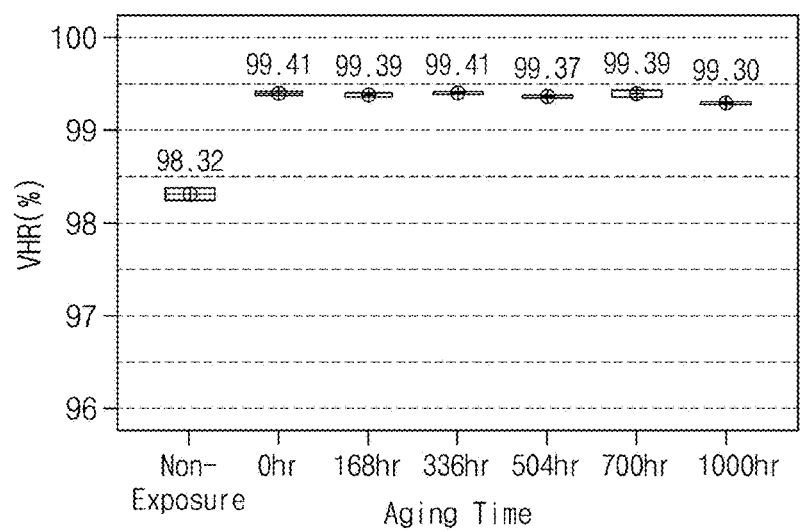

FIGS. 17A and 17B are graphs illustrating the change of a voltage holding ratio (VHR) of a liquid crystal display including a reactive mesogen. FIGS. 17A and 17B illustrate the change of a voltage holding ratio in accordance with time at room temperature.

FIG. 17A illustrates the change of a voltage holding ratio in accordance with time in a liquid crystal display including the comparative compound, and FIG. 17B illustrates the change of a voltage holding ratio in accordance with time in a liquid crystal display including Compound 12 of Compound Group 3.

Referring to the graph in FIG. 17A, the voltage holding ratio decreases in accordance with time for the liquid crystal display using the comparative compound as the reactive mesogen. In comparison, referring to the graph in FIG. 17B, the voltage holding ratio is maintained to about 99% or more in accordance with time in a liquid crystal display including Compound 12, which is a reactive mesogen according to an embodiment. Meanwhile, the term "non-exposure" on the X-axis in FIG. 17B represents the period prior to polymerization of the reactive mesogen provided together with a liquid crystal compound.

Referring to the results of FIGS. 17A and 17B, the reactive mesogen according to an embodiment includes a crown ether group at the terminal thereof and forms an alignment layer having high bonding energy with an electrode. Accordingly, the alignment layer may stably align a liquid crystal compound. In addition, by maintaining the voltage holding ratio high, the alignment layer formed by the reactive mesogen may stably align the liquid crystal, thereby improving the electrical properties of the liquid crystal display.

The reactive mesogen according to an embodiment includes at least one —OH group, an unsubstituted heterocycle, or a substituted or unsubstituted crown ether group at an anchoring group to increase the bonding energy with a substrate or an electrode layer of a liquid crystal display provided with the reactive mesogen. Accordingly, a liquid crystal display manufactured by providing a reactive mesogen according to an embodiment or a liquid crystal composition including a reactive mesogen according to an embodiment may have improved display quality. That is, due to the high bonding energy of the reactive mesogen according to an embodiment with respect to a substrate, an alignment layer of a liquid crystal display may be stably formed. Therefore, the physical properties for alignment of the liquid crystal compound in a liquid crystal display may be improved. In addition, the reactive mesogen according to an embodiment may increase the bonding energy with the substrate or the electrode layer of a liquid crystal display, stably align a liquid crystal compound, and increase a voltage holding ratio during driving a liquid crystal display, thereby improving the electrical properties of a liquid crystal display.

By introducing a core part which functions as an initiator, the reactive mesogen according to an embodiment may induce a spontaneous polymerization reaction, thereby improving the polymerization degree of the reactive mesogen. In addition, an alignment layer which may tilt a liquid crystal compound in a predetermined direction may be stably provided.

The reactive mesogen according to an embodiment includes two reactive groups or a crown ether group at the terminal which is an anchoring group, thereby stably forming an alignment layer in a liquid crystal display.

The liquid crystal composition according to an embodiment provides a novel reactive mesogen in addition to a liquid crystal compound, thereby improving the alignment properties of liquid crystal molecules.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

Accordingly, the technical scope of the present invention should not be limited to the detailed description of the disclosure but determined by claims.

What is claimed is:

1. A reactive mesogen represented by the following Formula 1:

[Formula 1]

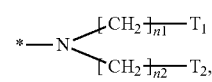

where $A_1$, $A_2$, and $A_3$ are each independently a substituted or unsubstituted divalent hydrocarbon ring, or a substituted or unsubstituted divalent heterocycle, a1, b1, and b2 are each independently an integer of 0 to 6, a2 and a3 are each independently 0 or 1, $L_1$ and $L_2$ are each independently a direct linkage, —O—, —S—, —CO—, —COO—, —OCOO—, —O(CH$_2$)$_{k1}$—, —S(CH$_2$)$_{k1}$—, —O(CF$_2$)$_{k1}$—, —S(CF$_2$)$_{k1}$—, —(CH$_2$)$_{k1}$—, —CF$_2$CH$_2$—, —(CF$_2$)$_{k1}$—, —CH=CH—, —CF=CF—, —C≡C—, —CH=CH—COO—, or —(CH$_2$)$_{k1}$—COO—(CH$_2$)$_{k2}$—O—, k1 and k2 are each independently an integer of 0 to 4, $Z_1$ and $Z_2$ are each independently a direct linkage, —O—, —S—, —CO—, —COO—, —OCOO—, —O(CH$_2$)$_{m1}$—, —S(CH$_2$)$_{m1}$—, —O(CF$_2$)$_{m1}$—, —S(CF$_2$)$_{m1}$—, —(CH$_2$)$_{m1}$—, —CF$_2$CH$_2$—, —(CF$_2$)$_{m1}$—, —CH=CH—, —CF=CF—, —C≡C—, —CH=CH—COO—, —(CH$_2$)$_{m1}$—COO—, —(CH$_2$)$_{m1}$—COO—(CH$_2$)$_{m2}$—O—, —CH—(S$_p$—Pa)—, —CH$_2$CH—(S$_p$—Pa)—, or —(CH—(S$_p$—Pa)—CH—(S$_p$—Pa))—, m1 and m2 are each independently an integer of 0 to 4, S$_p$ is a direct linkage, or a spacer group, Pa is a polymerizable group, B is an unsubstituted heterocycle, a substituted or unsubstituted crown ether group, or

n1 and n2 are each independently an integer of 1 to 12, $T_1$ and $T_2$ are each independently —OH, —CH$_3$, —CF$_3$, —CHF$_2$, —CH$_2$F, —CH$_2$Br, —CHBr$_2$, —CHCl$_2$, or —CH$_2$Cl, and at least one of $T_1$ and $T_2$ is —OH.

2. The reactive mesogen of claim 1, wherein $A_1$, $A_2$, and $A_3$ are each independently a substituted or unsubstituted aromatic ring having 6 to 30 carbon atoms for forming a ring, a substituted or unsubstituted heteroaromatic ring having 2 to 30 carbon atoms for forming a ring, a substituted or unsubstituted aliphatic ring having 5 to 30 carbon atoms for forming a ring, or a substituted or unsubstituted hetero aliphatic ring having 2 to 30 carbon atoms for forming a ring.

3. The reactive mesogen of claim 1, wherein $A_1$, $A_2$, and $A_3$ are each independently selected from substituted or unsubstituted ring compounds of the following A-1 to A-22:

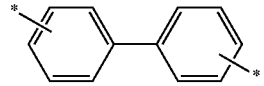

A-1

A-2

A-3

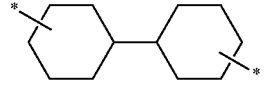

A-4

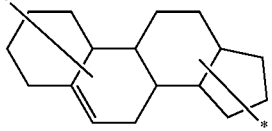

A-5

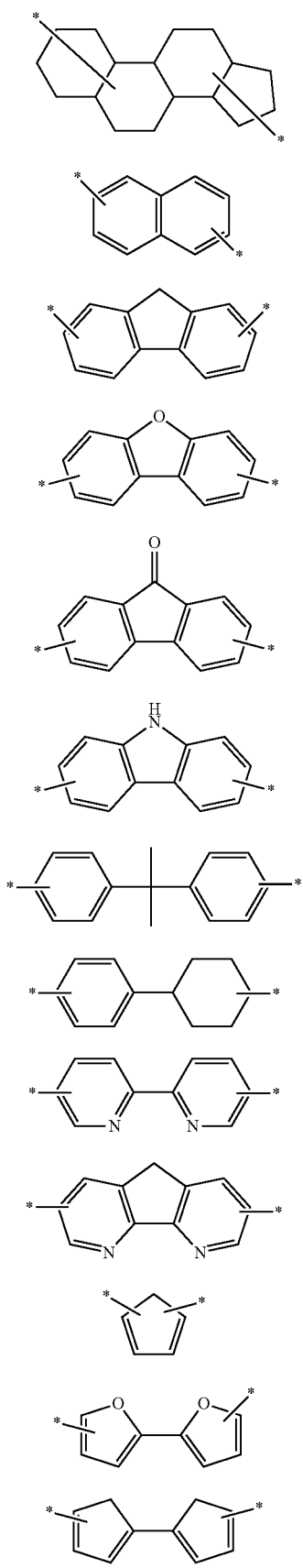

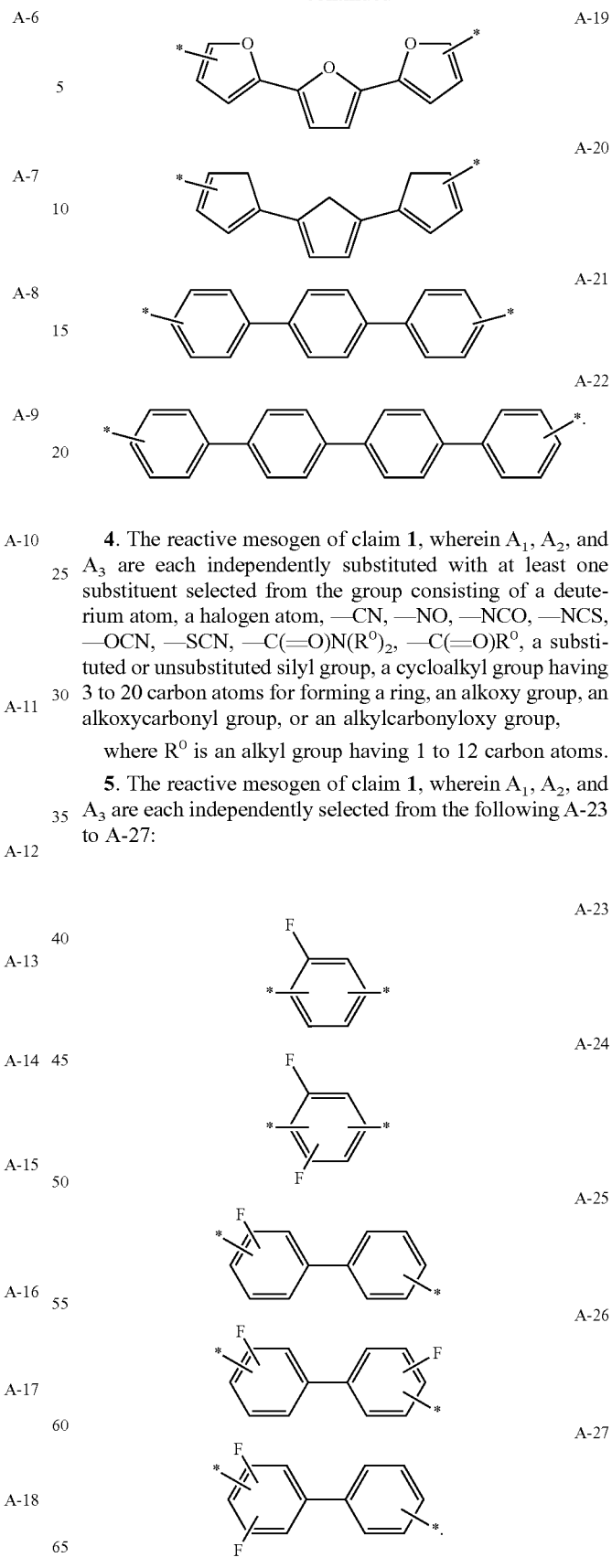

4. The reactive mesogen of claim 1, wherein $A_1$, $A_2$, and $A_3$ are each independently substituted with at least one substituent selected from the group consisting of a deuterium atom, a halogen atom, —CN, —NO, —NCO, —NCS, —OCN, —SCN, —C(=O)N(R⁰)$_2$, —C(=O)R⁰, a substituted or unsubstituted silyl group, a cycloalkyl group having 3 to 20 carbon atoms for forming a ring, an alkoxy group, an alkoxycarbonyl group, or an alkylcarbonyloxy group, where $R^0$ is an alkyl group having 1 to 12 carbon atoms.

5. The reactive mesogen of claim 1, wherein $A_1$, $A_2$, and $A_3$ are each independently selected from the following A-23 to A-27:

6. The reactive mesogen of claim 1, wherein B is
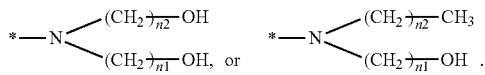
7. The reactive mesogen of claim 1, wherein B is one of the following B-1 to B-18:
B-1
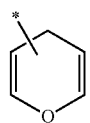
B-2
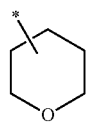
B-3
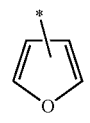
B-4
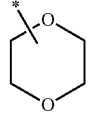
B-5
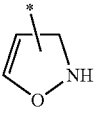
B-6
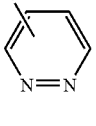
B-7
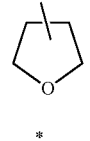
B-8
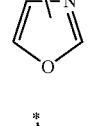
B-9
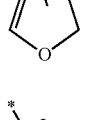
B-10
B-11
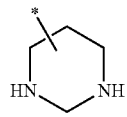
B-12
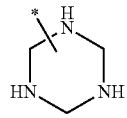
B-13
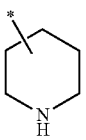
B-14
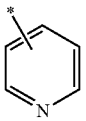
B-15
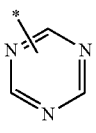
B-16
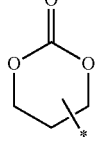
B-17
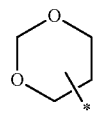
B-18
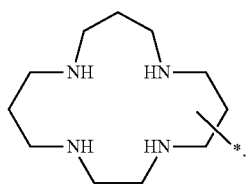
8. The reactive mesogen of claim 1, wherein B is one of the following E-1 to E-13:
E-1
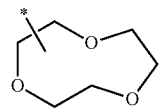
E-2
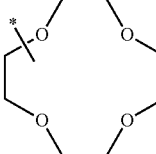

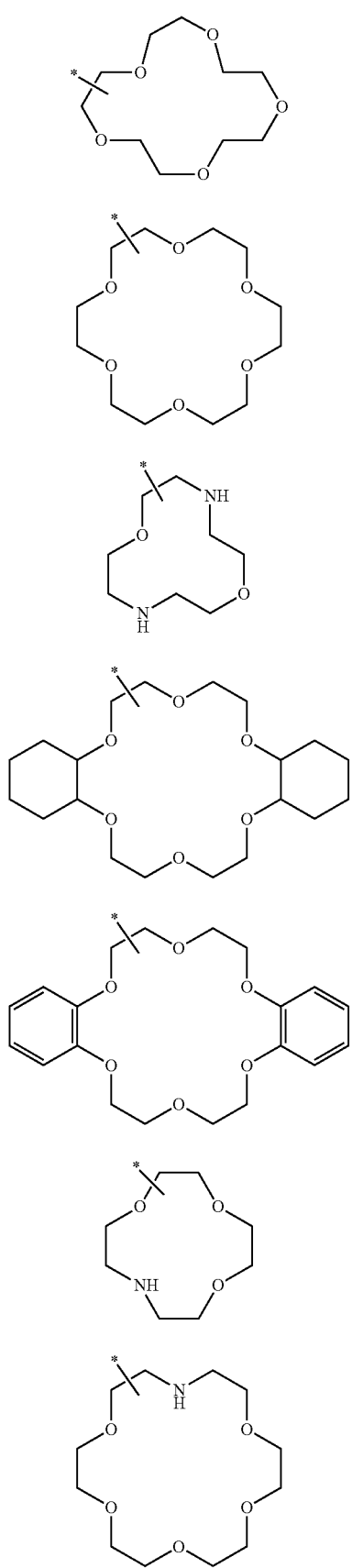
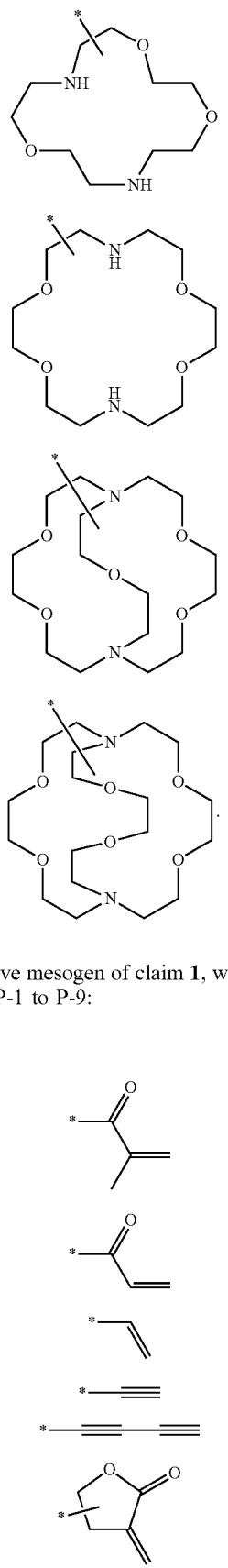
9. The reactive mesogen of claim 1, wherein Pa is one of the following P-1 to P-9:
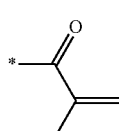
P-1
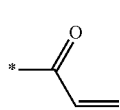
P-2
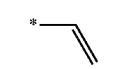
P-3
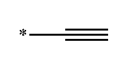
P-4
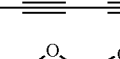
P-5
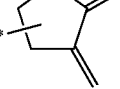
P-6

10. The reactive mesogen of claim 1, wherein Formula 1 is selected from compounds in the following Compound Group 1:
[Compound Group 1]
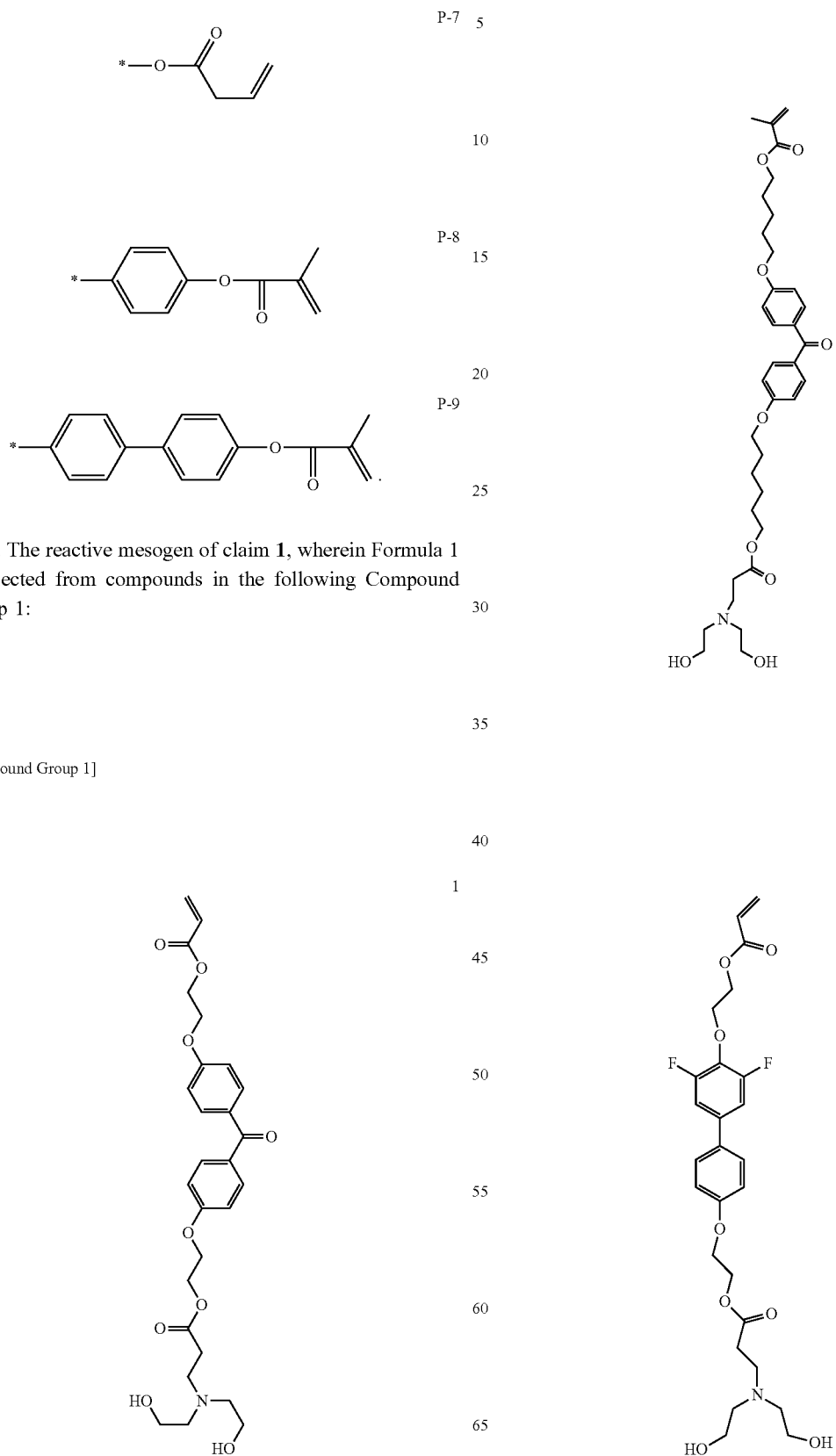

-continued
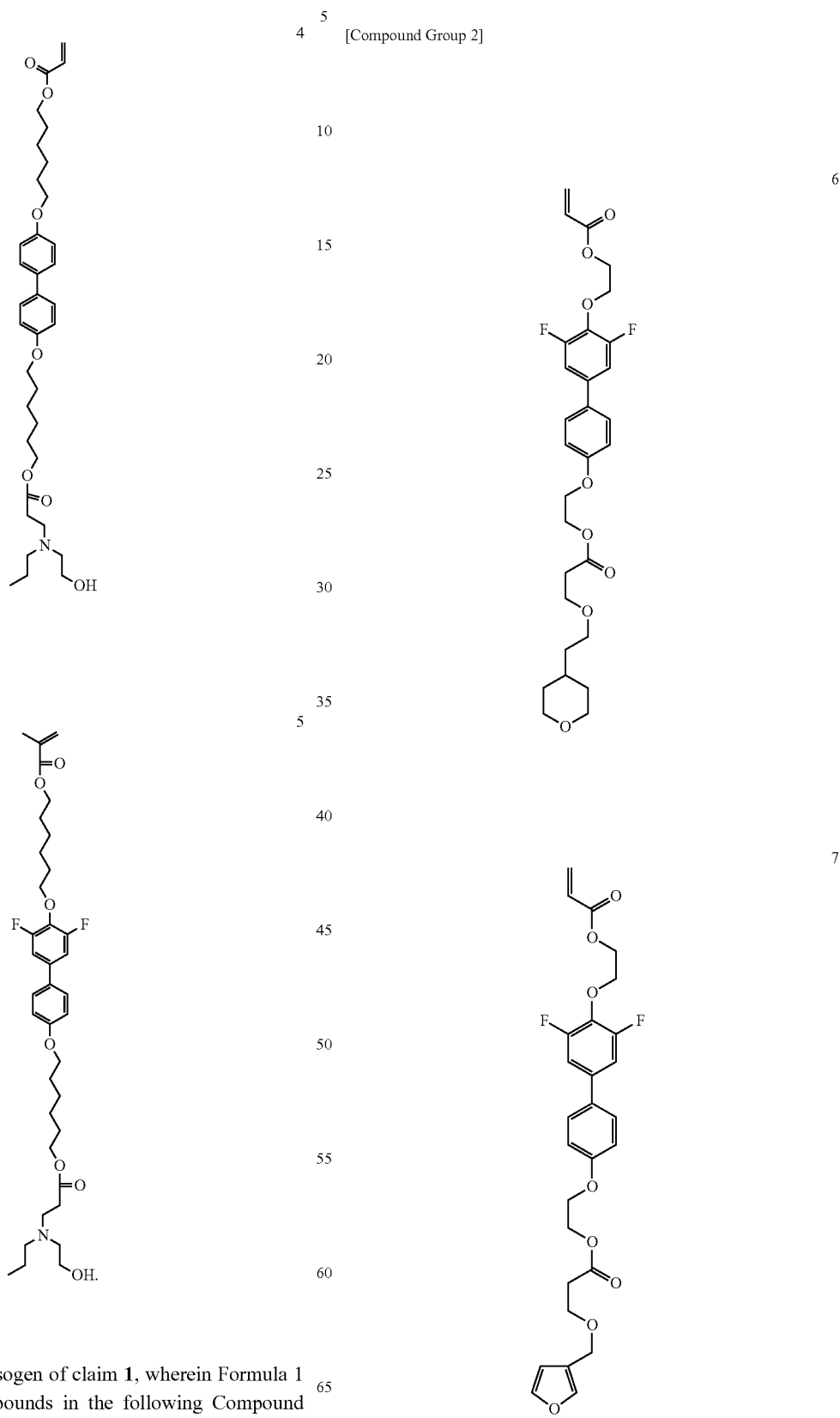
11. The reactive mesogen of claim 1, wherein Formula 1 is selected from compounds in the following Compound Group 2:

101
-continued
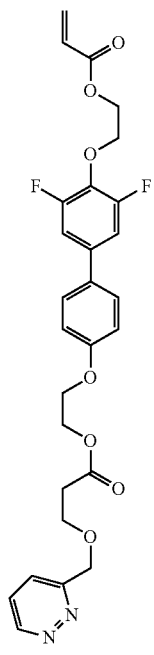
102
-continued
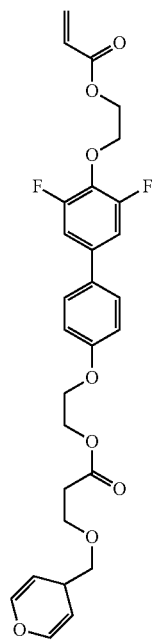
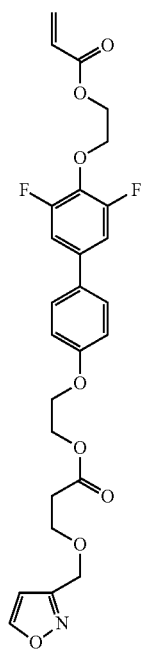
12. The reactive mesogen of claim 1, wherein Formula 1 is selected from compounds in the following Compound Group 3:

[Compound Group 3]
12
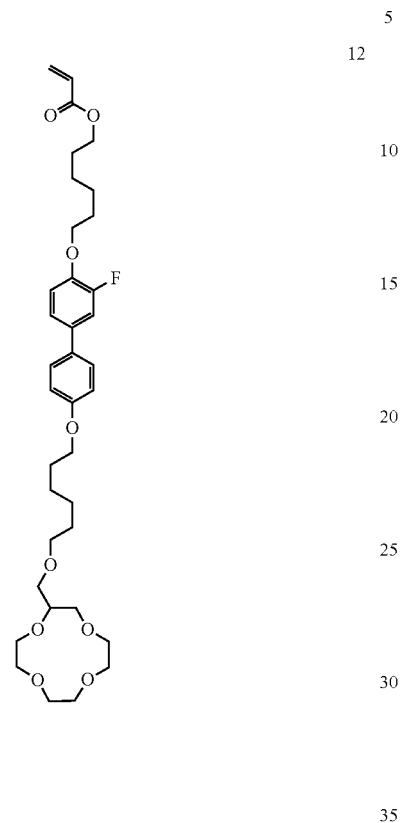
13
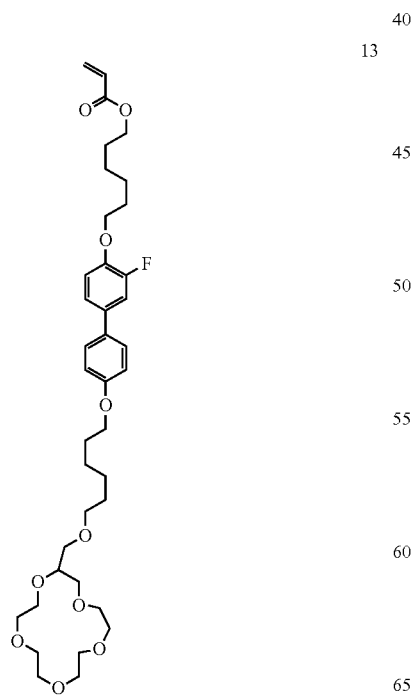

14
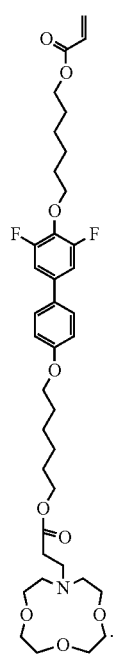
* * * * *